US011717701B2

United States Patent
Ollila et al.

(10) Patent No.: US 11,717,701 B2
(45) Date of Patent: Aug. 8, 2023

(54) ADJOINT TRANSPORT FOR DOSE IN BEAM ANGLE OPTIMIZATION FOR EXTERNAL BEAM RADIATION THERAPY

(71) Applicants: Siemens Healthineers International AG, Steinhausen (CH); Varian Medical Systems, Inc., Palo Alto, CA (US)

(72) Inventors: Santtu Ollila, Helsinki (FI); Todd Arlin Wareing, Blackfoot, ID (US); John Morton McGhee, Hollis, NH (US); Douglas Allen Barnett, Jr., Pattersonville, NY (US); Alexander Enrique Maslowski, Helsinki (FI)

(73) Assignees: SIEMENS HEALTHINEERS INTERNATIONAL AG, Steinhausen (CH); VARIAN MEDICAL SYSTEMS, INC., Palo Alto, CA (US)

(*) Notice: Subject to any disclaimer, the term of this patent is extended or adjusted under 35 U.S.C. 154(b) by 491 days.

(21) Appl. No.: 16/586,661

(22) Filed: Sep. 27, 2019

(65) Prior Publication Data

US 2020/0101325 A1 Apr. 2, 2020

Related U.S. Application Data

(60) Provisional application No. 62/738,741, filed on Sep. 28, 2018.

(51) Int. Cl.
*A61N 5/10* (2006.01)
*G06T 7/00* (2017.01)

(52) U.S. Cl.
CPC .......... *A61N 5/1031* (2013.01); *A61N 5/103* (2013.01); *A61N 5/1037* (2013.01);
(Continued)

(58) Field of Classification Search
CPC ...... A61N 5/10–1084; A61N 2005/1085–1098
See application file for complete search history.

(56) References Cited

U.S. PATENT DOCUMENTS

| 2002/0051513 A1 | 5/2002 | Pugachev et al. |
| 2008/0004845 A1 | 1/2008 | Failla et al. |

(Continued)

FOREIGN PATENT DOCUMENTS

| CN | 107206253 A | 9/2017 |
| CN | 107666940 A | 2/2018 |

(Continued)

OTHER PUBLICATIONS

Hilbig et al., "Design of an Inverse Planning System For Radiotherapy Using Linear Optimization//Entwicklung Eines Inversen Bestrahlungsplanungssystems Mit Linearer Optimierung", Zeitschrift Fuer Medizinische Physik, vol. 12, No. 2, 2002.

(Continued)

*Primary Examiner* — Thaddeus B Cox
(74) *Attorney, Agent, or Firm* — Potomac Law Group, PLLC

(57) ABSTRACT

A method of beam angle optimization for an IMRT radiotherapy treatment includes providing a patient model having one or more regions of interest (ROIs), defining a delivery coordinate space (DCS), for each ROI, solving an adjoint transport to obtain an adjoint solution field from the ROI, for each vertex in the DCS, evaluating an adjoint photon fluence by performing ray tracing of the adjoint solution field, evaluating a dose of the ROI using the adjoint photon fluence, for each vertex in the DCS, evaluating a respective beam's eye view (BEV) score of each pixel of a BEV plane using the doses of the one or more ROIs, determining one or more BEV regions in the BEV plane based on the BEV scores, determining a BEV region connectivity manifold (Continued)

based on the BEV regions, and determining a set of IMRT fields based on the BEV region connectivity manifold.

9 Claims, 25 Drawing Sheets

(52) U.S. Cl.
CPC ......... *A61N 5/1039* (2013.01); *A61N 5/1045* (2013.01); *A61N 5/1081* (2013.01); *G06T 7/0012* (2013.01); *A61N 2005/1034* (2013.01); *G06T 2207/20072* (2013.01); *G06T 2207/30004* (2013.01); *G06T 2207/30241* (2013.01)

(56) References Cited

U.S. PATENT DOCUMENTS

| | | |
|---|---|---|
| 2017/0189717 A1 | 7/2017 | MacDonald et al. |
| 2017/0354832 A1 | 12/2017 | Bush et al. |
| 2018/0078785 A1* | 3/2018 | Ollila .................. A61N 5/1039 |
| 2018/0078789 A1 | 3/2018 | Ollila et al. |
| 2018/0099151 A1* | 4/2018 | Sullivan ............... A61N 5/1039 |
| 2019/0015060 A1 | 1/2019 | Weiss |
| 2020/0101322 A1 | 4/2020 | Ollila et al. |
| 2020/0101323 A1 | 4/2020 | Ollila |
| 2020/0101325 A1 | 4/2020 | Ollila et al. |

FOREIGN PATENT DOCUMENTS

| | | |
|---|---|---|
| WO | 2011053802 A2 | 5/2011 |
| WO | 2011153639 A2 | 12/2011 |
| WO | 2016116868 A1 | 7/2016 |
| WO | 2016188754 A1 | 12/2016 |
| WO | WO 2017/152286 A1 | 9/2017 |
| WO | WO 2018/083072 A1 | 5/2018 |
| WO | 2018137772 A1 | 8/2018 |

OTHER PUBLICATIONS

International Application No. PCT/US2019/053623, "International Search Report and Written Opinion", dated Apr. 9, 2020, 18 pages.
International Application No. PCT/US2019/053623, "Invitation to Pay Additional Fees and, Where Applicable, Protest Fee", dated Jan. 22, 2020, 11 pages.
Office Action dated Sep. 15, 2022, in Chinese Patent Application No. 201980063700.6.

* cited by examiner

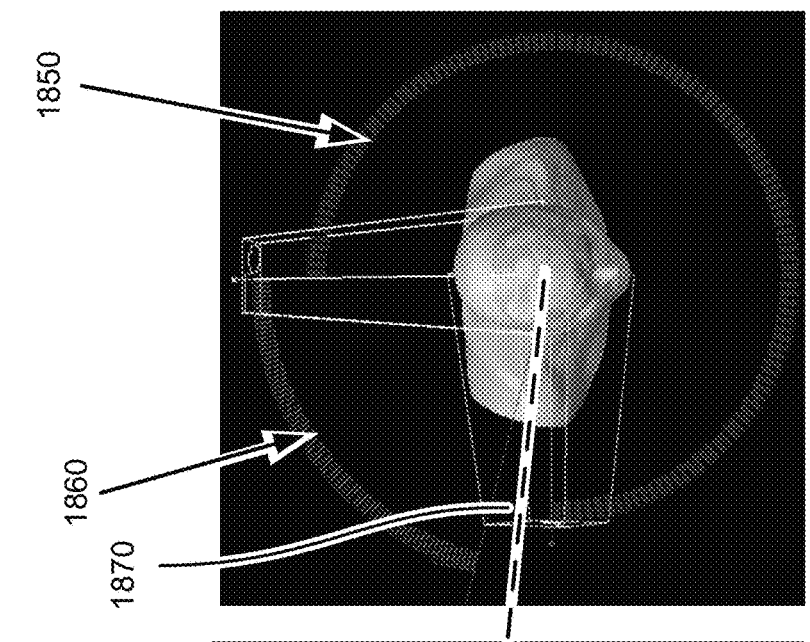
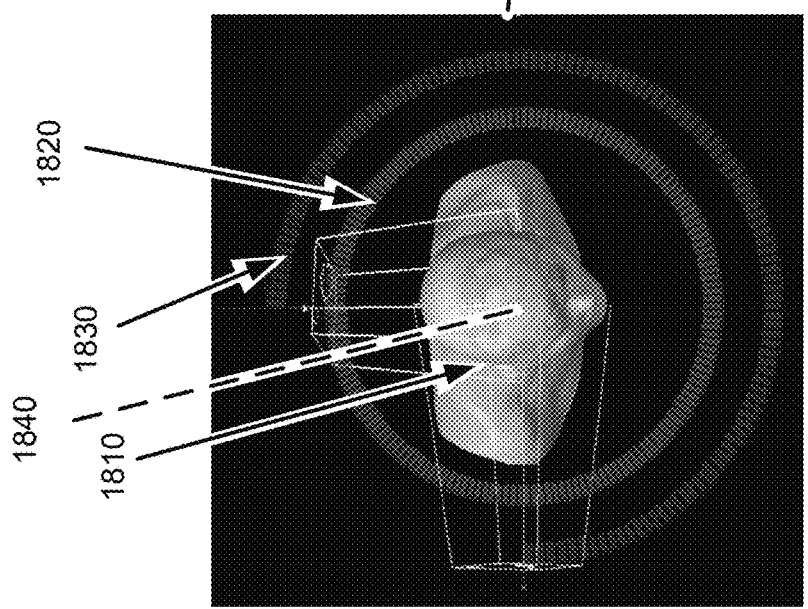
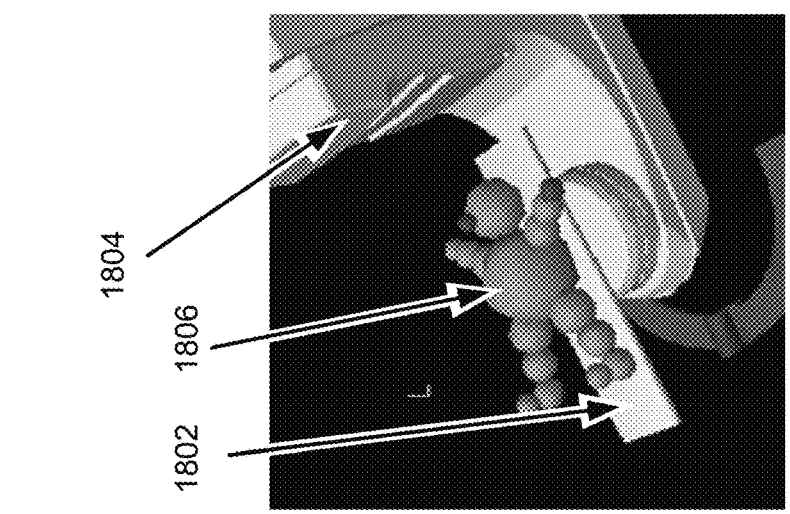
FIG. 18C
FIG. 18B
FIG. 18A

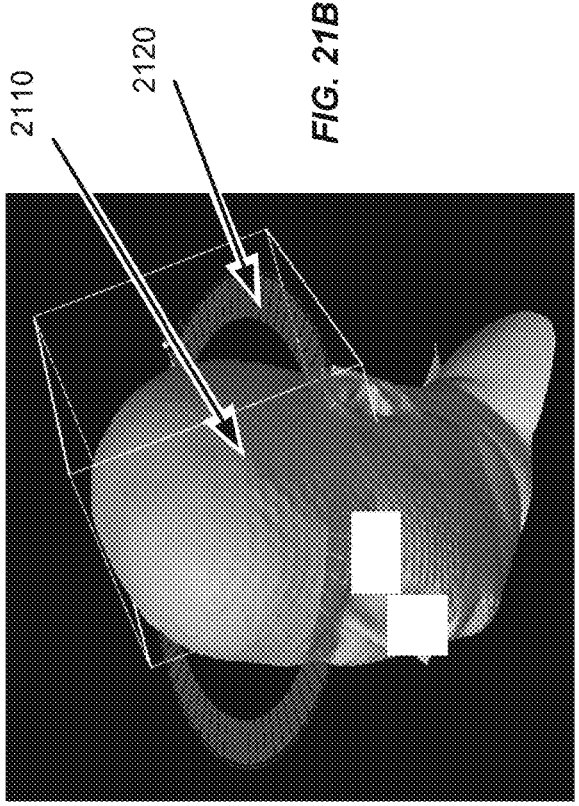
*FIG. 21A*
*FIG. 21B*
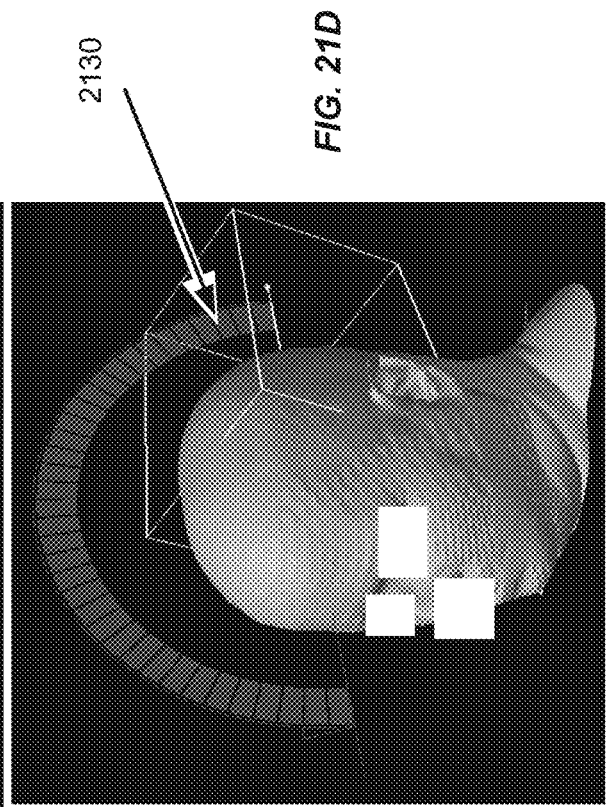
*FIG. 21C*
*FIG. 21D*
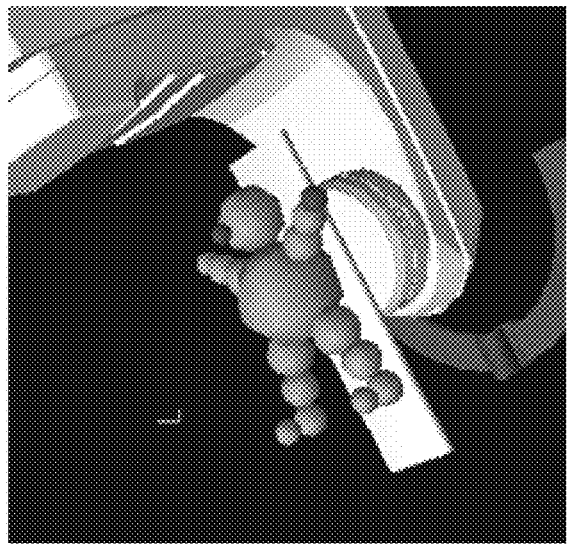
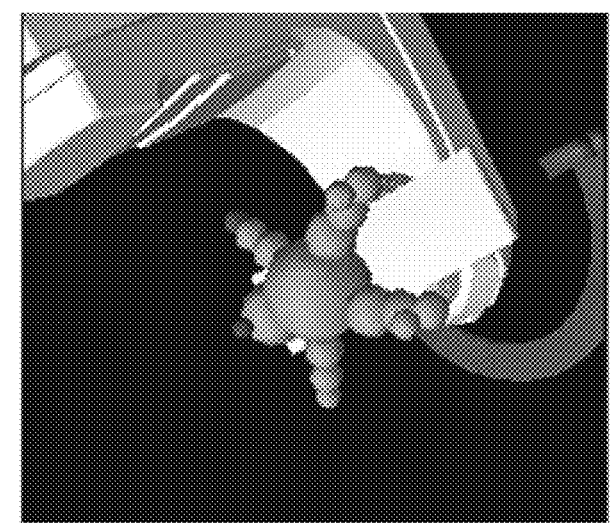

ADJOINT TRANSPORT FOR DOSE IN BEAM ANGLE OPTIMIZATION FOR EXTERNAL BEAM RADIATION THERAPY

CROSS-REFERENCE TO RELATED APPLICATIONS

The present application is a non-provisional application of and claims the benefit and priority under 35 U.S.C. 119(e) of U.S. Provisional Application No. 62/738,741, filed Sep. 28, 2018, entitled "ADJOINT TRANSPORT FOR DOSE IN TREATMENT TRAJECTORY OPTIMIZATION AND BEAM ANGLE OPTIMIZATION FOR EXTERNAL BEAM RADIATION THERAPY," the entire content of which is incorporated herein by reference for all purposes.

The following three U.S. patent applications (including this one) are being filed concurrently, and the entire disclosures of the other applications are incorporated by reference into this application for all purposes:

U.S. application Ser. No. 16/586,654, filed Sep. 27, 2019, entitled "ADJOINT TRANSPORT FOR DOSE IN TREATMENT TRAJECTORY OPTIMIZATION FOR EXTERNAL BEAM RADIATION THERAPY";

U.S. application Ser. No. 16/586,661, filed Sep. 27, 2019, entitled "ADJOINT TRANSPORT FOR DOSE IN BEAM ANGLE OPTIMIZATION FOR EXTERNAL BEAM RADIATION THERAPY"; and U.S. application Ser. No. 16/586,666, filed Sep. 27, 2019, entitled "HYBRID TRAJECTORY AND BEAM ANGLE OPTIMIZATION FOR EXTERNAL BEAM RADIATION THERAPY".

BACKGROUND

Significant developments have been made in inverse treatment planning of external beam radiation therapies using, e.g., IMRT and VMAT treatment modalities. As both plan quality requirements and requirements on the clinics' patient throughput increase, the role of automation and a higher degree of personalization of treatment plans become increasingly important. Prior to inverse-optimization of the MLC leaf sequence and dose rates in a radiation treatment plan, treatment fields, such as VMAT trajectories and IMRT fields, may need to be determined. Each treatment field may be associated with a beam energy (e.g., 6 MeV or 15 MeV) and profile (e.g., flat or flattening-filter free). The choice of beam energy and treatment geometry (e.g., isocenter(s), starting and stopping gantry angles, and collimator angle(s) of VMAT trajectories, or gantry angle, couch angle, collimator angle, and jaw positions of IMRT fields) may be dictated by a clinical protocol for a given treatment site. Such a protocol may be sub-optimal considering the variability in patient anatomy and in clinical goals. Therefore, there is a need for improved methods of optimizing treatment geometries.

SUMMARY

According to some embodiments, a method of trajectory optimization for radiotherapy treatment includes providing a patient model that includes one or more regions of interest (ROIs) for the radiotherapy treatment, and defining a delivery coordinate space (DC S) having a set of candidate vertices. Each respective candidate vertex defines a respective beam's eye view (BEV) plane. The method further includes, for each respective ROI of the one or more ROIs, solving an adjoint transport to obtain an adjoint solution field from the respective ROI; and for each respective candidate vertex in the DCS, and for each respective pixel of the respective BEV plane defined by the respective candidate vertex, evaluating an adjoint photon fluence originating from a respective beamlet incident from the respective candidate vertex and passing through the respective pixel by performing ray tracing of the adjoint solution field; and evaluating a respective dose of the respective ROI from the respective beamlet using the adjoint photon fluence. The method further includes for each respective candidate vertex in the DCS, and for each respective pixel of the respective BEV plane defined by the respective candidate vertex, evaluating a respective BEV score of the respective pixel using the doses of the one or more ROIs evaluated for the respective beamlet incident from the respective candidate vertex and passing through the respective pixel; and determining one or more BEV regions in the respective BEV plane based on the BEV scores of the pixels of the BEV planes corresponding to the set of candidate vertices in the DCS. The method further includes determining a BEV region connectivity manifold based on the BEV regions of the BEV planes of the set of candidate vertices in the DCS. The BEV region connectivity manifold represents connections between contiguous BEV regions between adjacent vertices. The method further includes determining one or more optimal treatment trajectories based on the BEV region connectivity manifold.

According to some embodiments, a method of trajectory optimization for radiotherapy treatment includes providing a patient model that has one or more regions of interest (ROIs) for the radiotherapy treatment, and defining a delivery coordinate space (DCS) having a set of candidate vertices. Each respective candidate vertex defines a respective beam's eye view (BEV) plane. The method further includes identifying a plurality of candidate energy modes for the radiotherapy treatment; and for each respective energy mode of the plurality of candidate energy modes, for each respective BEV plane of a respective candidate vertex in the DCS, and for each respective ROI of the one or more ROIs, evaluating a respective dose of the respective ROI from a respective beamlet incident from the respective candidate vertex and passing through a respective pixel of the respective BEV plane using transport solutions for the respective energy mode. The method further includes evaluating a respective BEV score of the respective pixel using the doses of the one or more ROIs evaluated for the respective beamlet; determining one or more BEV regions in the respective BEV plane for the respective energy mode based on the BEV scores of the pixels of the BEV planes corresponding to the set of candidate vertices in the DCS; and determining a respective BEV region connectivity manifold for the respective energy mode based on the BEV regions of the BEV planes of the set of candidate vertices in the DCS. The respective BEV region connectivity manifold represents connections between contiguous BEV regions between adjacent vertices. The method further includes determining a plurality of candidate sets of optimal treatment trajectories by: for each respective energy mode of the plurality of candidate energy modes, determining a respective candidate set of optimal treatment trajectories based on the respective BEV region connectivity manifold for the respective energy mode. The method further includes selecting one of the plurality of candidate sets of optimal treatment trajectories as a final set of optimal treatment trajectories based on an objective function. The final set of optimal treatment trajectories corresponds to an optimal energy mode among the plurality of candidate energy modes.

According to some embodiments, a method of trajectory optimization for radiotherapy treatment includes providing a patient model including one or more regions of interest (ROIs) for the radiotherapy treatment, and defining a delivery coordinate space (DCS) having a set of candidate vertices. Each respective candidate vertex defines a respective beam's eye view (BEV) plane. The method further includes identifying a first energy mode and a second energy mode for the radiotherapy treatment; for the first energy mode, determining a first BEV region connectivity manifold by evaluating doses of the one or more ROIs for each respective BEV plane corresponding to each respective candidate vertex of the DCS using transport solutions for the first energy mode; and for the second energy mode, determining a second BEV region connectivity manifold by evaluating doses of the one or more ROIs for each respective BEV plane corresponding to each respective candidate vertex of the DCS using transport solutions for the second energy mode. The method further includes determining a set of optimal treatment trajectories based on the first BEV region connectivity manifold and the second BEV region connectivity manifold.

According to some embodiments, a method of beam angle optimization for an IMRT radiotherapy treatment include providing a patient model that has one or more regions of interest (ROIs) for the IMRT radiotherapy treatment, and defining a delivery coordinate space (DCS) having a set of candidate vertices. Each respective candidate vertex defines a respective beam's eye view (BEV) plane. The method further includes, for each respective ROI of the one or more ROIs, solving an adjoint transport to obtain an adjoint solution field from the respective ROI; and for each respective candidate vertex in the DCS, for each respective pixel of the respective BEV plane defined by the respective candidate vertex, evaluating an adjoint photon fluence originating from a respective beamlet incident from the respective candidate vertex and passing through the respective pixel by performing ray tracing of the adjoint solution field; evaluating a respective dose of the respective ROI from the respective beamlet using the adjoint photon fluence. The method further includes, for each respective candidate vertex in the DCS, and for each respective pixel of the respective BEV plane defined by the respective candidate vertex, evaluating a respective BEV score of the respective pixel using the doses of the one or more ROIs evaluated for the respective beamlet incident from the respective candidate vertex and passing through the respective pixel; and determining one or more BEV regions in the respective BEV plane based on the BEV scores of the pixels of the BEV planes corresponding to the set of candidate vertices in the DCS. The method further includes determining a BEV region connectivity manifold based on the BEV regions of the BEV planes of the set of candidate vertices in the DCS. The BEV region connectivity manifold represents connections between contiguous BEV regions between adjacent vertices. The method further includes determining a set of IMRT fields based on the BEV region connectivity manifold. Each respective IMRT field of the set of IMRT fields defines a beam angle corresponding to a respective vertex in the DCS.

According to some embodiments, a method of beam angle optimization for an IMRT radiotherapy treatment includes providing a patient model having one or more regions of interest (ROIs) for the IMRT radiotherapy treatment, and defining a delivery coordinate space (DCS) having a set of candidate vertices. Each respective candidate vertex defines a respective beam's eye view (BEV) plane. The method further includes identifying a plurality of candidate energy modes for the IMRT radiotherapy treatment; and for each respective energy mode of the plurality of candidate energy modes, for each respective BEV plane of a respective candidate vertex in the DCS, and for each respective ROI of the one or more ROIs: evaluating a respective dose of the respective ROI from a respective beamlet incident from the respective candidate vertex and passing through a respective pixel of the respective BEV plane using transport solutions for the respective energy mode; evaluating a respective BEV score of the respective pixel using the doses of the one or more ROIs evaluated for the respective beamlet; and determining one or more BEV regions in the respective BEV plane for the respective energy mode based on the BEV scores of the pixels of the BEV planes corresponding to the set of candidate vertices in the DCS. The method further includes determining a respective BEV region connectivity manifold for the respective energy mode based on the BEV regions of the BEV planes of the set of candidate vertices in the DCS. The respective BEV region connectivity manifold represents connections between contiguous BEV regions between adjacent vertices. The method further includes determining a plurality of candidate sets of IMRT fields by, for each respective energy mode of the plurality of candidate energy modes, determining a respective candidate set of IMRT fields based on the respective BEV region connectivity manifold for the respective energy mode, each respective IMRT field defining a beam angle corresponding to a respective vertex in the DCS. The method further includes selecting one of the plurality of candidate sets of IMRT fields as an optimal set of IMRT fields based on an objective function. The optimal set of IMRT fields corresponds to an optimal energy mode among the plurality of candidate energy modes.

According to some embodiments, a method of beam angle optimization in an IMRT radiotherapy treatment includes providing a patient model including one or more regions of interest (ROIs) for the IMRT radiotherapy treatment, and defining a delivery coordinate space (DCS) having a set of candidate vertices. Each respective candidate vertex defines a respective beam's eye view (BEV) plane. The method further includes identifying a first energy mode and a second energy mode for the IMRT radiotherapy treatment; for the first energy mode, determining a first BEV region connectivity manifold by evaluating doses of the one or more ROIs for each respective BEV plane corresponding to each respective candidate vertex of the DCS using transport solutions for the first energy mode; and for the second energy mode, determining a second BEV region connectivity manifold by evaluating doses of the one or more ROIs for each respective BEV plane corresponding to each respective candidate vertex of the DCS using transport solutions for the second energy mode. The method further includes determining a set of IMRT fields based on the first BEV region connectivity manifold for the first energy mode and the second BEV region connectivity manifold for the second energy mode. Each respective IMRT field of the set of IMRT fields defines a beam angle corresponding to a respective vertex in the DCS.

According to some embodiments, a method of determining treatment geometries for a radiotherapy treatment includes providing a patient model having one or more regions of interest (ROIs) for the radiotherapy treatment, and defining a delivery coordinate space (DCS) having a set of candidate vertices. Each respective candidate vertex defines a respective beam's eye view (BEV) plane. The method further includes, for each respective BEV plane of a respective candidate vertex in the DCS, and for each respective ROI of the one or more ROIs, evaluating a respective dose of the respective ROI from a respective beamlet incident from the respective candidate vertex and passing through a respective pixel of the respective BEV plane using transport solutions of the respective beamlet; evaluating a respective BEV score of the respective pixel using the doses of the one or more ROIs evaluated for the respective beamlet; and determining one or more BEV regions in the respective BEV plane based on the BEV scores of the pixels of the BEV planes corresponding to the set of candidate vertices in the DCS. The method further includes determining a BEV region connectivity manifold based on the BEV regions of the BEV planes of the set of candidate vertices in the DCS. The BEV region connectivity manifold represents connections between contiguous BEV regions between adjacent vertices. The method further includes determining a set of treatment trajectories based on the BEV region connectivity manifold. Each treatment trajectory defines a respective path through a respective set of vertices in the DCS. The method further includes determining one or more IMRT fields, each respective IMRT field defines a respective direction of incidence corresponding to a respective vertex in the DCS.

According to some embodiments, a method of determining treatment geometries for a radiotherapy treatment includes providing a patient model having one or more regions of interest (ROIs) for the radiotherapy treatment, and defining a first delivery coordinate space and a second delivery coordinate space. The first delivery coordinate space has a first set of candidate vertices. The second delivery coordinate space has a second set of candidate vertices. Each vertex of the first set of candidate vertices or the second set of candidate vertices defines a respective beam's eye view (BEV) plane. The method further includes determining a first beam's eye view (BEV) region connectivity manifold by evaluating doses of the one or more ROIs for each respective BEV plane corresponding to each respective vertex of the first set of candidate vertices of the first delivery coordinate space, and determining a first set of treatment trajectories based on the first BEV region connectivity manifold. Each treatment trajectory of the first set of treatment trajectories defines a respective path through a respective set of vertices in the first delivery coordinate space. The method further includes determining a first set of IMRT fields. Each of the first set of IMRT fields corresponds to a respective vertex in the second delivery coordinate space.

According to some embodiments, a method of determining treatment geometries for a radiotherapy treatment includes providing a patient model having one or more regions of interest (ROIs) for the radiotherapy treatment, and defining a delivery coordinate space (DCS) having a set of candidate vertices. Each respective candidate vertex defines a respective beam's eye view (BEV) plane. The method further includes identifying a first energy mode and a second energy mode for the radiotherapy treatment; for the first energy mode, determining a first BEV region connectivity manifold by evaluating doses of the one or more ROIs for each respective BEV plane corresponding to each respective candidate vertex of the DCS using transport solutions for the first energy mode; for the second energy mode, determining a second BEV region connectivity manifold by evaluating doses of the one or more ROIs for each respective BEV plane corresponding to each respective candidate vertex of the DCS using transport solutions for the second energy mode; determining a set of optimal treatment trajectories based on the first BEV region connectivity manifold and the second BEV region connectivity manifold; and determining a set of IMRT fields. Each respective IMRT field of the set of IMRT fields corresponds to a respective vertex in the delivery coordinate space.

These and other embodiments of the disclosure are described in detail below. For example, other embodiments are directed to systems, devices, and computer readable media associated with methods described herein.

A better understanding of the nature and advantages of embodiments of the present disclosure may be gained with reference to the following detailed description and the accompanying drawings.

BRIEF DESCRIPTION OF THE DRAWINGS

FIG. 18A illustrates a configuration of a C-arm linear accelerator radiotherapy treatment system according to some embodiments.

FIG. 18B shows a view of a patient model from the top of the patient's head and two exemplary treatment trajectories according to some embodiments.

FIG. 18C shows a view of a patient model from the top of the patient's head and two exemplary treatment trajectories according to some embodiments.

FIG. 21A illustrates a first delivery coordinate space in a first configuration of a C-arm linear accelerator radiotherapy treatment system according to some embodiments.

FIG. 21B shows a treatment trajectory in the first delivery coordinate illustrated in FIG. 21A according to some embodiments.

FIG. 21C illustrates a second delivery coordinate space in a second configuration of a C-arm linear accelerator radiotherapy treatment system according to some embodiments.

FIG. 21D shows a treatment trajectory in the second delivery coordinate illustrated in FIG. 21C according to some embodiments.

DETAILED DESCRIPTION

The present disclosure relates generally to treatment planning for radiotherapy treatment using external-beam radiotherapy treatment systems, and is more particularly directed to optimizing trajectories and field geometries in a radiation treatment plan. Beam's eye view (BEV) regions and BEV region connectivity manifold may be determined by evaluating dose response of each region of interest for each vertex in a delivery coordinate space (DCS). The information contained in the BEV regions and BEV region connectivity manifold may be used to generate optimized trajectories or optimized field geometries in a radiation treatment plan.

The detailed description of the various embodiments is organized as follows. Section I discusses some exemplary radiation treatment systems. Section II discusses radiation treatment planning. Section III discusses beam's eye view (BEV) sectioning for an approach to treatment trajectory optimization in radiotherapy (referred to herein as TORUS). The TORUS approach may require commutationally costly and time-consuming dose evaluations. Section IV discusses two approaches to dose evaluation: the forward transport approach and the adjoint transport approach. The adjoint transport approach may have the advantage of more computationally efficient dose evaluation, especially for optimizations that consider multiple candidate energy modes. Section V discusses trajectory optimization using adjoint transport for dose. Section VI discusses beam angle optimization in IMRT radiotherapy treatment using adjoint transport for dose. Section VII discusses trajectory optimization considering multiple candidate energy modes. Section VIII discusses beam angle optimization considering multiple candidate energy modes. Section IX discusses applications of TORUS and BEV sectioning based methodologies to hybrid trajectory and beam angle optimization.

I. Treatment System

Figure 1:
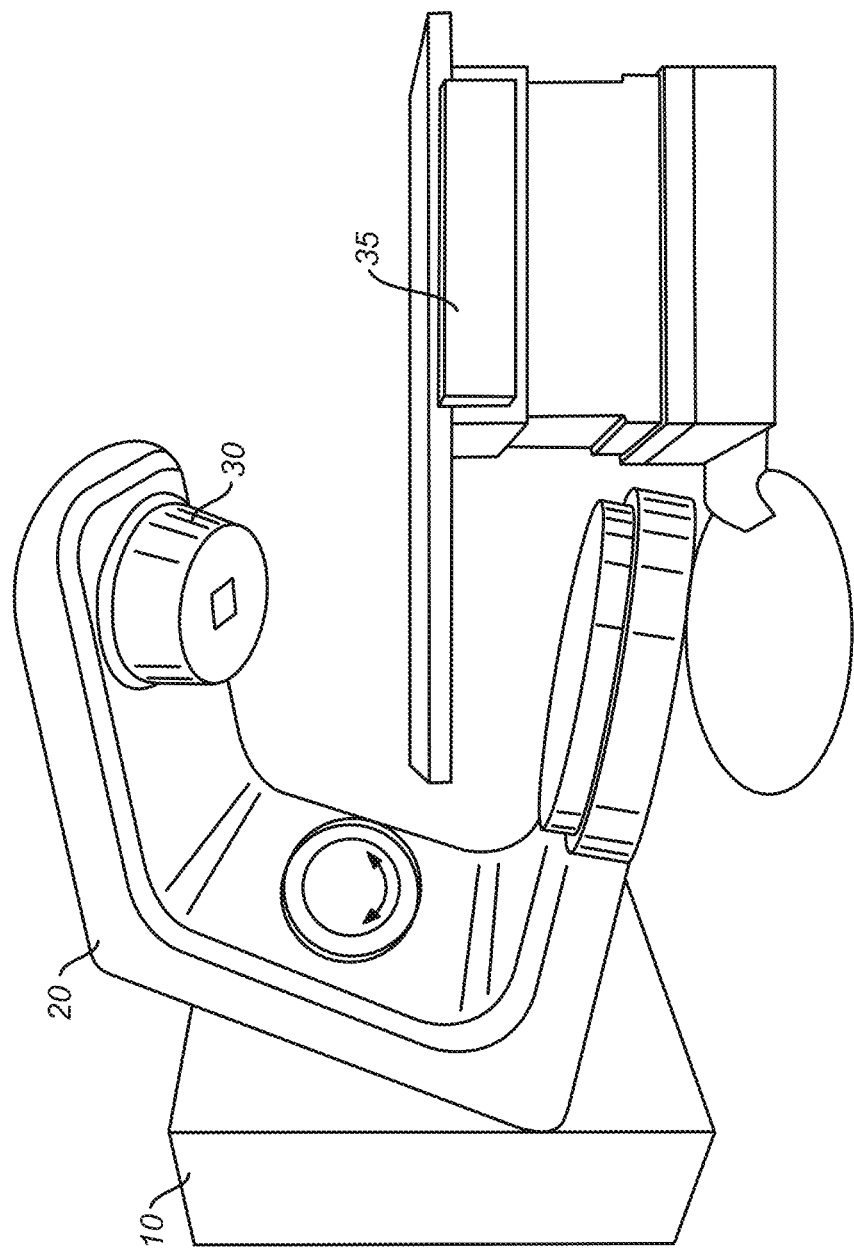
FIG. 1 is a schematic perspective view of a radiation treatment system.
Figure 2:
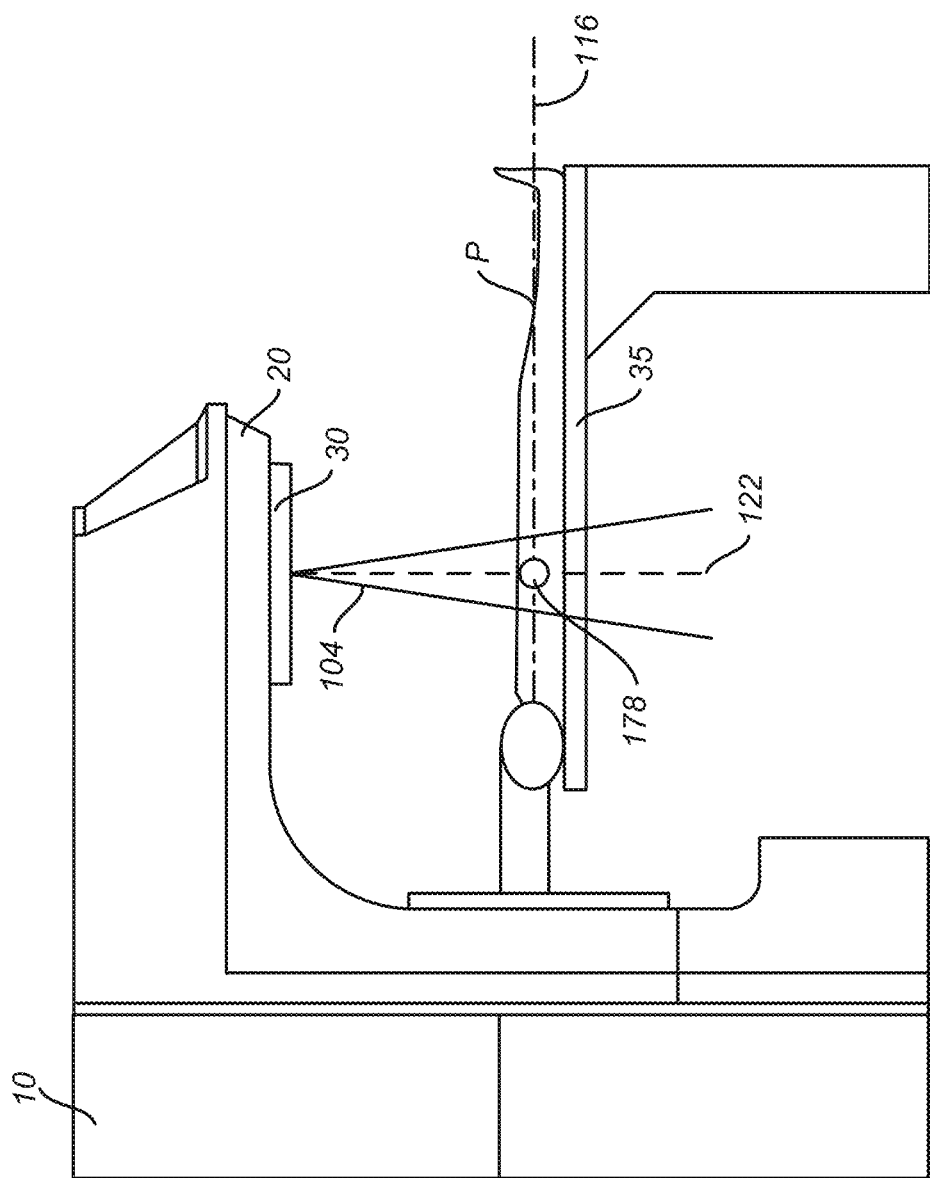
FIG. 2 is a schematic side view of a radiation treatment system.

FIGS. 1 and 2 depict a radiation treatment system of the type that may be used in connection with the present invention. While the inventions herein will be described with reference to C-arm gantries, it will be appreciated by those skilled in the art that the same principles apply to other rotatable gantries such as ring gantries. Referring to FIG. 1, a perspective view of radiation treatment system (in this case a linear accelerator) is shown. Typically, such a system is capable of generating either an electron (particle) beam or an x-ray (photon) beam for use in the radiotherapy treatment of patients on a treatment couch 35. Other radiation treatment systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) that includes control circuitry for controlling the different modes of operation of the accelerator. A high voltage source is provided within the stand or in the gantry, to supply voltage to an electron gun (not shown) positioned on an accelerator guide located in the gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation treatment system of the type that may be used in connection with the present invention is shown. A patient P is shown lying on the treatment couch 35. X-rays formed as described above are emitted from the target in the treatment head 30 in a divergent beam 104. Typically, a patient plane 116, which is perpendicular to the page in FIG. 2, is positioned about one meter from the x-ray source or target, and the axis of the gantry 20 is located on the plane 116, such that the distance between the target and the isocenter 178 remains constant when the gantry 20 is rotated. The isocenter 178 is at the intersection between the patient plane 116 and the central axis of beam 122. A treatment volume to be irradiated is located about the isocenter 178.

Figure 3:
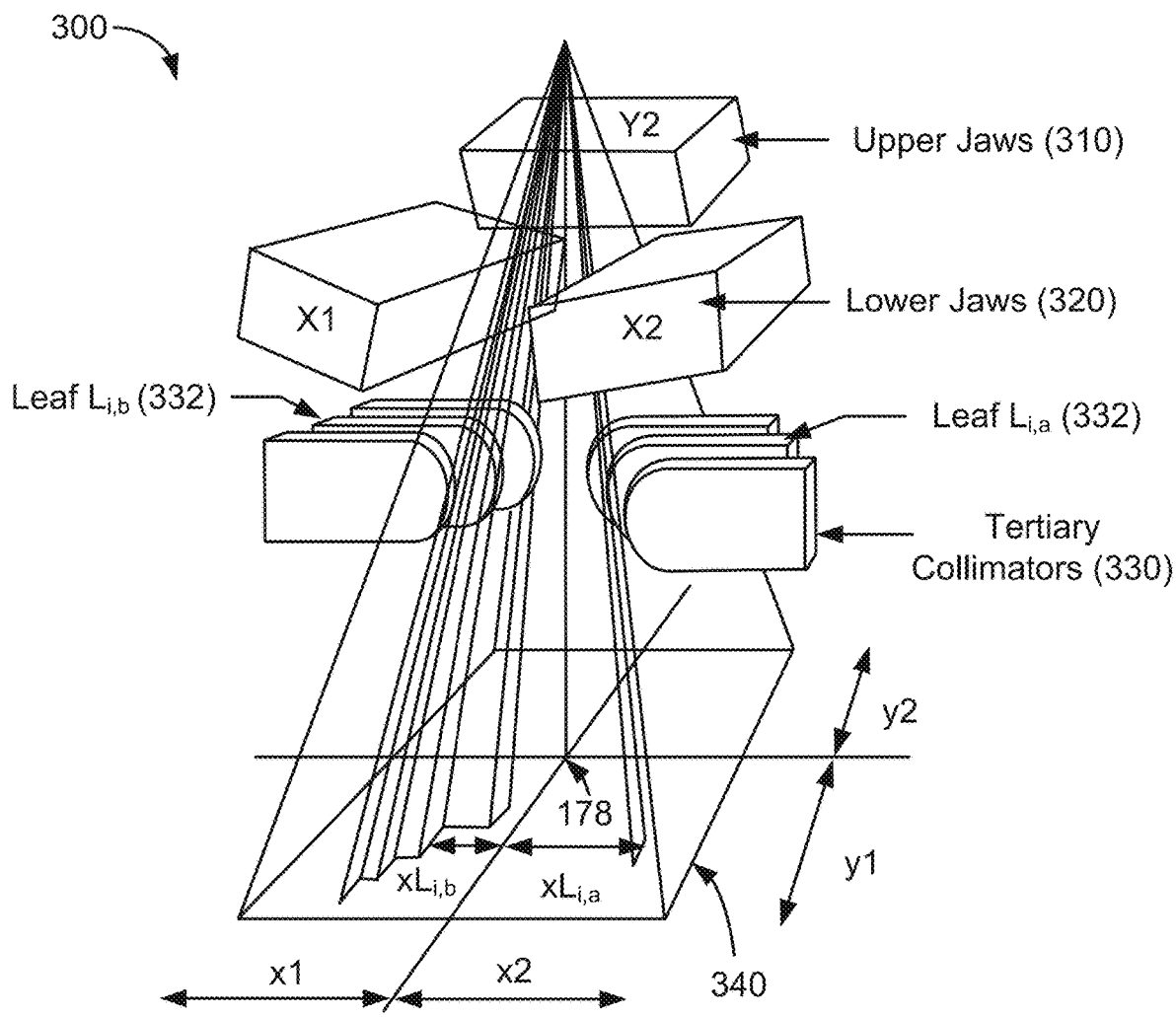
FIG. 3 shows schematically a photon collimation system in a radiation treatment system.

FIG. 3 shows schematically a photon collimation system 300 with upper jaws 310 (i.e., the Y1 and Y2 jaws; the Y1 jaw is omitted for clarity), lower jaws 320 (i.e., the X1 and X2 jaws), and a multi-leaf collimator (MLC) 330. The field dimensions in the plane 340 at the isocenter 178 are indicated. The upper jaws 310, the lower jaws 320, and the leaves 332 of the MLC 330 comprise an x-ray blocking material, and are positioned in the head 30 to define the width of the x-ray beam at the patient plane. Typically, the jaws 310 and 320 are moveable and, when fully open, define a maximum beam of about 40 cm×40 cm at the patient plane 116. The MLC 330 is positioned at the exit of the head 30, to further shape the x-ray beam. Since its introduction in 1990 the MLC has become a standard feature of most radiation treatment systems. An example of a current MLC sold by the assignee of the present invention use up to 120 individually controllable leaves, typically thin slices of tungsten, that can be moved into or out of the x-ray beam under the control of system software.

Figure 4:
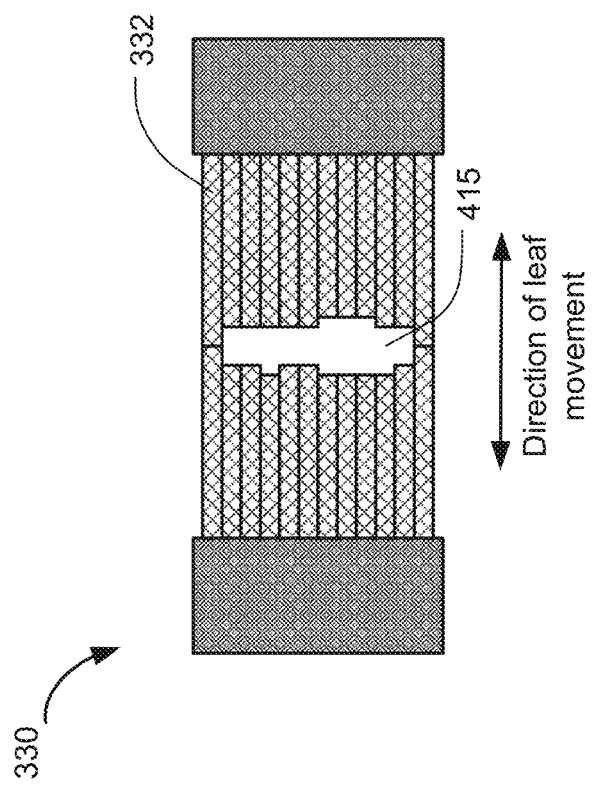
FIG. 4 shows an exemplary multi-leaf collimator (MLC) plane.

FIG. 4 shows an exemplary MLC plane having a plurality of leaves 332, arranged in opposing pairs, and an aperture 415 created by selected leaf movements. Radiation passes through and is shaped by the aperture 415. Thus, the MLC can be used to collimate the x-rays to provide conformal treatment of tumors from various angles ("3D conformal") as well as intensity modulated radiotherapy ("IMRT"), whereby different radiation doses are delivered to different portions of the treatment area. The treatment volume, i.e., the irradiated volume proximate to the isocenter 178 in the path of the x-ray beam, is defined by the jaws 310 and 320, the leaf sequences of the MLC 330, and the collimator angle, i.e., the angle at which the MLC 330 sits in the head 30. Some external radiation treatment systems may include multiple layers of MLCs. The multiple layers of MLCs may be positioned at different planes and at different collimator angles.

Figure 5:
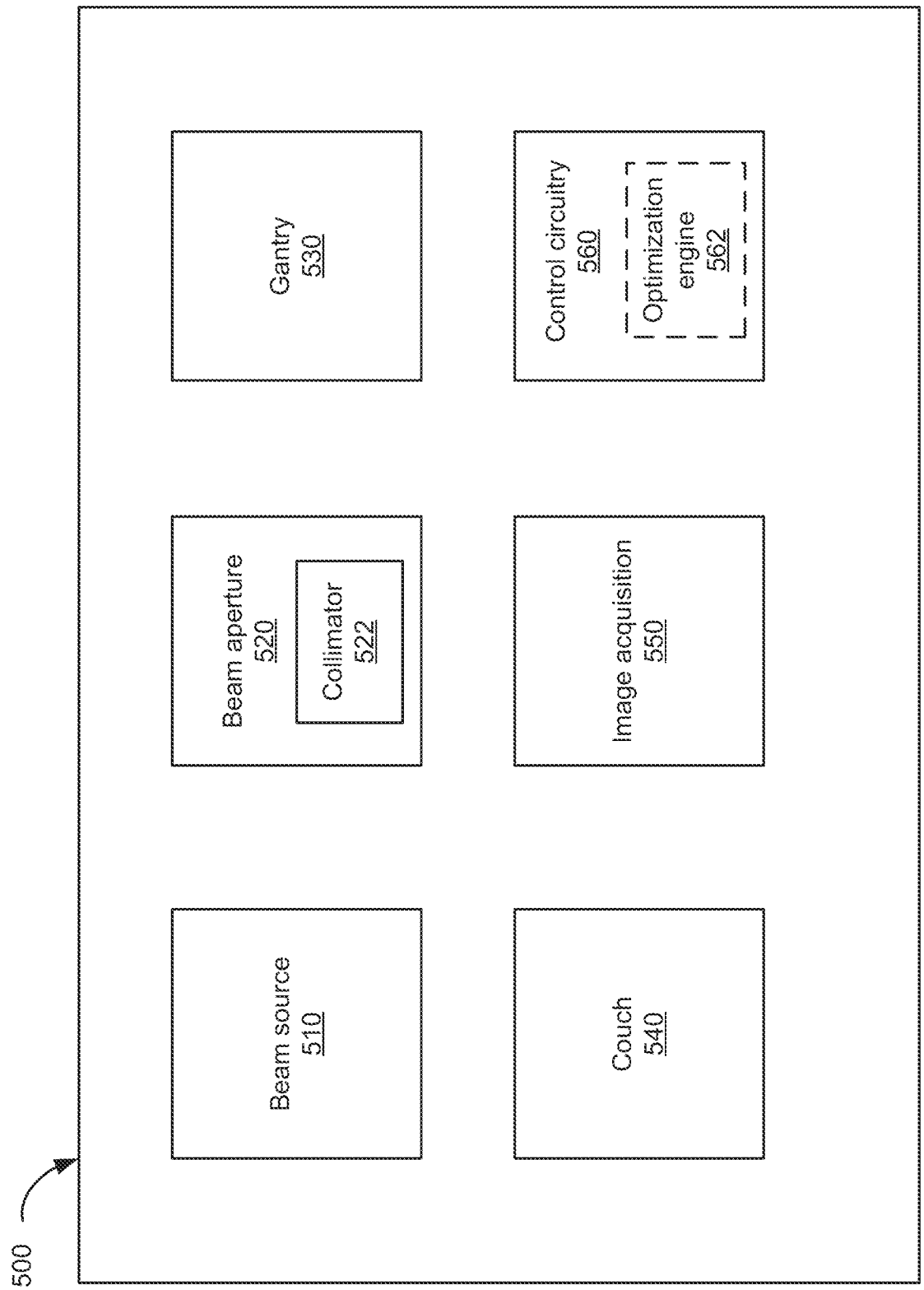
FIG. 5 shows a block diagram of an external-beam radiation treatment system of FIGS. 1 and 2.

FIG. 5 shows a block diagram of an external-beam radiation treatment system 500 of FIGS. 1 and 2. The radiation treatment system 500 includes a beam source 510, a beam aperture 520, a gantry 530, and a couch 540. The beam source 510 is configured to generate a beam of therapeutic radiation. This beam of radiation may include x-rays, particles, and the like. The beam aperture 520 includes an adjustable multi-leave collimator (MLC) 522 for spatially filtering the radiation beam. The couch 540 is configured to support and position a patient. The couch 540 may have six degrees of freedom, namely the translational offsets X, Y, and Z, and the rotation, pitch, and yaw.

The gantry 530 that circles about the couch 540 houses the beam source 510 and the beam aperture 520. The beam source 510 is optionally configured to generate imaging radiation as well as therapeutic radiation. The radiation treatment system 500 may further include an image acquisition system 550 that comprises one or more imaging detectors mounted to the gantry 530.

The radiation treatment system 500 further includes a control circuitry 560 for controlling the operation of the beam source 510, the beam aperture 520, the gantry 530, the couch 540, and the image acquisition system 550. The control circuitry 560 may include hardware, software, and memory for controlling the operation of these various components of the radiation treatment system 500. The control circuitry 560 can comprise a fixed-purpose hard-wired platform or can comprise a partially or wholly-programmable platform. The control circuitry 560 is configured to carry out one or more steps, actions, and other functions described herein. In some embodiments, the control circuitry 560 may include a memory for receiving and storing a radiation treatment plan that defines the control points of one or more treatment fields. The control circuitry 560 may then send control signals to the various components of the radiation treatment system 500, such as the beam source 510, the beam aperture 520, the gantry 530, and the couch 540, to execute the radiation treatment plan. In some embodiments, the control circuitry 560 may include an optimization engine 562 configured for determining a radiation treatment plan. In some other embodiments, the control circuitry 560 may not include an optimization engine. In those cases, a radiation treatment plan may be determined by an optimization engine in a separate computer system, and the radiation treatment plan is then transmitted to the control circuitry 560 of the radiation treatment system 500 for execution.

II. Radiation Treatment Planning

Radiation therapy is generally implemented in accordance with a radiation treatment plan that typically takes into account the desired dose of radiation that is prescribed to be delivered to the tumor, as well as other constraints on dose in the surrounding tissues that depend on the tissue type. Various techniques for developing radiation treatment plans may be used. Preferably, the computer system used to develop the radiation treatment plan provides an output that can be used to control the radiation treatment system, including the control points and the MLC leaf movements. Typically, the desired dose prescribed in a radiation treatment plan is delivered over several sessions, called fractions.

Several techniques have been developed to create radiation treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans, such as volumetric modulated arc therapy (VMAT), where the one or more external treatment coordinates, such as the isocenter location, gantry angle, couch angles, and couch offsets, are in motion while irradiating the target volume. Heretofore, radiation oncologists or other medical professionals, such as medical physicists and dosimetrists, have used one of the available algorithms to develop and optimize a radiation treatment plan.

Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk (OAR) that can only receive a much lower, maximum prescribed amount of radiation. This volumetric information along with the prescribed dose limits and similar objectives set by the medical professionals are the basis for calculating an optimized dose distribution, also referred to as fluence map, which in turn is the basis for determining a radiation treatment plan. The volumetric information may, for example, be reduced to an objective function or a single figure of merit that accounts for the relative importance of various tradeoffs inherent in a radiation treatment plan, along with constraints that must be met for the radiation treatment plan to be medically acceptable or physically possible.

III. Beam's Eye View (BEV) Sectioning in Treatment Geometry Optimization

State-of-the-art techniques for optimizing treatment trajectories (e.g., VMAT trajectories) in external beam radiotherapy involve dosimetric characterization of candidate directions of incidence. (See e.g., Christopher Barry Locke and Karl Kenneth Bush, Trajectory Optimization In Radiotherapy Using Sectioning (referred to herein as TORUS), *Medical Physics,* 2017, and U.S. patent application Ser. Nos. 16/235,205 and 16/235,211) The goal of the optimizations may be to ascertain which directions of incidence in the permissible delivery coordinate space are more suited for treating the patient, considering the dose response of both planning target volumes (PTVs) and organs at risk (OARs) within the patient.

A. Delivery Coordinate Space (DCS)

The delivery coordinate space (DCS) is a set of all allowable coordinates that parameterize the delivery device's configuration, truncated to avoid collisions (e.g., machine-to-machine collisions and machine-to-patient collisions). For a C-arm linear accelerator with fixed isocenter, points in a delivery coordinate space may be defined as tuples of the form ($\theta_{gantry}$, $\theta_{couch}$), where $\theta_{gantry}$ is the gantry angle, and $\theta_{couch}$ is the couch angle. The DCS may be discretized into a 2D mesh defined by a set of vertices (e.g., each vertex having associated gantry angle and couch angle values), edges, and triangle faces. Thus, the DCS $\mathbb{D}$ may be represented by a simplicial complex (mesh) defined by:

$N_1^{\mathbb{D}}$ vertices: tuples of ($\theta_{gantry}$, $\theta_{couch}$) angles;
$N_2^{\mathbb{D}}$ edges: ordered pair of start and end vertices; and
$N_3^{\mathbb{D}}$ triangles: ordered list of 3 vertex indices.

Figure 6:
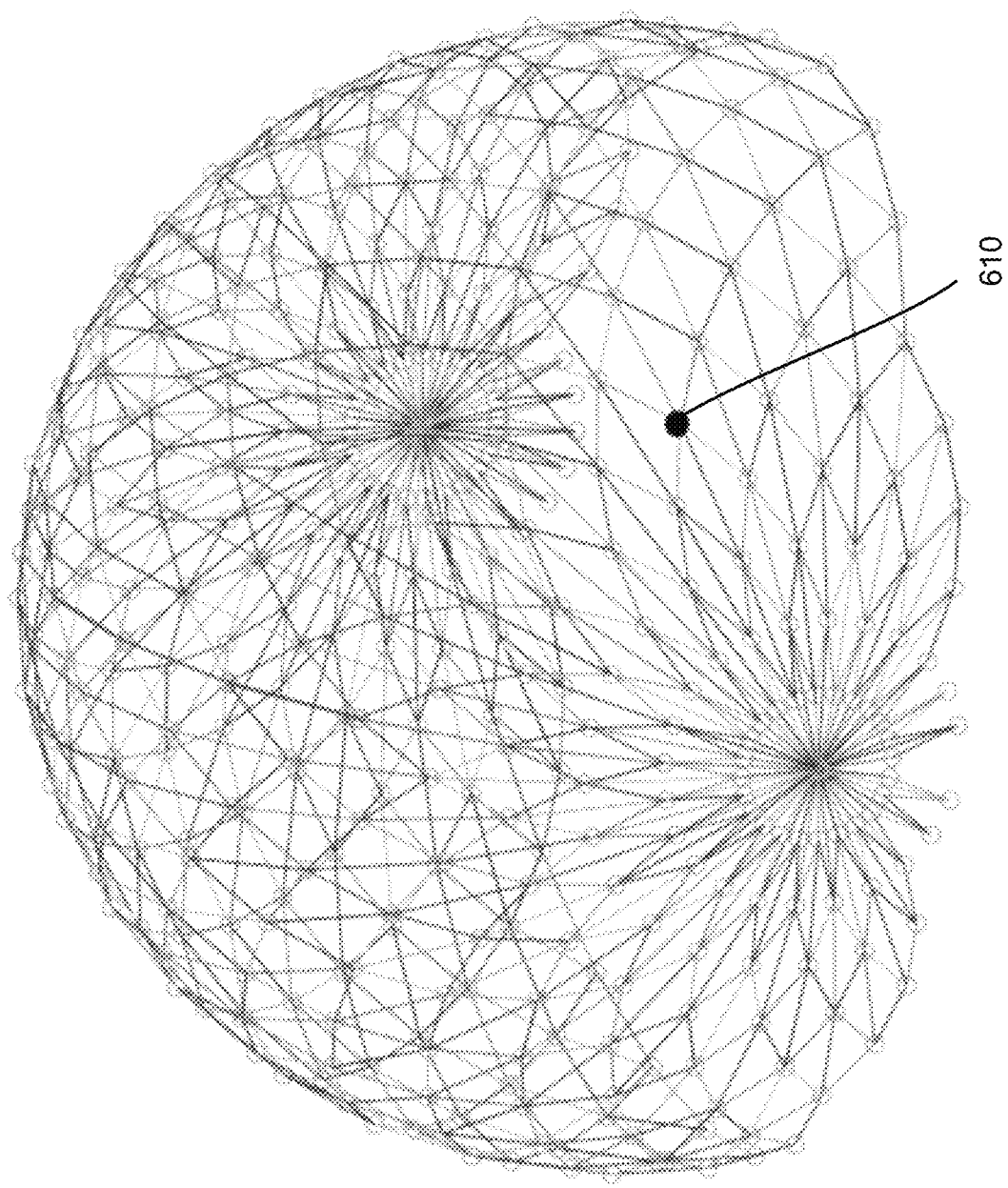
FIG. 6 shows a representation of a delivery coordinate space (DCS) truncated to avoid collisions, where each point $(\theta_{gantry}, \theta_{couch})$ is transformed to the physical three-dimensional (3D) location of a treatment head.

FIG. 6 shows a representation of a DCS as a 3D mesh, where each point 610 ($\theta_{gantry}$, $\theta_{couch}$) is transformed to the physical three-dimensional (3D) location of the treatment head, and the space is truncated to avoid collisions.

B. BEV Sectioning

Christopher Barry Locke and Karl Kenneth Bush, Trajectory Optimization In Radiotherapy Using Sectioning (referred to herein as TORUS), *Medical Physics*, 2017 discusses a method of trajectory optimization in radiotherapy using sectioning. Dosimetry experience in radiation treatment planning has shown that BEV offers a valuable tool in determining the geometrical setup for both dynamic gantry treatment (e.g., VMAT) and static gantry treatment (e.g., IMRT).

For a source position $r_v^s$ corresponding to vertex v in the 3D DCS, a BEV plane (also referred to as an isocenter plane) may be defined as a plane perpendicular to the vector $r_v^s - r_v^{ISO}$ and including the isocenter $r_v^{ISO}$. A BEV plane may be discretized into a 2D array of $N_x \times N_y$ pixels, with each pixel on this 2D grid representing a single beamlet.

To probe all possible beamlets, the intensity of each beamlet may be set to unity, and a 3D dose response to each beamlet may be evaluated. The 3D dose may be processed to determine dose statistics to each region of interest (ROI) for each beamlet. The ROIs may include, for example, planning target volumes (PTVs) and organs at risk (OARs). If the dose for a beamlet at pixel ($n_x$, $n_y$) in the BEV plane given by delivery coordinate vertex $n_v$ to the ROI with index $n_{ROI}$ at position (x, y, z) is given by $D_{n_v,n_x,n_y,n_{ROI}}(x,y,z)$, then the volume integrated dose for the ROI with index $n_{ROI}$ may be evaluated as, $$\mathcal{D}_{n_v,n_x,n_y,n_{ROI}} = \int dx\, dy\, dz\, D_{n_v,n_x,n_y,n_{ROI}}(x,y,z) \quad (1)$$

If there are $N_{ROI}$ regions of interest, then the BEV dose bundle section $\mathcal{D}$ is a 4D array of size ($N_1^{\mathbb{D}}$, $N_x$, $N_y$, $N_{ROI}$) containing the volume integrated dose values for each ROI from each beamlet.

In some embodiments, a BEV score bundle section $\mathcal{S}$ may be defined as a contraction of the 4D BEV dose bundle section $\mathcal{D}$ into a 3D matrix of size ($N_1^{\mathbb{D}}$, $N_x$, $N_y$), where the values are a measure of the "goodness" of beamlets based on the ROI dosimetrics. In some embodiments, the "goodness" score may be evaluated as a linear combination of the doses to each ROI, $$\mathcal{S}_{n_v,n_x,n_y} = \sum_{n_{ROI}=1}^{N_{ROI}} w_{n_{ROI}} \mathcal{D}_{n_v,n_x,n_y,n_{ROI}} \quad (2)$$

The coefficients $w_{n_{ROI}}$ may be set by users. For example, the values of the coefficients may be set to −0.2 for body, between −1 and −10 for an OAR (e.g., critical organs may be given more negative weights), and between zero and +1 for a PTV.

C. BEV Regions and BEV Region Connectivity Manifold

A BEV region connectivity manifold may be constructed in two steps. First, information contained in the BEV score bundle sections may be considered and a binary selection procedure is applied to determine if a given pixel (beamlet) is a "good" or "bad" candidate for treatment. For each BEV plane, a set of "good" beamlets form regions. Each region includes a set of contiguous pixels in the BEV plane, and represent potential open aperture candidates for use in the optimization. Next, how the regions connect to other regions in neighboring vertices may be determined. The resulting structure, comprised of regions and their connections, forms a BEV region connectivity manifold.

1. BEV Region Score

In some embodiments, a beamlet may be deemed a "good" candidate if it intersects a PTV and its score S is above a certain threshold $\mathcal{D}_{threshold}$. Choosing an appropriate threshold may be a non-trivial task and can be case specific. For example, beamlets treating a superficial target with very little body or OAR in the way (e.g. a prone breast irradiation) may have a different threshold than a deep seated target (e.g., in a prostate treatment) in which the best possible plan may still treat through healthy tissue to a substantial depth.

According to some embodiments, a region score $\mathcal{R}_{n_v,n_x,n_y} \in (-\infty, 1]$ may be used to define regions, where the potentially "good" beamlets are defined to have $\mathcal{D} > 0$, $$\mathcal{R}_{n_v,n_x,n_y} = \begin{cases} -\infty & \text{if } \nexists\, n_{ROI} \in N_{PTV} \ni \mathcal{D}_{n_v,n_x,n_y,n_{ROI}} > 0 \\ \dfrac{\mathcal{S}_{n_v,n_x,n_y} - \mathcal{S}_{threshold}}{\max(\mathcal{S}) - \mathcal{S}_{threshold}} & \text{otherwise} \end{cases}, \quad (3)$$

where $N_{PTV}$ is the set of ROI indices for PTV regions of interest. Thus, a beamlet may be deemed a "good" candidate if it intersects the PTV and its score is above some threshold $\mathcal{S}_{threshold}$. The region score $\mathcal{D}$ may classify beamlets into regions, and may also act as a normalized score for the goodness of beamlets (e.g., the maximum region score being unity).

2. Score Threshold Determination

According to some embodiments, the score threshold $\mathcal{S}_{threshold}$ may be automatically determined using histograms of the BEV fiber bundle sections, in the spirit of dose-volume histograms (DVHs). Given a section $\mathcal{F}_n$, where n is an index in some set $\mathcal{N}$, and a subset of indices under consideration $\mathcal{N}_h$, the associated BEV fiber bundle section histogram may be defined as follows:

Determine the maximum and minimum values of the set $\{\mathcal{F}_n | n \in \mathcal{N}_h\}$, $F_{max}$ and $F_{min}$.

Create $N_{bins}$ that range from $F_{min}$ to $F_{max}$, and initialize each to 0. These may be referred to as differential histogram bins and are denoted $\partial B^{\mathcal{F}}_{n_{bins}}$ for each bin index $n_{bin}$.

Loop through each $n \in \mathcal{N}_h$ and increment the bin that corresponds to the value $\mathcal{F}_n$ by 1.

The integrated histogram bins may be defined as $B^{\mathcal{F}}_{n_{bin}} = \sum_{n=n_{bin}}^{N_{bins}-1} \partial B^{\mathcal{F}}_n$.

Normalize the differential and integrated histogram bins to have maximum value of 1.

Figure 7:
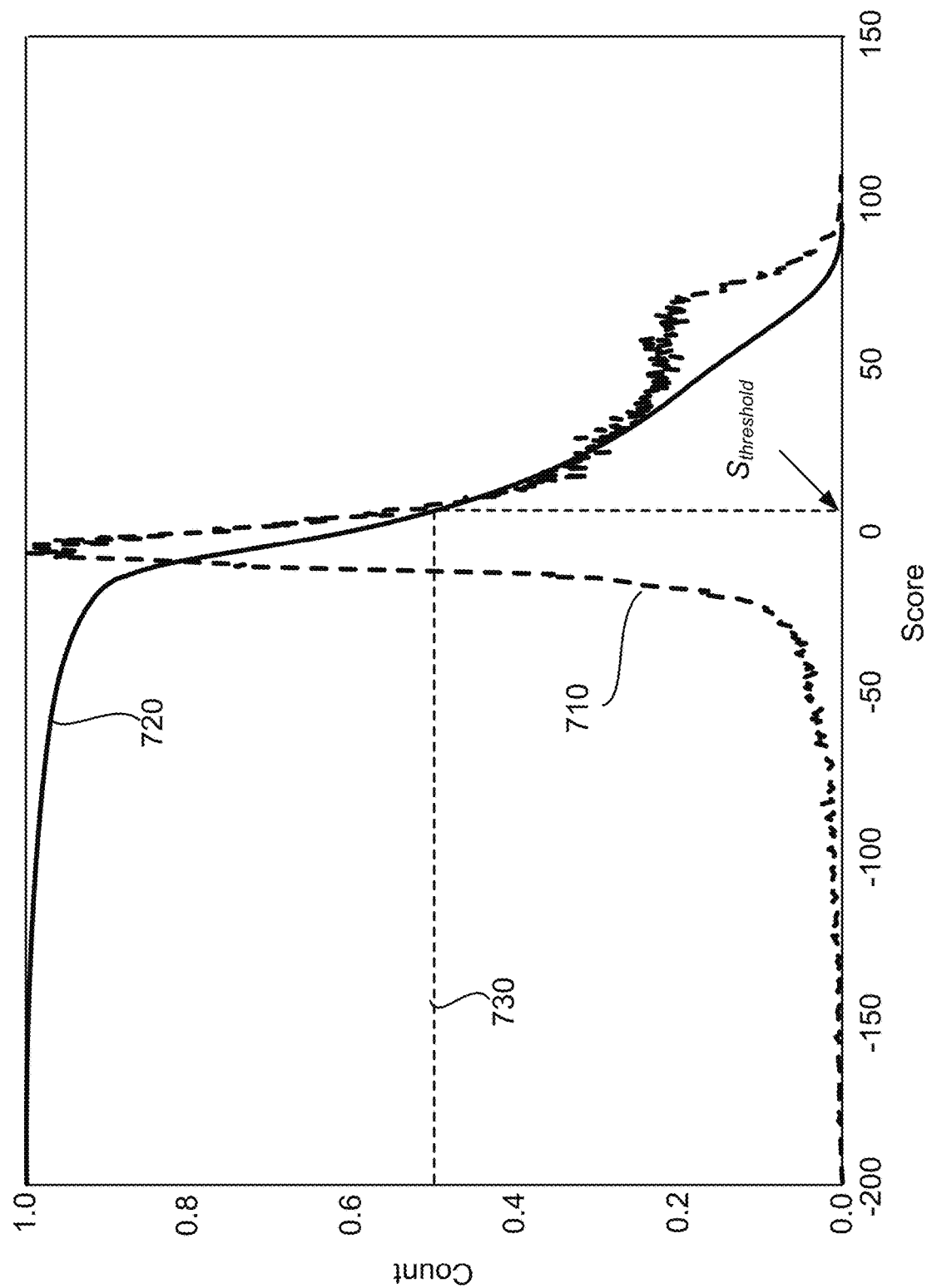
FIG. 7 shows examples of a differential beam's eye view (BEV) fiber bundle section histogram and an integrated BEV fiber bundle section histogram according to some embodiments.

FIG. 7 shows examples of a differential BEV fiber bundle section histogram 710 (dashed line) and an integrated BEV fiber bundle section histogram 720 (solid line) according to some embodiments. The dotted lines 730 meet at the integrated histogram curve 720 and may have a vertical height to horizontal length ratio of 0.7. Their intersection with the abscissa may give the score threshold $S_{threshold}$.

Using this definition, one may define the BEV PTV dose histogram from the BEV fiber bundle section $\mathcal{D}_{n_v,n_x,n_y}^{PTV} = \Sigma_{n_{ROI} \in N_{PTV}} \mathcal{D}_{n_v,n_x,n_y,n_{ROI}}$ (the BEV fiber bundle section representing the total PTV dose only). These histograms may be denoted as $\partial B^D$ and $B^D$. In some embodiments, this histogram may be used to determine a temporary PTV dose threshold so that only the scores of beamlets with the highest 50% of PTV doses are considered. This threshold value may be denoted $D_{threshold}^{PTV}$ and is the dose of the integrated histogram bin of $B^D$ with height 0.5.

Next, a BEV score histogram, for determining a score threshold, may be calculated using the BEV score bundle section $S$, restricted to the indices $\{n | \mathcal{D}_{n_v,n_x,n_y}^{PTV} > D_{threshold}^{PTV}\}$. These histograms may be denoted as $\partial B^S$ and $B^S$. The ratio of vertical height to horizontal height of a point on the integrated histogram curve (e.g., the ratio of sides of the rectangle formed by the axes and the dotted lines 730 shown in FIG. 7) is:

$$\text{ratio}(S) = B^S(S) \cdot \frac{S_{max} - S_{min}}{S - S_{min}}, \quad (4)$$

where $B^S(S)$ denotes the integrated histogram height at score value S (i.e. where $n_{bin}$ is the corresponding bin index). This ratio varies monotonically from $+\infty$ for $S=S_{min}$ to 0 for $S=S_{max}$ where $B^S=0$. The score threshold $S_{threshold}$ may be defined to be the value such that ratio($S_{threshold}$)=0.7.

It should be understood that the score threshold determination method described above is only an example. Other determination methods may be used according to other embodiments.

Figure 8B:
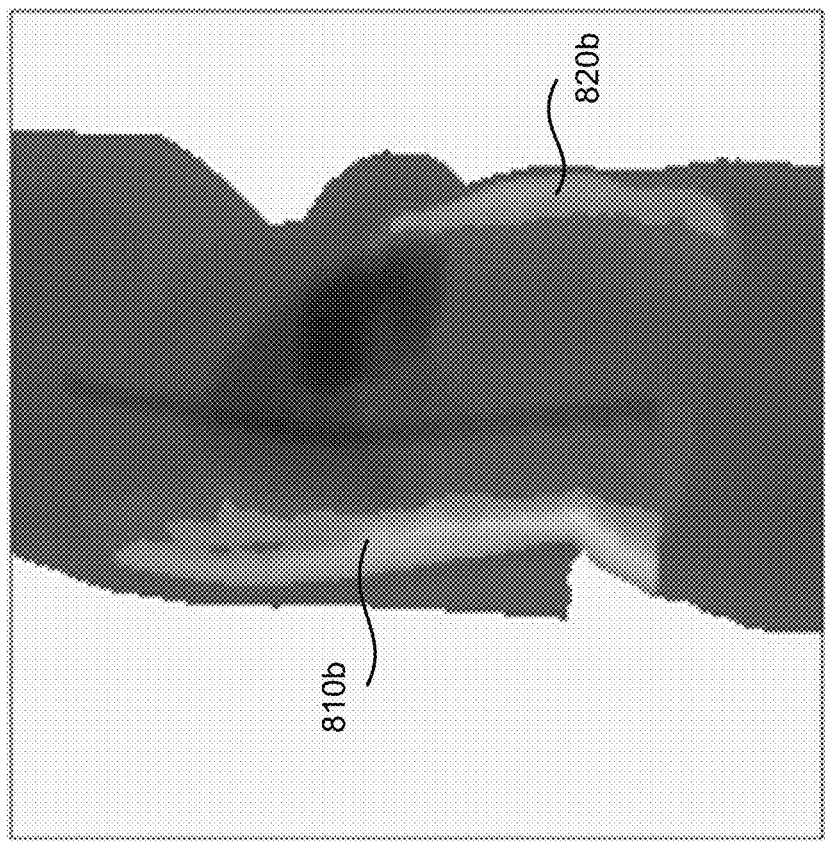
FIGS. 8A and 8B show exemplary images of BEV scores for two adjacent delivery coordinate vertices for a chest wall treatment, respectfully, according to some embodiments.
Figure 8A:
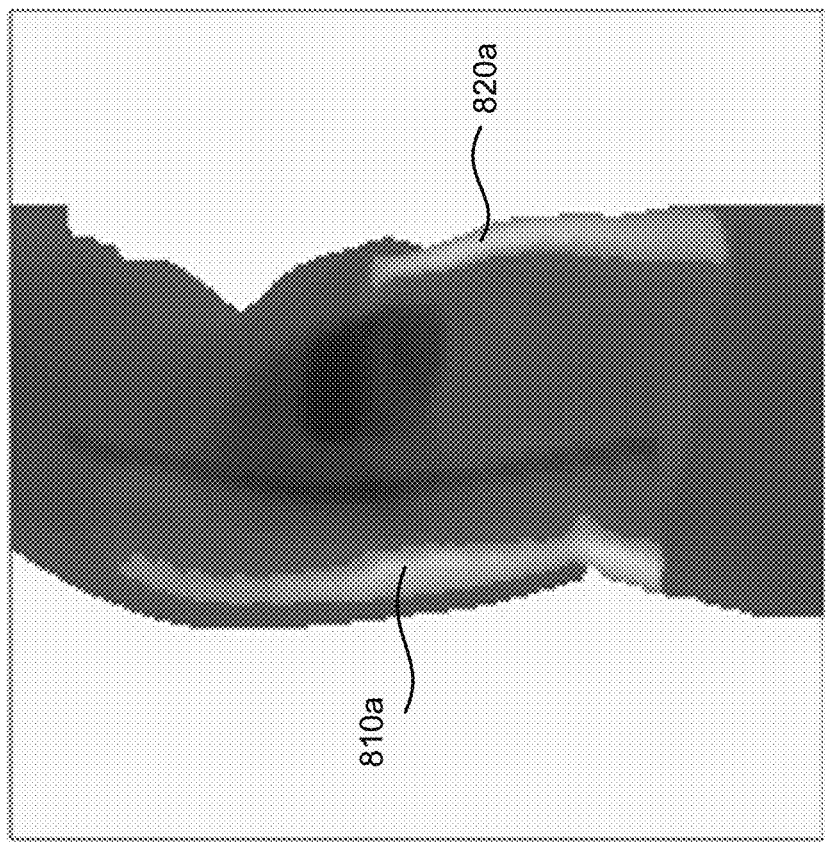

FIGS. 8A and 8B show exemplary images of BEV scores for two adjacent delivery coordinate vertices for a chest wall treatment. Darker shades represent lower score values and brighter shades represent higher score values. Gold colors represent beamlets that pass the region selection criterion, and thus are considered as BEV regions. In this example, from the BEV perspective, there are two disconnected BEV regions 810a and 820a in the BEV shown in FIG. 8A, and two disconnected BEV regions 810b and 820b in the BEV shown in FIG. 8B.

3. BEV Region Connectivity Manifold

Proximity or overlap of regions at neighboring vertices in the delivery coordinate space may be examined in order to form a complete BEV region connectivity manifold. The BEV region connectivity manifold contains information on how candidate target regions in the BEV change, appear, split, and vanish as one moves in the delivery coordinate space in all directions. For instance, in the example shown in FIGS. 8A and 8B, overlaying the two images of the two adjacent delivery coordinate vertices on each other, the regions 810a and 810b on the left may overlap with each other, and the regions 820a and 820b on the right may overlap with each other. Thus, it may be inferred that the regions 810a and 810b are connected, and the regions 820a and 820b are connected when moving along this edge in delivery coordinate space. The set of all regions and all connections along delivery coordinate space edges form the BEV region connectivity manifold. Moreover, each BEV region connectivity manifold maintains, for each region it contains, a mapping between the region and the subvolumes (that is, voxels in the computer model) of the planning target volumes (PTVs), which are subjected to radiation if the patient body is irradiated from the vertex in which the region resides through an aperture equal to the shape of the region.

The information contained in the BEV regions and the BEV region connectivity manifold may be used to generate optimized trajectories or field geometries in a radiation treatment. For example, as discussed below and in Christopher Barry Locke and Karl Kenneth Bush, Trajectory Optimization In Radiotherapy Using Sectioning (TORUS). Medical Physics, 2017, methods of trajectory optimization may use a BEV region connectivity manifold as a scaffold to guide an optimizer, which may make the search space small enough to apply graph search techniques with efficient computation times.

IV. Dose Calculations

As discussed above, to determine BEV regions and BEV region connectivity manifold, it may be necessary to evaluate dose response $\mathcal{D}_{n_v,n_x,n_y,n_{ROI}}$ as expressed in Equation (1), for each point in the 4D space coordinates ($n_v$, $n_x$, $n_y$, $n_{ROI}$). The dose response may be evaluated by solving the Boltzmann transport equations. Two approaches of solving the Boltzmann transport equations: the forward transport approach and the adjoint transport approach, are discussed below. The adjoint transport approach may be more efficient computationally, as discussed below.

A. Forward Transport Solutions

Evaluating dose response in a forward transport manner may involve solving the following forward transport equations (see John McGhee, et. al., "AcurosXB Technical Manual," Varian Medical Systems, (2017)):

$$\hat{\Omega} \cdot \nabla \Psi^\gamma + \sigma_t^\gamma \Psi^\gamma = S^{\gamma\gamma} \Psi^\gamma + S^{\gamma e} \Psi^\gamma + q^\gamma, r \in V_{pat}, \quad (5)$$

$$\hat{\Omega} \cdot \nabla \Psi^e + \sigma_t^e \Psi^e = S^{ee} \Psi^e + S^{\gamma e} \Psi^\gamma, r \in V_{pat}, \quad (6)$$

where $\Psi^\gamma$ is the angular photon fluence, $\Psi^e$ is the angular electron fluence, $\sigma_t^\gamma$ is the photon total cross section, $\sigma_t^e$ is the total electron cross section, and $S^{\gamma\gamma}$, $S^{\gamma e}$, and $S^{ee}$ are the truncated spherical harmonics source operators. $q^\gamma$ is a point source located at the position $r_v^s$ corresponding to vertex v. The dependence of $\Psi$ on position r, space angle $\hat{\Omega}$, and energy E has been suppressed for clarity. The angular representation for $q^\gamma$ may be defined by a plane of $N_x \times N_y$ pixels centered at the isocenter, where the angle is defined by a vector from the point source position $r_v^s$ to the center of each pixel ($x_{v,i}$, $y_{v,i}$). For the purposes of this disclosure, a fluence flow (or intensity) value of unity may be applied through each pixel. Once Equations (5) and (6) are consecutively solved with Equation (5) being solved first, then the dose to a region of interest (ROI) may be evaluated as, $$D_{ROI} = \langle \sigma_{ED}^e, \Psi^e \rangle \equiv \int_0^\infty \int_{4\pi} \sigma_{ED} \Psi^e d\hat{\Omega} dE, r \in V_{ROI}. \quad (7)$$

Equations (5) and (6) may be discretized by discontinuous finite element (DFEM) in space, multigroup in energy, and discrete ordinates in angle, in conjunction with the first scattered distributed source (FSDS) approach for the point source of photons (see John McGhee, et. al., "AcurosXB Technical Manual," Varian Medical Systems, (2017)).

The task of evaluating the dose response using the forward transport approach can be computationally expensive. As an example, in the context of a C-arm linear accelerator, assuming that the DCS has resolution of 15 degrees in gantry angle and 7.5 degrees in couch angle, the number of vertices may equal to $N_v$=(360 deg)/(15 deg)×(180 deg)/(7.5 deg)

≈580 vertices (i.e., candidate directions of incidence). Assuming an isocenter plane size of 40 cm×40 cm and a pixel size of 2.5 mm×2.5 mm, the number of pixels in each isocenter plane may be equal to $N=N_x \times N_y=(400/2.5)^2=25600$. Therefore, in order to characterize the dose for each beamlet separately, the total number of dose calculations needed may amount to about $N \times N_v=25600 \times 580 \approx 15 \times 10^6$. Thus, the required amount of computation can be very time consuming. For example, the computation may take several days, which may render it unsuitable for real-time treatment optimization in clinical settings.

B. Adjoint Transport Approach

According to some embodiments, the adjoint formulation of the Boltzmann transport equation may be used for efficient, parallel GPU-compatible evaluation of the dose matrices. Denoting $\tilde{\Psi}^\gamma$ as the adjoint gamma fluence and $\tilde{\Psi}^e$ as the adjoint electron fluence, the adjoint transport equations may be expressed as, $$-\vec{\Omega} \cdot \nabla \tilde{\Psi}^e + \sigma_t^e \tilde{\Psi}^e = \tilde{S}^{ee} \tilde{\Psi}^e + \tilde{S}^{e\gamma} \tilde{\Psi}^e + \tilde{q}^e, r \in V_{pat}, \qquad (8)$$

$$-\vec{\Omega} \cdot \nabla \tilde{\Psi}^\gamma + \sigma_t^\gamma \tilde{\Psi}^\gamma = \tilde{S}^{\gamma\gamma} \tilde{\Psi}^\gamma + \tilde{S}^{e\gamma} \tilde{\Psi}^e, r \in V_{pat}, \qquad (9)$$

where, $$\tilde{q}^e = \sigma_{ED}, r \in V_{ROI}. \qquad (10)$$

Equations (8) and (9) may be solved consecutively. To obtain the adjoint photon fluence $\tilde{\Psi}\gamma$ at the forward source position $r_v^s$, the "last collided fluence approach" may be used. Let us assume that the aperture around the pixel is small enough that only one characteristic ray needs to be considered. This characteristic ray may start at $r_v^s$, go through the center of the source fluence pixel $(n_x, n_y)_v$, and then into the patient (along this defined characteristic line), and through the patient and continuing until it exits the patient. A path, s, may be defined to be this characteristic line starting at $s_l=r_v^s$ and ending at $s_u$, where it exits the patient. The "last collided fluence approach" uses integral transport theory to reconstruct the adjoint photon fluence $\tilde{\Psi}^\gamma$ at any arbitrary position in space $r_v^s$, (see E. E. Lewis and W. F. Miller, Computational Methods of Neutron Transport, American Nuclear Society (1993)). The adjoint photon fluence $\tilde{\Psi}^\gamma$ at $r_v^s$ may be obtained as, $$\tilde{\Psi}^\gamma(r_v^s) = -\int_{s_u}^{\infty} sl(\tilde{S}^{\gamma\gamma} \tilde{\Psi}^\gamma + \tilde{S}^{e\gamma} \tilde{\Psi}^\gamma) e^{-\sigma_t s} ds. \qquad (11)$$

In the adjoint transport approach, the dose to a region of interest (ROI), from a unit fluence of photons through one pixel $(n_x, n_y)_v$ on the point source plane and where the photons originate from a single position of source vertex v, may be evaluated as, $$D_{ROI} = \langle q^\gamma, \tilde{\Psi}^\gamma \rangle = \int_0^\infty \int_{4\pi} q^\gamma \tilde{\Psi}^\gamma d\vec{\Omega} dE, r=r_v^s. \qquad (12)$$

Note that, for forward transport calculations, $D_{ROI}$ is evaluated over the volume of the region of interest. For adjoint transport calculations, $D_{ROI}$ is evaluated at the position of the forward point source, $r_v^s$.

The adjoint transport approach may afford more efficient dose evaluations as compared to the forward transport approach. As discussed above, in the forward transport approach, in order to evaluate the dose from a unit fluence through each pixel location for each vertex v of the set of all vertices $\{v_j\}_{j=1}^{N_v}$, $N_x \times N_y \times N_v \times N_{ROI}$ number of forward computations may be needed with full patient mesh transport solves of Equations (5) and (6), which can be very expensive computationally. In contrast, in the adjoint approach, only $N_{ROI}$ adjoint transport solves of Equations (8) and (9) may be needed, along with $N_x \times N_y \times N_v$ ray traces to solve Equation (11). Since Equation (11) can be evaluated independently for a set of vertices in a DCS, the computations can be carried out in parallel. Therefore, the number of expensive transport solves may be reduced by several orders of magnitude in the adjoint transport approach as compared to the forward transport approach. A ray trace solve may take only a small fraction of the CPU time of a transport solve. Thus, the reduction in CPU time may be on the order of several orders of magnitude as compared to that using the forward transport approach. As a result, the dose evaluations may be performed in a relatively short time (e.g., in a few minutes to a few tens of minutes), making it suitable for real-time treatment optimization in clinical settings.

C. Dose Evaluations for Multiple Energy Modes

For external beam radiation treatment, various voltages ranging from 4 MV to 25 MV may be used for the radiation source (e.g., the voltage supplied to a linear accelerator in a treatment head). For each voltage, there is an energy spectrum of photons (e.g., X-rays) associated with it. The maximum energy for each voltage may correspond approximately to the voltage value. For example, for a 6 MV voltage, the maximum energy of the photons may be about 6 MeV.

For existing dose evaluation algorithms using the forward transport approach, each voltage may require a separate computation of a complete transport. Since transport solves for a single energy in the forward transport approach are already very expensive computationally, the task may be even more formidable if multiple energies need to be considered.

According to some embodiments, multiple candidate energy modes may be considered in a trajectory optimization or beam angle optimization using the the adjoint transport approach to evaluate dose metrics. In the adjoint transport approach, if Equations (8) and (9) are solved for the maximum energy possible (e.g., 25 MeV), then any voltage that is less than or equal to 25 MV may be computed without a separate transport solve. This is because, if $\tilde{\Psi}^\gamma$ is known for all energies up to the maximum energy, any forward beam source spectra, $q^\gamma$, may be used in Equation (12) to obtain $D_{ROI}$. Thus, $D_{ROI}$ can be evaluated for any energy less than or equal to the maximum energy.

V. Trajectory Optimization Using Adjoint Transport for Dose

According to some embodiments, trajectory optimization uses the adjoint transport approach to efficiently evaluate dose response of each region of interest (ROI), for a given direction of incidence (e.g., at vertex $n_v$) in the DCS, to each beamlet at a respective pixel $(n_x, n_y)$ of a corresponding BEV plane, as expressed in Equation (12). In some embodiments, a BEV score for each pixel, $\mathcal{S}_{n_v,n_x,n_y}$, may be evaluated as a weighted linear combination of the doses to the $N_{ROI}$ regions of interest according to Equation (2). BEV regions and a BEV region connectivity manifold may be determined based on the BEV scores, e.g., as described above in Section III. The information contained in BEV regions and a BEV region connectivity manifold may be used to generate optimized trajectories or optimized field geometries in a radiation treatment, as discussed in more detail below).

Christopher Barry Locke and Karl Kenneth Bush, Trajectory Optimization In Radiotherapy Using Sectioning, Medical Physics, 2017, discusses trajectory optimization in radiotherapy using sectioning (referred to herein as TORUS). The TORUS methods use the the BEV regions and BEV region connectivity manifold as a guide to generate heuristically optimal radiotherapy trajectories automatically for efficient delivery of high quality VMAT treatment plans. TORUS uses an optimization graph on top of a delivery coordinate space to generate optimal treatment trajectories using a dual-metric optimization. Nodes in the optimization graph may represent individual control points, and trajectories may be defined as paths that minimize a min-distance metric, while a max-distance metric may act as a measure of goodness to select optimal trajectories.

A. PTV Angular Flux

One of the concepts used in the TORUS methods is PTV angular flux, which relates to novelty of three-dimensional (3D) direction vectors of incident beamlets for a given point in a PTV. Inverse dose optimization may perform better with more angles from which radiation beams enter the patient. The reason for this may be twofold. First, by entering the patient from many directions, the ratio of overlapping dose within the PTV to surrounding OAR may be greater, resulting in steeper dose gradients outside the PTV. Second, each beamlet from each direction may provide a different 3D dose contribution to the patient. Therefore, increasing the number of such unique beamlets may give the optimizer more "basis vectors" to work with when sculpting optimal dose profiles around critical structures.

Note that just entering the patient from many directions may not be sufficient to ensure optimal plan quality. It may be that in some cases, portions of the PTV are only able to be exposed from a small number of directions when protecting nearby OAR, even though the number of beams entering the patient is high. This can result in either under coverage of small regions of the PTV, non-conformal regions (dose streaks), or unsatisfactory dose compensation. To encourage maximal coverage and conformality, it may be desirable to have each elemental volume of the PTV be individually targeted from many different directions.

Figure 9:
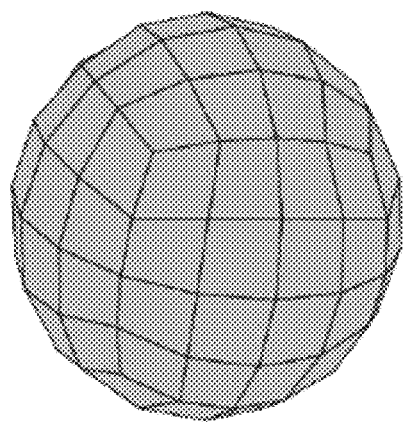
FIG. 9 illustrates an exemplary quadrilateralized spherical cube that may be used for evaluating the angular flux according to some embodiments.

According to some embodiments, an angular flux of a given point in a PTV may be evaluated by computing the 3D direction vectors of incident beamlets and binning them in angular bins. FIG. 9 illustrates an exemplary quadrilateralized spherical cube that may be used for evaluating the angular flux. As illustrated, each cube face may be divided into 4×4 squares. Thus, there are 6×4×4=96 squares. Each square corresponds to a single angular bin. This may provide a bin size on the order of 20 degrees, which may correspond to the same order of distance between vertices in a delivery coordinate space (DCS). In a general case, each cube face may be divided into $2^{2n}$ squares, where n is a positive integer. In the example illustrated in FIG. 9, n=2. This binning method may result in bins of unequal solid angles, but the differences may be relatively small (at most 19%). Additionally, randomly orienting each spherical cube across a set of sampling points may cancel out such discrepancies. In other embodiments, the angular flux may be evaluated by computing the 3D direction vectors of incident beamlets through a closed surface of a shape other than the quadrilateralized spherical cube. For example, the closed surface can be a spherical surface or a cube surface.

A set of sampling points may be distributed within a PTV. The angular flux at each sampling point may be evaluated and optimized during trajectory optimization. According to some embodiments, indexing each bin from 0 to 95, the angular flux of a given PTV point may be stored as a 12 byte bitset, enabling fast bitwise calculations to be performed. If there are n PTV points considered, then the angular flux state $\mathcal{A}$ is represented as a vector of length n of bitsets each with 96 bits.

B. Dual-Distance Metric

According to some embodiments, the information stored in the BEV score bundle sections and the BEV region connectivity manifold may be used to generate treatment plans for radiotherapy. The BEV region connectivity manifold may serve as a scaffold to guide the optimizer, which may make a search space small enough to apply graph search techniques with fast computation times.

In general, optimal trajectories in a VMAT-like treatment may be ones that hit the PTV as much as possible, avoid or minimize healthy tissue doses, and enter the PTV from many different directions, and can be completed in a relatively short delivery time. Some of the goals may conflict with each other. For example, a treatment plan that treats each PVT element from every direction with a high degree of MLC modulation may produce a nearly ideal dose distribution, but may also take an excessive amount of time to deliver. Therefore, it may be desirable to find a trajectory that covers many directions around the patient in an efficient way. According to some embodiments, an optimization method may seek to maximize trajectory length, while using relatively "straight" trajectories for delivery efficiently. The "straightness" of a trajectory may be understood in terms of a geodesic line. A geodesic is the shortest path between two given points in a curved space. A geodesic may be calculated by finding a line that minimizes a distance function between the two points.

According to some embodiments, based on the BEV score bundle sections and the BEV region connectivity manifold, trajectories that have control points traversing through regions of high region scores $\mathcal{R}$ may be preferred (e.g., as defined in Equation (3)). To encourage geodesics to traverse such control points, a distance function may be defined such that smaller non-negative distances are preferred. On the other hand, to pick long trajectories, another distance function may be defined such that larger distances are preferred.

To overcome this inherent conflict between trying to find "short" as well as "long" trajectories, a dual-distance metric approach is used in an optimization according to some embodiments. The dual-distance metric includes two distance functions that play different roles in the optimization. The two distance functions may be referred to as a min-distance function $D^{min}$ (where smaller values are preferred; minimization defines geodesic paths in a graph), and a max-distance function $D^{ax}$ (where larger values are preferred; to be maximized through selection of trajectory).

C. Stateful Graph Optimization

According to some embodiments, a symmetric directed graph may be used for trajectory optimization using the min-distance function $D^{min}$ and the max-distance function $D^{max}$. Since the distance functions may depend not just on the edges of the graph, but also on the history of a trajectory up to that point, a statefulness may be introduced to the graph.

The graph may include a set of nodes, and a set of edges that connect the nodes. To account for the history in the graph, a point may be defined to be a node and state pair P=(N, $\mathcal{A}$). The state may be the PTV angular flux state described above. Given a point $P_1=(N_1, \mathcal{A}_1)$ and an edge $E=(N_1, N_2)$, the successor point is $P_2=(N_2, \mathcal{A}_2)$, where the new state $\mathcal{A}_2$ may be given by a successor state function $\sigma(\mathcal{A}_1, E)$, which describes how the state changes moving along the edge E. The min-distance and max-distance between these two points may be denoted as $D^{min/max}(P_1, P_2)$.

A path may be an ordered sequence of points, $P(P_1, P_n)$ such that $\exists E=(N_i, N_{i+1})$ and $\mathcal{A}_{i+1}=\sigma(\mathcal{A}_i, N_i, N_{i+1}))$ for all $1 \le i < n$. The min-distance and max-distance of this path may be $D^{min/max}(P)=\Sigma_{i=1}^{n-1} D^{min/max}(P_i, P_{i+1})$. Given an initial state $\mathcal{A}$ and two nodes N and N', let the set of all possible paths between them, $P(P_1, \ldots, P_n)$ such that $P_1=(N, \mathcal{A})$ and $P_n=(N', \mathcal{A}')$, where $\mathcal{A}'$ is unspecified, be denoted $\mathcal{P}(N, N'|$ $\mathcal{A}$). A set of trajectories may be defined to be the set of paths with a minimal min-distance, $$\mathcal{T}_{(N,N'|\mathcal{A})} = \arg\min_{P \in \mathcal{P}(N,N'|\mathcal{A})} D^{min}(P). \quad (13)$$

A set of optimal trajectories between these two nodes may then be defined to be the trajectories with a maximum max-distance, $$\mathcal{T}^{optimal}_{(N,N'|\mathcal{A})} = \arg\max_{P \in \mathcal{T}(N,N'|\mathcal{A})} D^{max}(P). \quad (14)$$

Using the definitions provided by Equations (5) and (6), the min-distance and max-distance between two arbitrary nodes is $D^{min/max}(N,N'|\mathcal{A}) = D^{min/max}(P)$ for $P \in \mathcal{T}^{optimal}(N,N'|\mathcal{A})$.

Given an initial state $\mathcal{A}$, the goal now may be to define a globally optimal trajectory. If attention is restricted to start and end nodes in some set $\mathcal{B}$, then a set of optimal trajectories ending on the set $\mathcal{B}$ may be defined to be:

$$\mathcal{T}_\mathcal{B}^{optimal}(\mathcal{A}) = \cup_{(N,N') \in \mathcal{E}_\mathcal{B}^{optimal}} \mathcal{T}^{optimal}(N,N'|\mathcal{A}) \quad (15)$$

where $\mathcal{E}_\mathcal{B}^{optimal} = \arg\max_{(N,N')} \text{for } N,N' \in \mathbf{N'} \in \mathcal{B} \; D^{max}(N,N'|\mathcal{T}_\mathcal{B}^{optimal})$.

The optimization problem may be to find an element of $\mathcal{T}_\mathcal{B}^{optimal}(\mathcal{A})$ for some initial state $\mathcal{A}$ and the set of start and end points $\mathcal{B}$.

D. Graph Definitions

According to some embodiments, a control point in the graph may be uniquely determined by three integers, vertex v (i.e., a point on the delivery coordinate space or DCS), collimator index c (which determines collimator angle out of a discrete set of possibilities), and region bitfield b. The region bitfield b is a list of boolean flags that determine which subset of regions to select for a given vertex. These three integers may define a node in the graph as N=(v, c, b). Starting MLC leaf positions may be determined by fitting to this subset of regions of the BEV.

According to some embodiments, the BEV region connectivity manifold may include multiple mutually disjoint connected components, each of which forms a single connected part of the total search graph through the following definition of edges. Given two nodes $N_1=(v_1, c_1, b_1)$ and $N_2=(v_2, c_2, b_2)$, there may be an edge E connecting these two nodes if the following are satisfied:

There is an edge connecting $v_1$ and $v_2$ in the delivery coordinate space;

$\Delta t_{collimator} \le \Delta t_{directional}$, where $\Delta t_{collimator}$ is the time for the collimator to move $\Delta\theta_{collimator} = \theta_{collimator}(c_2) - \theta_{collimator}(c_1)$, and $\Delta t_{directional}$ directional is the time to move in gantry and couch space from vertex $v_1$ to $v_2$.

The set of boundary nodes $\mathcal{B}$ are the potential start and end nodes in the graph optimization. To define this set of boundary nodes, it may be necessary to first define boundary vertices in the delivery coordinate space for one-dimensional (1D) and two-dimensional (2D) spaces (which may be generalized to higher dimensions). A 1D space may be made of only vertices and edges, and boundary vertices are those which touch at most a single edge. Similarly, in a 2D space of vertices, edges and faces, boundary vertices are those which belong to an edge that only touches a single face. With this definition, a region $\mathcal{R} = (n_v, n_{subindex})$ may be a boundary region if one of the following conditions is satisfied:

(1) Vertex v of index $n_v$ is a boundary vertex;
(2) There exists an edge in the delivery coordinate space touching vertex v of index $n_v$ such that there is no region edge along this delivery coordinate space edge emanating from region r.

Figure 10A:
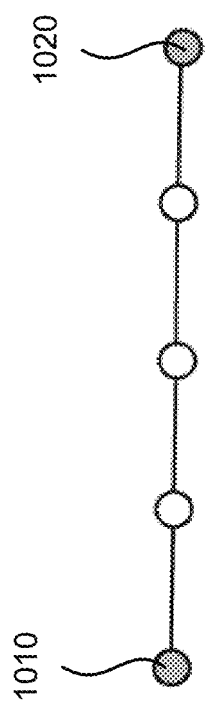
FIG. 10A illustrates boundary nodes in a one-dimensional (1D) delivery coordinate space according to some embodiments.
Figure 10B:
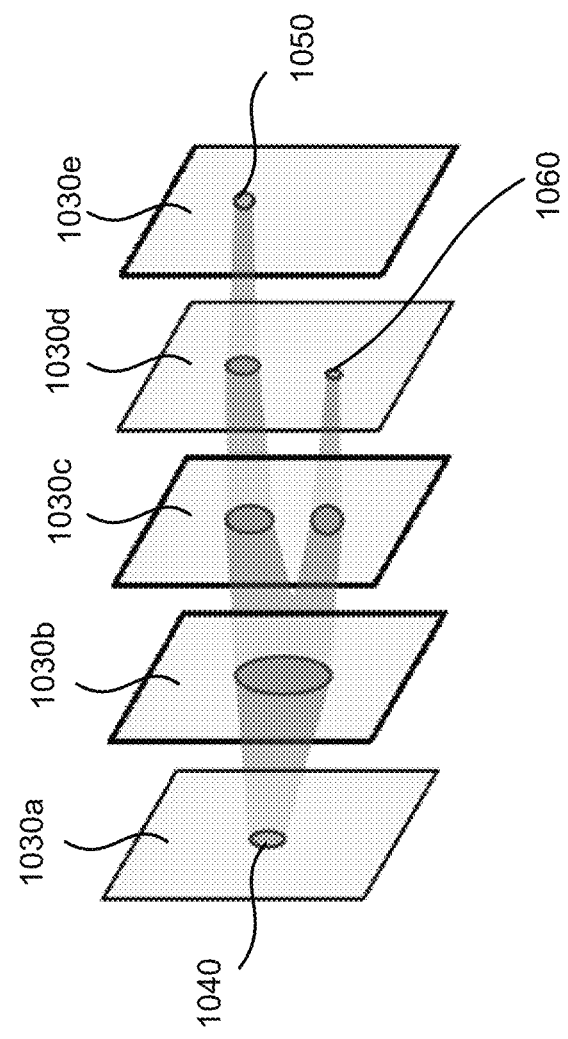
FIG. 10B illustrates boundary nodes in a two-dimensional (2D) delivery coordinate space according to some embodiments.

FIGS. 10A-10B illustrate these conditions. FIG. 10A may represent a 1D delivery coordinate space, with boundary vertices 1010 and 1020 represented as filled circles. FIG. 10B may represent a 2D delivery coordinate space. The BEV region connectivity manifold is represented by ovals (with each oval representing a region) in five BEV planes 1030a-1030e, and the connections between them. The region 1040 in the leftmost plane 1030a and the region 1050 on the rightmost plane 1030e are boundary regions that satisfy condition (1) above, while the region 1060 in the plane 1030d has no connection to a region on the right, thus is a boundary region that satisfy condition (2) above. With these definitions, a node is a boundary node if all the regions denoted by its region bitfield are boundary regions.

The state information used in the graph optimization is PTV angular flux $\mathcal{A}$. Using a bitset definition of PTV angular flux as described above, the successor function $\sigma$, which defines how the state changes, may be defined by the bitwise OR operator, $\sigma(\mathcal{A}_1, (N_1, N_2)) = \mathcal{A}_1 | \mathcal{A}(N_2)$, where $\mathcal{A}(N_2)$ is the contribution to the angular flux state from the regions denoted by region bitfield $b_2$ at vertex $v_2$.

Given two points $P_i = (N_i, \mathcal{A}_i)$ where $N_i = (v_i, c_i, b_i)$ for i=1,2 with edge E connecting the nodes, min/max-distance functions may be defined as, $$D^{min}(P_1, P_2) = \Delta\theta(E)\left(\frac{3}{S(P_1, P_2)} + t^{mlc}(E) + p^{eff} \cdot (E)\right), \quad (16)$$

$$D^{max}(P_1, P_2) = \Delta\theta(E)S(P_1, P_2), \quad (17)$$

where $\Delta\theta$ is the physical angular distance traveled by the treatment head. The min-distance function is set to $+\infty$ if the resulting MLC configuration violates machine limitations. Note that the score term $S(P_1, P_2)$ appears as the inverse of one another in each equation, reflecting the fact that, roughly speaking, max-distance="goodness" and min-distance=1/"goodness". The definitions and meanings behind each term are as follows:

$$S(P_1,P_2) = S^{score}(b_2) + 2 S^{angular}(\mathcal{A}_1, \mathcal{A}_2)$$

$$-S^{score}(b) = \frac{\mathcal{R}_{avg}(b)+1}{2} \cdot \max(0, A(b) - A_{penalty}(b)),$$

where $\mathcal{R}_{avg}(b)$ is the average region score of the regions of bitfield b per unit area, A(b) is the combined area of regions of bitfield b, and $A_{penalty}(b)$ is the total non-region area exposed by the fitted MLCs. This term penalizes poor MLC target fitting and encourages high scoring regions.

$S^{angular}(\mathcal{A}_1, \mathcal{A}_2)$ is a term that encourages regions that provide novel angles to the existing angular flux state. If $\mathcal{A}_{avg}$ is the average contribution (number of bits) to a blank angular flux state from each region, then $S^{angular}(\mathcal{A}_1, \mathcal{A}_2)$ is the number of bits in ($\mathcal{A}_2$ &~ $\mathcal{A}_1$) or 1 (whichever is larger), normalized by dividing by $\mathcal{A}_{avg}$.

$t^{mlc}$ is the time for the MLCs to move between control points. This penalizes collimator angles that result in excessive MLC motion.

$p^{eff} = (1 - \Delta\theta/\theta\Delta_{max})$ is a factor that penalizes edges where the trajectory is almost stationary, so treatment time is not wasted in such locations.

The score term $S(P_1, P_2)$ may be the main force driving the optimizer to find trajectories that target the PTV from good directions and that give contributions from different directions while avoiding poor MLC target fitting.

E. Graph Optimization Solution

The stateful dual-distance metric graph optimization defined above may be solved using the Dijkstra algorithm. Converting the list of points from the resulting optimal trajectory to control points may provide the desired radiotherapy trajectory. Running Dijkstra's algorithm from a start node without stopping at any particular end node may result in a tree structure of points, effectively completing a 1-to-N search from the given starting node to all other nodes with the same computational complexity as the usual 1-to-1 search between two nodes. By selecting the trajectory with the largest max-distance, the restricted optimization problem of finding the optimal trajectory from a given node may be solved efficiently.

In general, to find the globally optimal trajectory with the largest max-distance may require repeating this computation from every possible node (N-to-N search). An approximately optimal trajectory can be found by picking an arbitrary start node, and running this algorithm repeatedly with the same initial state, using the end node of the previous run as the start node of the successive run. In some embodiments, this process is repeated twice; thus trajectory optimization may be carried out with the same computational complexity as the underlying Dijkstra algorithm.

The path optimization may be carried out for each connected component of the graph. The trajectory with the largest max-distance across all possibilities may be selected in the end. The presence of the angular flux state in the distance function may help ensure that the selected trajectory will also be one that tends to provide novel directions from which to treat the PTV.

Figure 11:
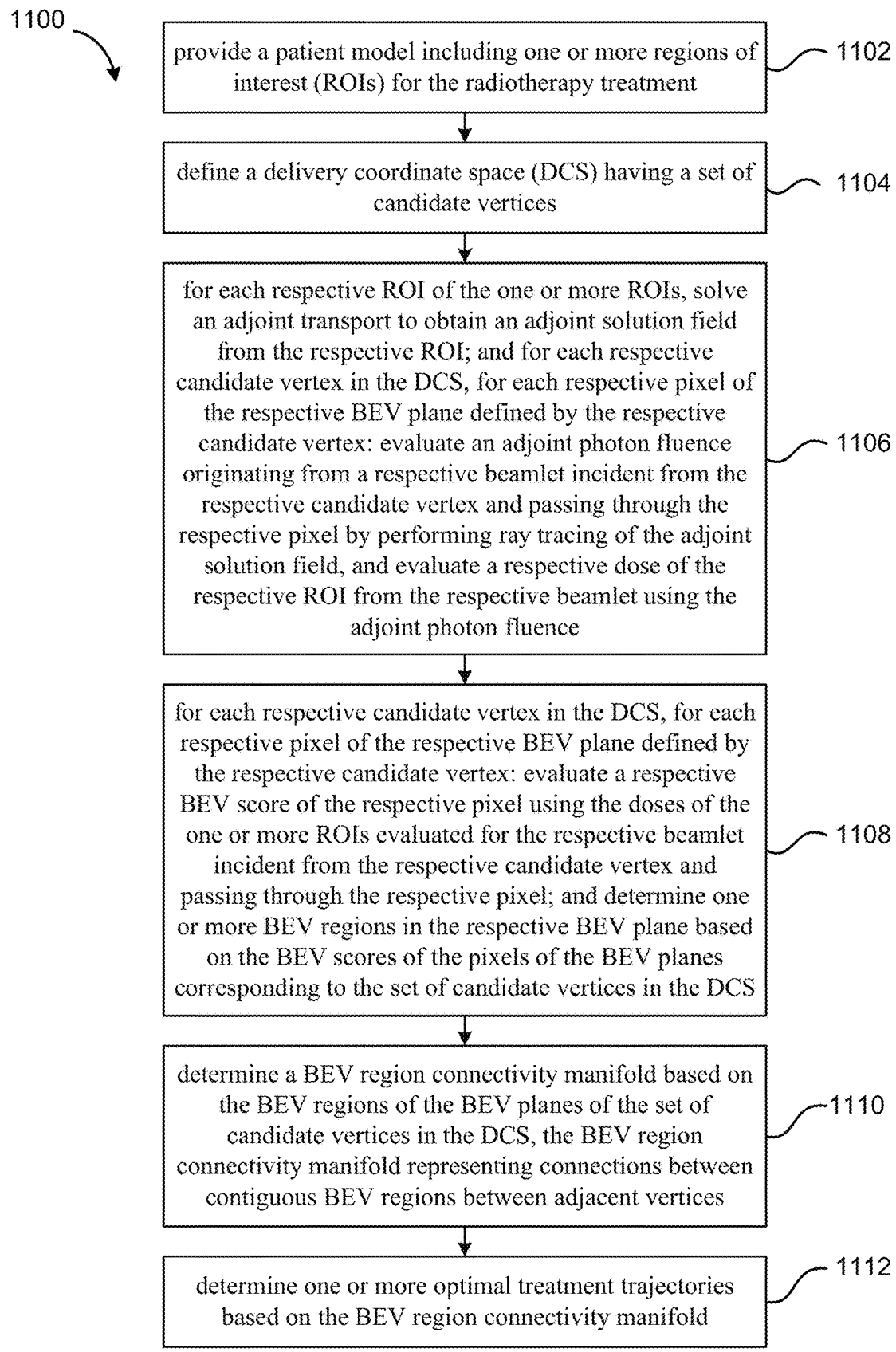
FIG. 11 shows a flowchart illustrating a method of trajectory optimization according to some embodiments.

F. Method of Trajectory Optimization for Radiotherapy Treatment Using Sectioning FIG. 11 shows a flowchart illustrating a method 1100 of trajectory optimization for radiotherapy treatment using sectioning according to some embodiments.

At 1102, a patient model is provided. The patient model includes one or more regions of interest (ROIs) for the radiotherapy treatment.

At 1104, a delivery coordinate space (DCS) is defined. The DCS has a set of candidate vertices. Each respective candidate vertex defines a respective beam's eye view (BEV) plane.

At 1106, for each respective ROI of the one or more ROIs, an adjoint transport is solved to obtain an adjoint solution field from the respective ROI. For each respective candidate vertex in the DCS, and for each respective pixel of the respective BEV plane defined by the respective candidate vertex, an adjoint photon fluence originating from a respective beamlet incident from the respective candidate vertex and passing through the respective pixel is evaluated by performing ray tracing of the adjoint solution field; and a respective dose of the respective ROI from the respective beamlet is evaluated using the adjoint photon fluence.

At 1108, for each respective candidate vertex in the DCS, and for each respective pixel of the respective BEV plane defined by the respective candidate vertex, a respective BEV score of the respective pixel is evaluated using the doses of the one or more ROIs evaluated for the respective beamlet incident from the respective candidate vertex and passing through the respective pixel; and one or more BEV regions in the respective BEV plane are determined based on the BEV scores of the pixels of the BEV planes corresponding to the set of candidate vertices in the DCS.

At 1110, a BEV region connectivity manifold is determined based on the BEV regions of the BEV planes of the set of candidate vertices in the DCS. The BEV region connectivity manifold represents connections between contiguous BEV regions between adjacent vertices.

At 1112, one or more optimal treatment trajectories are determined based on the BEV region connectivity manifold.

It should be appreciated that the specific steps illustrated in FIG. 11 provide a particular method of trajectory optimization according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

VI. Beam Angle Optimization Using Adjoint Transport for Dose

The TORUS methods use the the BEV regions and the BEV region connectivity manifold as a guide to generate heuristically optimal radiotherapy trajectories automatically for efficient delivery of high quality VMAT treatment plans. According to some embodiments, the TORUS methods are modified to generate heuristically optimal IMRT fields. As discussed above, the TORUS methods use an optimization graph on top of a delivery coordinate space to generate optimal treatment trajectories through the use of a dual-metric optimization. Nodes in the optimization graph represent individual control points, and trajectories are defined to be paths that minimize a min-distance metric, while a max-distance metric acts as a measure of goodness to select optimal trajectories. For an IMRT treatment plan, treatment fields may be represented in this framework as a set of nodes. A beam angle optimization may involve finding a set of k nodes that have optimal max-distance.

A. Field Geometry Optimization

According to some embodiments, to find a set of k beams, a BAO graph based on the TORUS graph concept may be built based on the following nodes and edges:

Nodes

Nodes are a set $\mathcal{N}$ of N tuples of the form (v, c, b), where v is a vertex, c is the collimator angle index, and b is a binary mask of included regions. Each tuplet may determine a single field. The vertex v may correspond to a location in a discretized delivery coordinate space (DCS). For example, in a C-arm linear accelerator, the vertex v may correspond to an isocenter, a gantry angle $\theta_{gantry}$, and a couch angle $\theta_{couch}$. The collimator angle index c may correspond to a collimator angle $\theta_c$ out of a set of discrete possible collimator angles. The region mask b may correspond a set of contiguous target regions the MLC leaves may expose.

Edges

Edges are connections between neighbor nodes that have vertex-vertex connectivity in the underlying delivery coordinate space, and MLC connectivity between the respective MLC leaf sequences. In the case of beam angle optimization, the MLC connectivity constraint may not be important, but it may nevertheless act to reduce the number of edges in the graph. Thus, it may be computationally useful to keep the MLC connectivity constraint.

In the TORUS methods, a min-distance and a max-distance may be defined along edges in the TORUS graph. In the case of static fields, there is no gantry motion while the treatment beam is on. Therefore, only the vertices themselves need to be considered, and there is no need for a min-distance function. The score (max-distance) may be the metric to optimize. The score S may be defined on subsets of nodes as, $$S(\mathcal{B}) = \text{max-distance corresponding to the set of nodes (beams) } \mathcal{B} \subset \mathcal{N}. \quad (18)$$

The optimal set of k beams may be defined to be the subset $\mathcal{B} \subset \mathcal{N}$ with $|\mathcal{B}|=k$ that gives an optimal score $S(\mathcal{B})$, where $|\mathcal{B}|$ represents the number of beams in the subset $\mathcal{B} \subset \mathcal{N}$.

The score $S(\mathcal{B})$ may be a complex non-local function of the entire subset $\mathcal{B}$. Therefore, it may be a non-trivial problem to solve exactly. However, there may exist an efficient way to find approximate solutions faster than trying all $_NC_k$ combinations. In some embodiments, a beam angle optimization may include the following steps:

(1) Evaluate the scores for individual beams ($|\mathcal{B}|=1$), and use the squares of these scores as sampling probabilities.

(2) Randomly sample k beams using the sampling probabilities.

(3) Apply local gradient descent to this set $\mathcal{B}$ to find a local minimum.

(4) Repeat steps (1)-(3) until there is no improvement in score found for a predetermined number of successive trials (e.g., 20 successive trials).

This procedure may be referred to as a gradient descent method. During each iteration of the gradient descent procedure, all possible "edges" may be considered looking for improvement, where an "edge" is motion of the subset $\mathcal{B}$ to a neighbor subset $\mathcal{B}'$. The subset of beams may be updated to move in the direction that most improves the score. This procedure may be repeated until no more local improvements in the score is found. A neighbor to subset $\mathcal{B}$ is defined to be another subset $\mathcal{B}'$ that differs in exactly one beam $\mathcal{B}_i \to \mathcal{B}_i'$, where these two beams either share an edge in the TORUS graph or have the same position in the delivery coordinate space (same vertex).

B. Score Function

The score function $S(\mathcal{B})$ may be similar to the max-distance function as in TORUS. The score $S(\mathcal{B})$ of a set of beams $\mathcal{B}$ may include two parts: individual beam scoring, and overall PTV angular flux novelty. The presence of the global PTV angular flux metric is what makes the score function non-local, whereby it is not simply a function of the scores of the individual beams. The score $S(\mathcal{B})$ may be written as the sum of two parts, $$S(\mathcal{B}) = S_{local}(\mathcal{B}) + 3 S_{flux}(\mathcal{B}), \quad (19)$$

where the local part $S_{local}(\mathcal{B})$ may be defined as $$S_{local}(\mathcal{B}) = \sum_{B \in \mathcal{B}} S_{beam}(B), \quad (20)$$

$$S_{beam}(B) = w(B) \cdot \left( \frac{s(B)}{A_{avg}} + \frac{0.2}{\max(0.05, o(B))} \right), \quad (21)$$

$$w(B) = \max(0.1, \min(1.0, 1.1 - c^2(B))), \quad (22)$$

$$c(B) = \text{MLC contention severity}, \quad (23)$$

$$s(B) = \text{integrated score of regions}, \quad (24)$$

$$o(B) = \frac{2}{1 + CrossSection^2(B)} + x_{rms}(B)/2. \quad (25)$$

$A_{avg}$ may be defined to be the average area of regions. Thus, the term $$\frac{s(B)}{A_{avg}}$$

may be considered as the average region score. In some embodiments, the MLC contention severity may relate to $A_{penalty}$ defined above as the total non-region area exposed by the fitted MLCs. The cross section may be defined to be the y extent of the open MLC leaves normalized to the average diameter of regions as circles. $x_{rms}(B)$ may be defined as the root-mean-square x extent of open leaves. The flux part $S_{flux}(\mathcal{B})$ may be defined as the PTV angular flux novelty of the angular flux state generated by the selected regions, normalized by dividing by the average angular flux novelty of the individual regions. The separation of the score into local and non-local parts may allow some code optimizations to be done by pre-computing the contributions of individual beams to the local part.

C. Beam Angle Optimization Including Consideration of Beam-Off Time

Consider an IMRT treatment as an external-beam radiotherapy treatment, where the dose is delivered from k static beam locations $r_i=(v_i, c_i)$, $i=1, \ldots, k$, where the indices $v_i$ and $c_i$ correspond to vertex and collimator angle index, respectively. In a C-arm linear accelerator treatment system, a vertex may include an isocenter, a gantry angle, and a couch angle. In other types of external-beam radiation treatment systems, a vertex may include other treatment axes variables. The fluence delivered from each $r_i$ may be determined by way of a fluence-optimization scheme that distributes the fluence optimally between the $r_i$ such that clinical optimization objectives are fulfilled.

A dosimetrically optimal IMRT treatment plan may be found within a given delivery coordinate space by running fluence optimization and leaf sequencing for each permissible combination of $\{r_i\}_{i=1}^{k}$, and by picking the dosimetrically optimal one. However, this process may be impractical due to the large number of possible combinations. Moreover, it may be desirable that the patient and the patient's internal organs remain stationary during the administration of radiation for the delivered dose to match the planned dose. The longer the treatment takes, the more likely that the patient or the patient's internal organs may move during the treatment, and hence a higher probability of not delivering the intended dose to the target volumes.

The overall treatment time may be prolonged by the beam-off transition times from beam $r_i$ to $r_{i+1}$. The total beam-off transition time from beam $r_i$ to $r_{i+1}$ may be expressed as $\Delta t_{i,i+1} = \max_j$, where the changes may include, but are limited to the following:

a time of $\Delta_{i,i+1}^{move}$ to move machine axes from positions at vertex $v_i$ to those at $v_{i+1}$;

a time of $\Delta t_{i,i+1}^{collimator}$ to rotate the collimator from $c_i$ to $c_{i+1}$;

a time of $\Delta t_{i,i+1}^{imaging}$ of acquiring an image or multiple images for guidance of treatment between beams i and i+1.

A minimization of the aggregate beam-off time $\Delta t = \sum_{i=1}^{k-1} \Delta t_{i,i+1}$ may be an important part of the beam-selection problem. In some embodiments, a BAO algorithm may include constraints on picking beams that can be delivered in a time-efficient radiation order. In some other embodiments, the radiation order of the beams may be determined as a post-processing step.

D. Method of Beam Angle Optimization Using Sectioning

Figure 12:
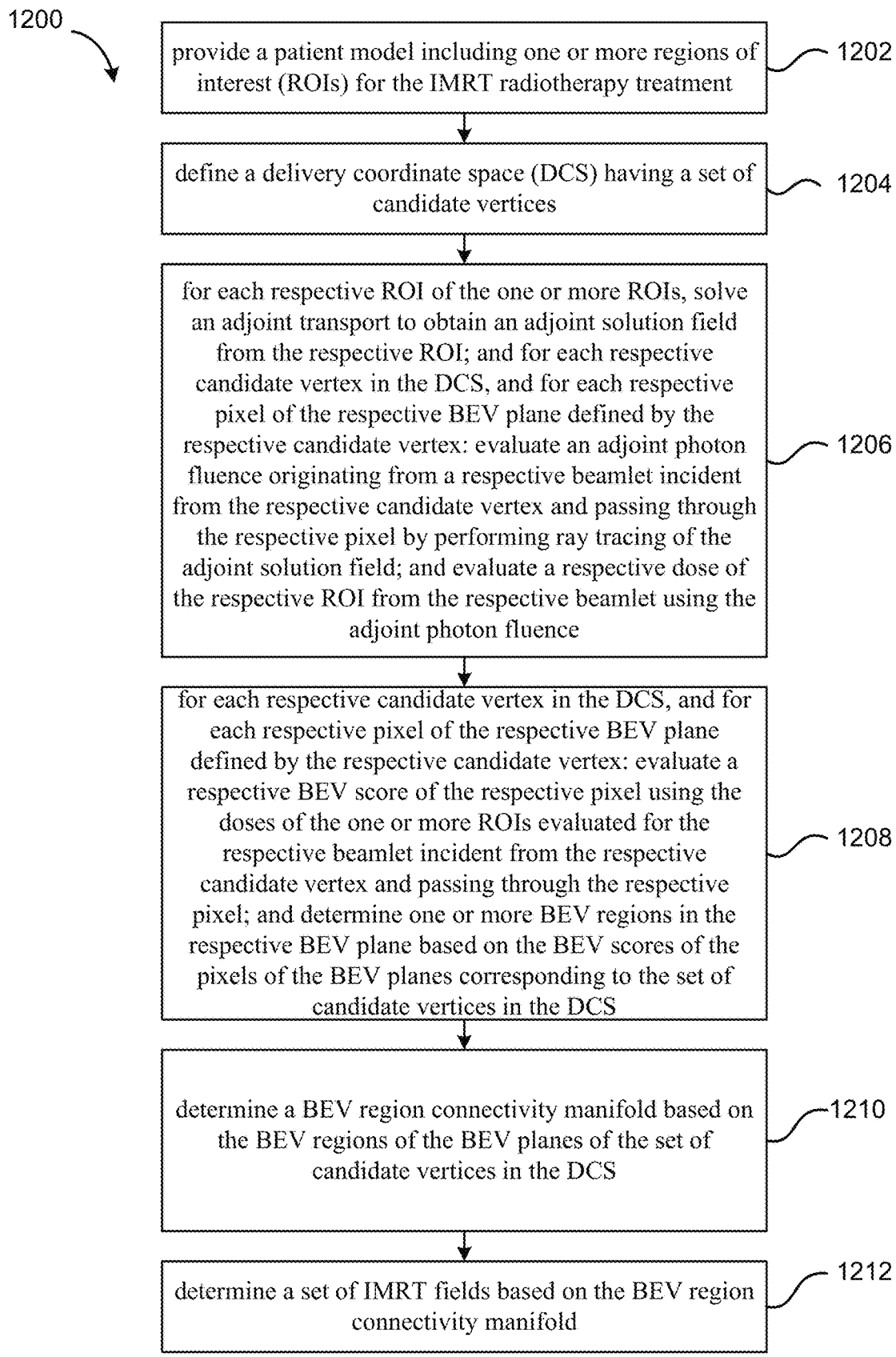
FIG. 12 shows a flowchart illustrating a method of beam angle optimization according to some embodiments.

FIG. 12 shows a flowchart illustrating a method 1200 of beam angle optimization using secitoning for an IMRT radiotherapy treatment according to some embodiments.

At 1202, a patient model is provided. The patient model includes one or more regions of interest (ROIs) for the IMRT radiotherapy treatment.

At 1204, a delivery coordinate space (DCS) is defined. The DCS has a set of candidate vertices. Each respective candidate vertex defines a respective beam's eye view (BEV) plane.

At 1206, for each respective ROI of the one or more ROIs, an adjoint transport is solved to obtain an adjoint solution field from the respective ROI; and for each respective candidate vertex in the DCS, and for each respective pixel of the respective BEV plane defined by the respective candidate vertex: an adjoint photon fluence originating from a respective beamlet incident from the respective candidate vertex and passing through the respective pixel is evaluated by performing ray tracing of the adjoint solution field; and a respective dose of the respective ROI from the respective beamlet is evaluated using the adjoint photon fluence.

At 1208, for each respective candidate vertex in the DCS, and for each respective pixel of the respective BEV plane defined by the respective candidate vertex: a respective BEV score of the respective pixel is evaluated using the doses of the one or more ROIs evaluated for the respective beamlet incident from the respective candidate vertex and passing through the respective pixel; and one or more BEV regions in the respective BEV plane are determined based on the BEV scores of the pixels of the BEV planes corresponding to the set of candidate vertices in the DCS.

At 1210, a BEV region connectivity manifold is determined based on the BEV regions of the BEV planes of the set of candidate vertices in the DCS. The BEV region connectivity manifold represents connections between contiguous BEV regions between adjacent vertices.

At 1212, a set of IMRT fields is determined based on the BEV region connectivity manifold. Each respective IMRT field of the set of IMRT fields defines a beam angle corresponding to a respective vertex in the DCS.

It should be appreciated that the specific steps illustrated in FIG. 12 provide a particular method of beam angle optimization according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

VII. Trajectory Optimization Considering Multiple Candidate Energy Modes

As discussed above, for a given direction of incidence (e.g., a given vertex $n_v$ in the DCS), a dose response of a given region of interest $n_{ROI}$ to a beamlet at a respective pixel $(n_x, n_y)$ of a corresponding BEV plane, $\mathcal{D}_{n_v,n_x,n_y,n_{ROI}}$, may be evaluated using the adjoint transport approach according to Equation (12). In some embodiments, the dose response may be evaluated using other methods. For example, the dose response may be evaluated using the forward transport approach according to Equation (7). A BEV score for each pixel, $S_{n_v,n_x,n_y}$, may be evaluated as a weighted linear combination of the doses to the $N_{ROI}$ regions of interest according to Equation (2). The BEV score may be a measure of "goodness" of the beamlet as a candidate for irradiation of the target volumes. For a given BEV plane, BEV regions may be identified as candidate irradiation apertures according to a region selection criterion based on the BEV scores.

The size of a BEV region may depend on all other candidate directions. The size of a BEV region may also depend on how deep-seated the target volumes (PTVs) are, and where organs at risk (OARs) are located relative to the target volumes along the direction of incidence. In addition, the size of a BEV region may depend on the energy mode of a radiation beam. The energy mode of a radiation beam may be a combination of the photon energy and the distribution of photon number density perpendicular to the direction of irradiation in the divergent frame of reference. The dependence of a BEV region on energy mode may be due to the differences of depth-dose curves at different energy modes. For example, for a given photon number density, at low photon energies, more energy may be deposited in superficial tissues than at high photon energies; whereas at high photon energies, more energy may be deposited in deep-seated tissues.

Figure 13B:
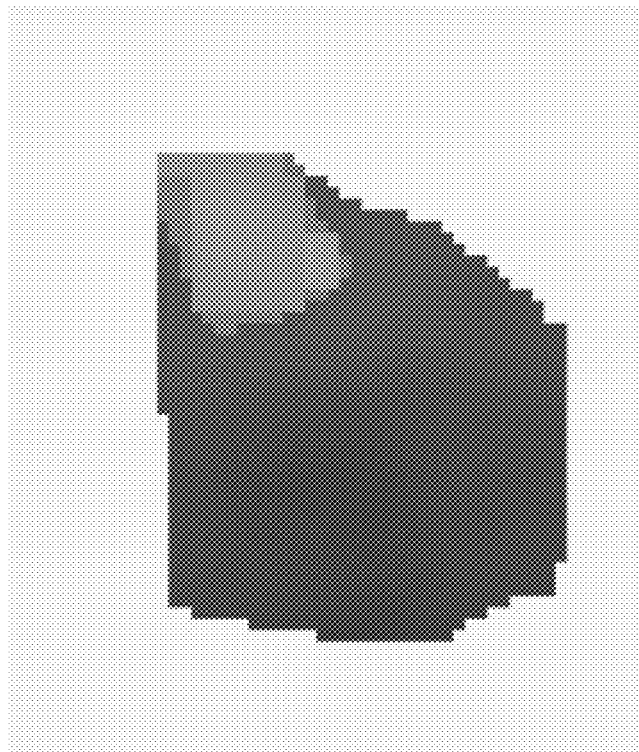
FIGS. 13A and 13B show exemplary BEV regions for a given direction of incidence for two different energy modes, respectively, according to some embodiments.
Figure 13A:
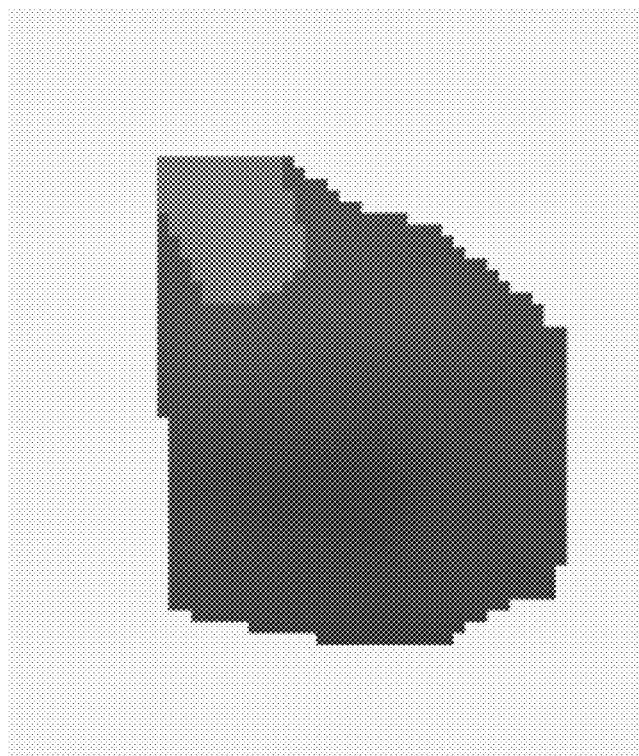

FIGS. 13A and 13B show exemplary BEV regions for a given direction of incidence for a first energy mode and a second energy mode, respectively, where the second energy mode has a higher energy than the first energy mode, according to some embodiments. Darker shades represent lower score values and brighter shades represent higher score values. Orange colors represent beamlets that pass the region selection criterion, and thus are considered as BEV regions as potential open aperture candidates for irradiation of target structures. The blue colored areas correspond to those pixels through which irradiation may deposit dose in the target structures. The light green colored areas correspond to those pixels through which irradiation may not pass through any target structures.

A region score R for a BEV region, in a given direction of incidence, may be defined as, $$R = \int R(n_x, n_y) dA, \quad (26)$$

where $R(n_x, n_y)$, a non-negative real number smaller than or equal to one, is a normalized weighted sum of the aggregate dose deposited to regions of interest from a beamlet corresponding to pixel $(n_x, n_y)$, and the integration is over the area of the BEV region (e.g., the orange colored region in FIG. 13A or FIG. 13B). The larger the region score R, the more dose is deposited to the target volume and less dose is deposited to organs at risk via irradiation through the BEV region.

As illustrated in FIGS. 13A and 13B, a higher energy mode (FIG. 13B) may lead to a larger and brighter BEV region as compared to a lower energy mode (FIG. 13A). A larger area of a BEV region means that the target volume may be safely irradiated through a larger aperture. A brighter BEV region means that more aggregate dose may be deposited to the target volume. Based on Equation (26), both a larger and brighter BEV region may lead to a higher region score R. Therefore, because of the possible dependence of BEV regions on energy, a given direction of incidence may be preferable for some energy modes, while not for some other energy modes.

According to some embodiments, trajectory optimization and beam angle optimization in a radiation treatment plan may consider multiple candidate energy modes. For example, instead of considering a single energy mode, a set of candidate energy modes may be considered. BEV regions and BEV region connectivity manifold may be identified and constructed for each energy mode of the set of candidate energy modes. Trajectory optimization may be performed concurrently with the optimization of energy modes based on the BEV regions and the BEV region connectivity manifold for the set of candidate energy modes.

In the following, two approaches of trajectory optimization considering multiple candidate energy modes are described. In a first approach, a trajectory optimization is performed for each energy mode of a set of candidate energy modes to obtain a respective candidate set of trajectories for each energy mode. The energy mode corresponding to the candidate set of trajectories that gives rise to the optimal value of an objective function ("score") may be picked. In some embodiments, the objective function may be the dual max-min objective function in TORUS, as described above. The first approach may be referred to as single-energy-mode trajectory optimization over multiple candidate energy modes, as the set of trajectories selected for the radiation treatment plan has the same energy mode for all trajectories in the set.

In a second approach, the end result of a trajectory optimization may be a set of trajectories, possibly with different energy modes for different trajectories. The second approach may be referred to as mixed-energy-mode trajectory optimization over multiple candidate energy modes, as some trajectories in the set may be in first energy mode while some other trajectories in the set may be in a second energy mode different from the first energy mode. The capability to mix different energy modes may be beneficial in treatments in which a homogeneous dose is a high-priority clinical goal, or in treatments in which some targets are superficial while some other targets are deep-seated (e.g., in intracranial multi-metastasis cases or breast multi-metastasis cases).

A. Single-Energy-Mode Trajectory Optimization Over Multiple Candidate Energy Modes In some embodiments, a methods of trajectory optimization considering M candidate energy modes may generate a set of N trajectories intended for VMAT-like delivery using a single energy mode by running a path optimization algorithm sequentially M times, as described in an example below.

According to some embodiments, to find an optimal energy mode among M candidate energy modes (indexed as m=1, . . . M) for a set of N trajectories (indexed as n=1, . . . N), a trajectory optimization may include the following steps:

1. Set m=1;
   (a) Set n=1 and PTV angular flux state $F_0^m=0$;
     (i) Find $n^{th}$ optimal trajectory $T_n^m$ and flux state $F_n^m$ against flux state $F_{n-1}^m$ at energy mode m.
     (ii) If n=N, go to 1(b). Otherwise, set n=n+1 and go to 1(a)(i).
   (b) If the set of trajectories $\{T_n m\}_{n=1}^N$ is better than the current energy mode optimum set $\mathcal{T}$, based on an objective function, set $\mathcal{T}_{current}=\{T_n^m\}_{n=1}^N$ and $F_{current}=F_N^m$;
2. If m=M, stop. Otherwise, set m=m+1 and go to 1(a).

In some embodiments, considering VMAT-like trajectories, along which one or several machine axes move while the treatment beam is on, if connected BEV regions are large for a given energy mode in a set of DCS vertices connected by edges, that energy mode may be considered as a good candidate energy mode, and the set of DCS vertices may be considered as a good candidate path for a VMAT trajectory using that energy mode.

Figure 14:
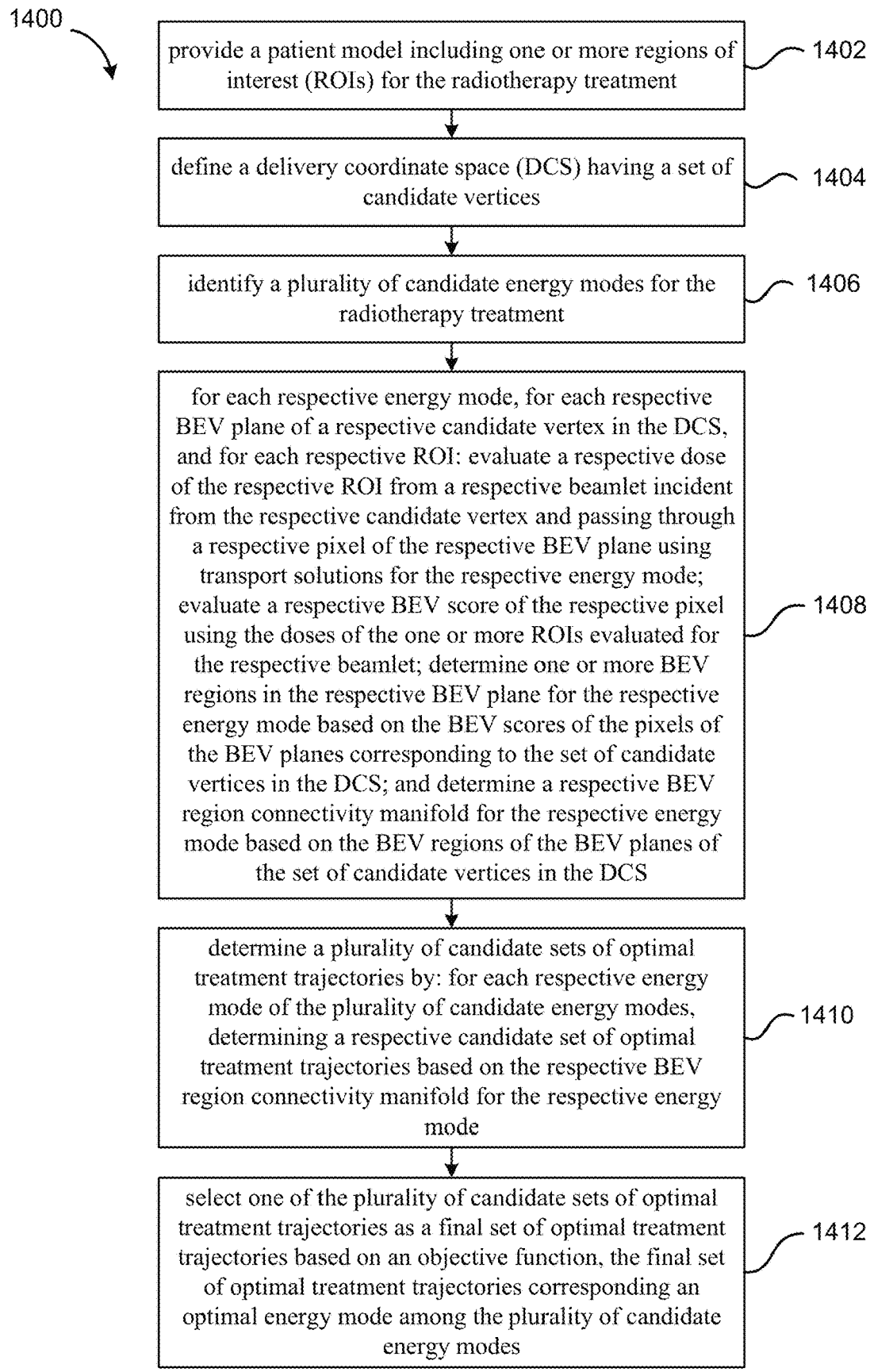
FIG. 14 is a flowchart illustrating a method of trajectory optimization considering multiple candidate energy modes according to some embodiments.

B. First Method of Trajectory Optimization Considering Multiple Candidate Energy Modes FIG. 14 is a flowchart illustrating a method 1400 of trajectory optimization considering multiple candidate energy modes according to some embodiments. The method 1400 may be referred to as single-energy-mode trajectory optimization over multiple candidate energy modes, as discussed above.

At 1402, a patient model is provided. The patient model includes one or more regions of interest (ROIs) for the radiotherapy treatment.

At 1404, a delivery coordinate space (DCS) is defined. The DCS has a set of candidate vertices. Each respective candidate vertex defines a respective beam's eye view (BEV) plane.

At 1406, a plurality of candidate energy modes are identified for the radiotherapy treatment.

At 1408, for each respective energy mode of the plurality of candidate energy modes, for each respective BEV plane of a respective candidate vertex in the DCS, and for each respective ROI of the one or more ROIs: a respective dose of the respective ROI from a respective beamlet incident from the respective candidate vertex and passing through a respective pixel of the respective BEV plane is evaluated using transport solutions for the respective energy mode; a respective BEV score of the respective pixel is evaluated using the doses of the one or more ROIs evaluated for the respective beamlet; one or more BEV regions in the respective BEV plane for the respective energy mode are determined based on the BEV scores of the pixels of the BEV planes corresponding to the set of candidate vertices in the DCS; and a respective BEV region connectivity manifold for the respective energy mode is determined based on the BEV regions of the BEV planes of the set of candidate vertices in the DCS. The respective BEV region connectivity manifold represents connections between contiguous BEV regions between adjacent vertices.

At 1410, a plurality of candidate sets of optimal treatment trajectories is determined by: for each respective energy mode of the plurality of candidate energy modes, determining a respective candidate set of optimal treatment trajectories based on the respective BEV region connectivity manifold for the respective energy mode.

At 1412, one of the plurality of candidate sets of optimal treatment trajectories is selected as a final set of optimal treatment trajectories based on an objective function. The final set of optimal treatment trajectories corresponds an optimal energy mode among the plurality of candidate energy modes.

It should be appreciated that the specific steps illustrated in FIG. 14 provide a particular method of trajectory optimization according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

C. Mixed-Energy-Mode Trajectory Optimization Over Multiple Candidate Energy Modes According to some embodiments, to find a set of N optimal trajectories among M candidate energy modes, in which the N trajectories may have different energy modes (referred to herein as mixed energy mode), a trajectory optimization considering multiple candidate energy modes may include the following steps:

1. Set n=1 and PTV angular flux state $F_{current}=0$;
   (a) Set m=1;
      (i) Find $n^{th}$ optimal trajectory $T_n^m$ and flux state $F^m$ against flux state $F_{current}$ at energy mode m.
      (ii) If $T_n^m$ is better than the current optimum $T_{current}$, based on the objective function, set $T_{current}=T_n^m$ and $F_n=F^m$;
      (iii) If m=M, go to 1(b). Otherwise, set m=m+1 and go to 1(a)(i).
   (b) Set $T_n=T_{current}$ and $F_{current}=F_n$, where $F_{current}$ reflects the PTV angular flux state after finding n trajectories.
2. If n=N, stop. Otherwise, set n=n+1 and go to 1(a).

In some embodiments, a constraint of at most one energy mode change can be added. That is, if n=1, . . . , k trajectories have a constant energy mode $m_0$, but energy mode $m_1 \neq m_0$ is found for trajectory n=k+1, then the energy mode $m_1$ is kept for the remaining n=k+2, . . . , N trajectories.

In some embodiments, considering VMAT-like trajectories, along which one or several machine axes move while the treatment beam is on, if connected BEV regions are large for a first energy mode in a first set of DCS vertices connected by edges, and connected BEV regions are large for a second energy mode in a second set of DCS vertices connected by edges, the first set of DCS vertices and the second set of DCS vertices may be considered as a first candidate trajectory and a second candidate trajectory, respectively, for a mixed-energy mode VMAT treatment involving the first energy mode and the second energy mode.

In some embodiments, a trajectory optimizer may have a state that is a function of the already discovered optimal trajectories. For example, for a given breast patient, a first optimal trajectory may have a first control point sequence 51 and energy 6X, a second optimal trajectory may have a second control point sequence S2 and energy 10X that complements the first optimal trajectory, and a third optimal trajectory with a third control point sequence S3 and energy 6X that complements the first optimal trajectory and the second optimal trajectory.

In some embodiments, considering M energy modes, the dose, score, and region sections in the trajectory optimizer may be constructed such that each connected component of the search graph corresponds to a single energy. As such, each trajectory will correspond to a fixed energy, and energy switches will take place when transitioning from one trajectory to another trajectory.

Figure 15:
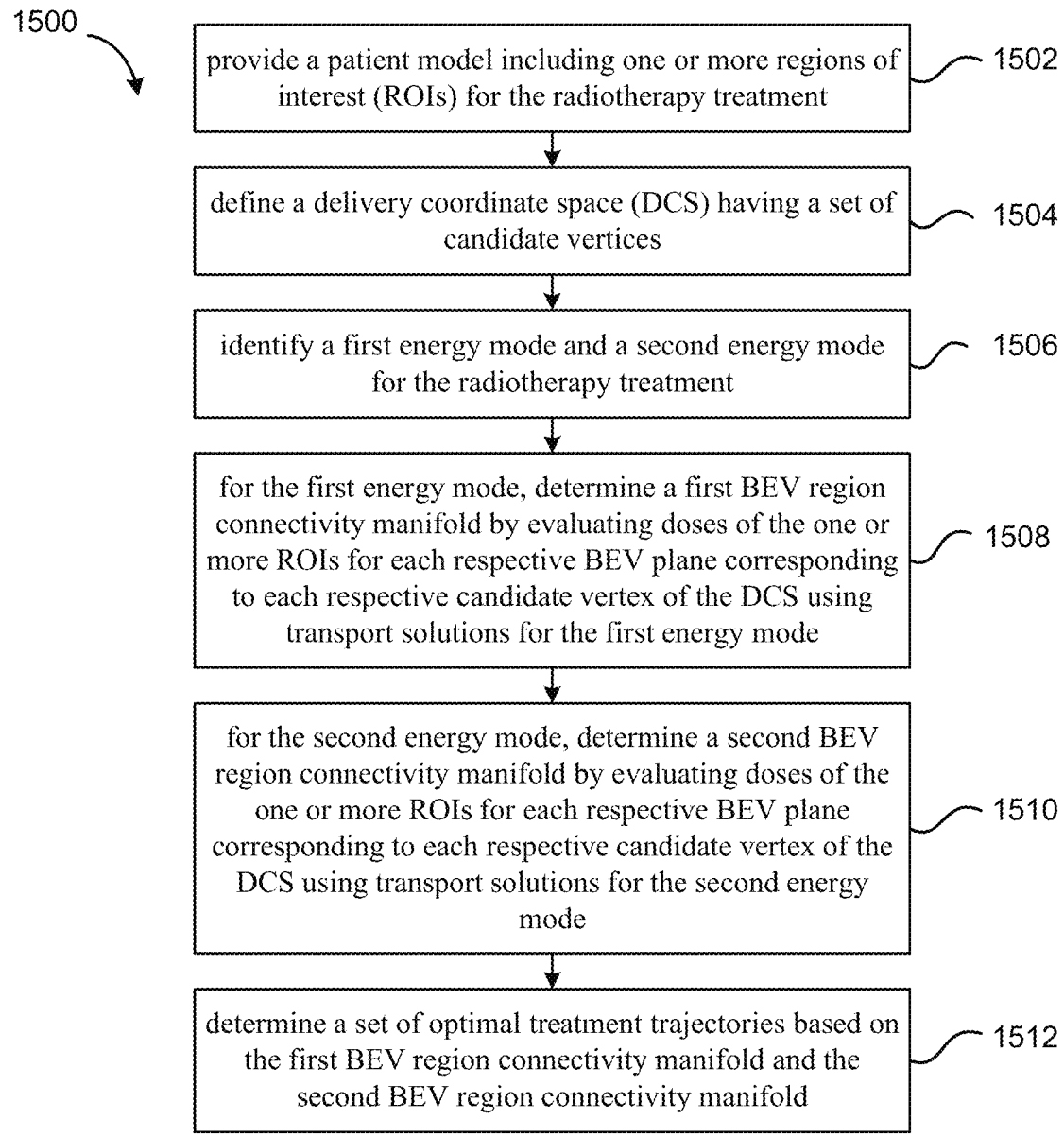
FIG. 15 is a flowchart illustrating a method of trajectory optimization considering multiple candidate energy modes according to some embodiments.

D. Second Method of Trajectory Optimization Considering Multiple Candidate Energy Modes FIG. 15 is a flowchart illustrating a method 1500 of trajectory optimization considering multiple candidate energy modes according to some other embodiments. The method 1500 may be referred to as a mixed-energy-mode trajectory optimization over multiple candidate energy modes.

At 1502, a patient model is provided. The patient model includes one or more regions of interest (ROIs) for the radiotherapy treatment.

At 1504, a delivery coordinate space (DCS) is defined. The DCS has a set of candidate vertices. Each respective candidate vertex defines a respective beam's eye view (BEV) plane.

At 1506, a first energy mode and a second energy mode are identified for the radiotherapy treatment.

At 1508, for the first energy mode, a first BEV region connectivity manifold is determined by evaluating doses of the one or more ROIs for each respective BEV plane corresponding to each respective candidate vertex of the DCS using transport solutions for the first energy mode.

At 1510, for the second energy mode, a second BEV region connectivity manifold is determined by evaluating doses of the one or more ROIs for each respective BEV plane corresponding to each respective candidate vertex of the DCS using transport solutions for the second energy mode.

At 1512, a set of optimal treatment trajectories is determined based on the first BEV region connectivity manifold and the second BEV region connectivity manifold.

It should be appreciated that the specific steps illustrated in FIG. 15 provide a particular method of trajectory optimization according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

E. Trajectory Optimization Including Consideration of Beam-Off Time

In the case of mixed-energy mode VMAT with N trajectories, the aggregate beam-off time $\Delta t = \sum_{i=1}^{N-1} \Delta t_{i,i+1}$ may include, but not limited to the following:
   a time of $\Delta t_{i,i+1}^{switch}$ to switch between energy modes $m_i$ and $m_{i+1}$ and between trajectories i and i+1;
   a time of $\Delta t_{i,i+1}^{move}$ to move machine axes from positions at the last vertex $v_i^{last}$ of trajectory i to those at the first vertex $v_{i+1}^{first}$ of trajectory i+1;
   a time of $\Delta t_{i,i+1}^{collimator}$ to rotate the collimator from its position $c_i^{last}$ at the last vertex of trajectory i to its position $c_{i+1}^{first}$ at the first vertex of trajectory i+1;
   a time of $\Delta t_{i,i+1}^{imaging}$ of acquiring an image or multiple images for guidance of treatment between the end of trajectory i and the beginning of trajectory i+1.

The first item on the list arises from the introduction of multiple energy modes.

There may exist a multitude of ways to minimize the aggregate beam-off time $\Delta t$. In some embodiments, constraints may be imposed in a multi-energy mode VMAT optimization algorithm to minimize the temporal distance between the last node of trajectory i, $n_{last}^{(i)}$ and the first node of trajectory i+1, $n_{first}^{(i+1)}$ minimal. This may be achieved by minimizing one or several of the constituents of $\Delta t_{i,i+1}$ for each i∈{1, 2, . . . , N}. This may be referred to as the optimization of the radiation order. In some other embodiments, the radiation order of the beams may be determined as a post-processing step without the imposition of constraints between first and last nodes. In some further embodiments, a combination of minimization internal to the algorithm and post-processing may be used.

VIII. Beam Angle Optimization Considering Multiple Candidate Energy Modes

In some embodiments, the beam angle optimization (BAO) method described above may be generalized to consider multiple candidate energy modes using two different approaches. In a first approach, a beam angle optimization is performed for each of a plurality of candidate energy modes to obtain a respective candidate set of field geometries for each candidate energy mode. The candidate set of field geometries that gives rise to the optimal value of an objective function ("score") may be picked as the optimal set of field geometries. In some embodiments, the objective function is the max-distance function in beam angle optimization, as discussed above. The optimal set of field geometries will be used in the IMRT radiotherapy treatment at the energy mode corresponding to the optimal set of field geometries. This approach may be referred to as single-energy-mode beam angle optimization over multiple candidate energy modes.

In a second approach, the end result of a beam angle optimization considering multiple candidate energy modes may be a set of field geometries, possibly with different energy modes (e.g., some field geometries in the set may correspond to a first energy mode, while some other field geometries in the set may correspond to a second energy mode different from the first energy mode). The second approach may be referred to as mixed-energy-mode beam angle optimization over multiple candidate energy modes.

A. Single-Energy-Mode Beam Angle Optimization Over Multiple Candidate Energy Modes According to some embodiments, to find an optimal energy mode for a set of k beams among M candidate energy modes (indexed as m=1, ... M), the BAO method described above may be run M times, one for each of the M candidate energy modes. This process may produce M candidate sets of k beams, each candidate set corresponding to a respective energy mode. The candidate set that gives rise to the optimal value of an objective function ("score") may be picked as the optimal set of k beams, which will be used for the IMRT radiotherapy treatment at the energy mode corresponding to the optimal set of k beams.

Figure 16:
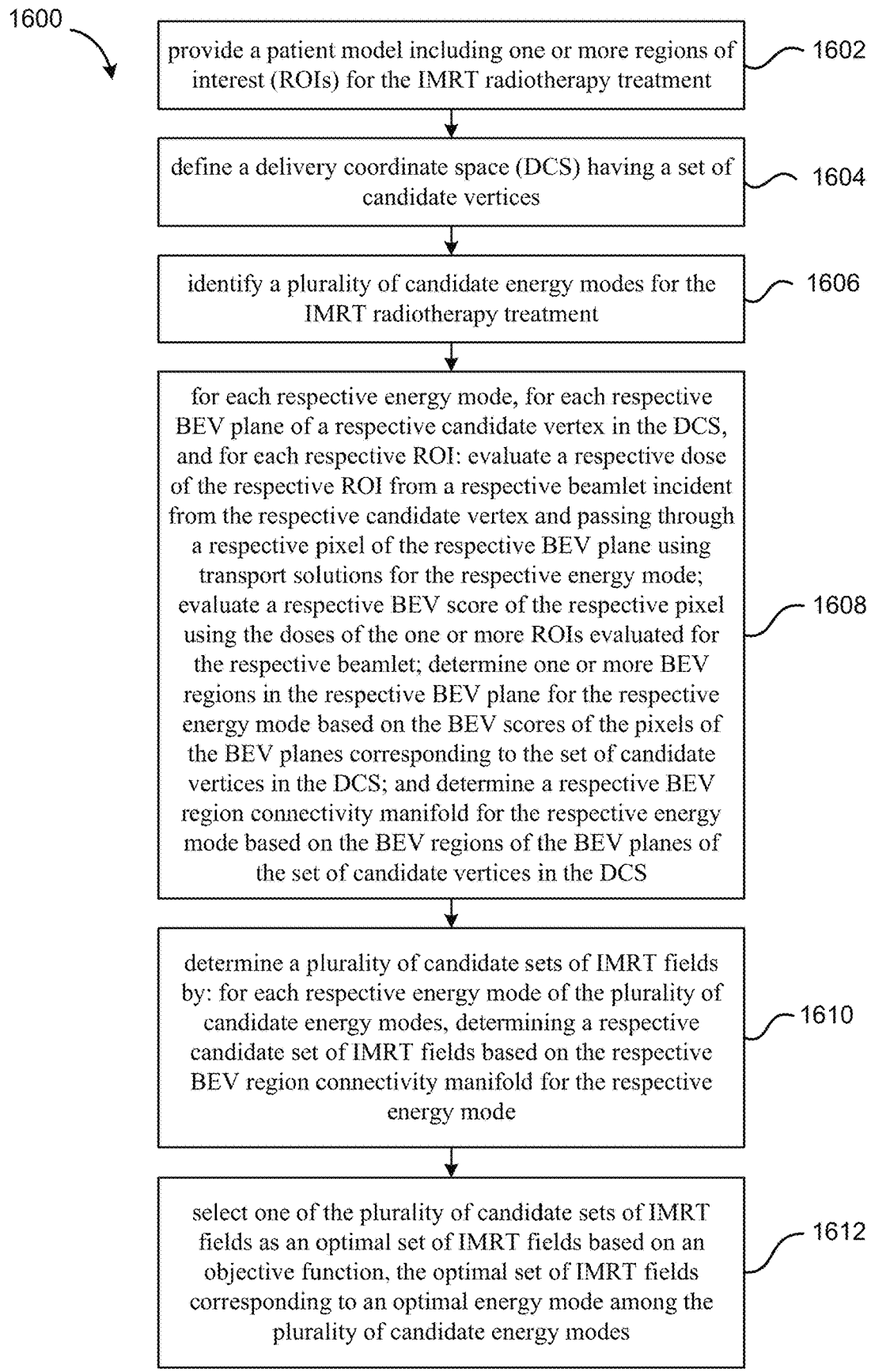
FIG. 16 is a flowchart illustrating a method of beam angle optimization considering multiple candidate energy modes according to some embodiments.

B. First Method of Beam Angle Optimization Considering Multiple Candidate Energy Modes FIG. 16 is a flowchart illustrating a method 1600 of beam angle optimization for an IMRT radiotherapy treatment considering multiple candidate energy modes according to some other embodiments. The method 1600 may be referred to as a sing-energy-mode beam angle optimization over multiple candidate energy modes, as discussed above.

At 1602, a patient model is provided. The patient model includes one or more regions of interest (ROIs) for the IMRT radiotherapy treatment.

At 1604, a delivery coordinate space (DCS) is defined. The DCS has a set of candidate vertices. Each respective candidate vertex defines a respective beam's eye view (BEV) plane.

At 1606, a plurality of candidate energy modes is identified for the IMRT radiotherapy treatment.

At 1608, for each respective energy mode of the plurality of candidate energy modes, for each respective BEV plane of a respective candidate vertex in the DCS, and for each respective ROI of the one or more ROIs: a respective dose of the respective ROI from a respective beamlet incident from the respective candidate vertex and passing through a respective pixel of the respective BEV plane is evaluated using transport solutions for the respective energy mode; a respective BEV score of the respective pixel is evaluated using the doses of the one or more ROIs evaluated for the respective beamlet; one or more BEV regions in the respective BEV plane for the respective energy mode are determined based on the BEV scores of the pixels of the BEV planes corresponding to the set of candidate vertices in the DCS; and a respective BEV region connectivity manifold for the respective energy mode is determined based on the BEV regions of the BEV planes of the set of candidate vertices in the DCS. The respective BEV region connectivity manifold represents connections between contiguous BEV regions between adjacent vertices.

At 1610, a plurality of candidate sets of IMRT fields is determined by: for each respective energy mode of the plurality of candidate energy modes, determining a respective candidate set of IMRT fields based on the respective BEV region connectivity manifold for the respective energy mode. Each respective IMRT field defines a beam angle corresponding to a respective vertex in the DCS.

At 1612, one of the plurality of candidate sets of IMRT fields are selected as an optimal set of IMRT fields based on an objective function. The optimal set of IMRT fields corresponds to an optimal energy mode among the plurality of candidate energy modes.

It should be appreciated that the specific steps illustrated in FIG. 16 provide a particular method of beam angle optimization for an IMRT radiotherapy treatment according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

C. Mixed-Energy-Mode Beam Angle Optimization Over Multiple Candidate Energy Modes According to some embodiments, to find a set of k beams among M candidate energy modes (indexed as m=1, ... M), in which the k beams may have different energy modes, a multi-energy-mode BAO graph based on the TORUS graph concept may be built based on the following nodes and edges:

Nodes

Nodes are a set $\mathcal{N}$ of N tuples of the form (energy mode, vertex, collimator index, region mask). Each tuplet may determine a single field. An energy mode may correspond to a combination of photon energy and primary fluence mode. A vertex may correspond to a location in a discretized delivery coordinate space (DCS), equivalent to specifying the isocenter, and gantry and couch angles for a C-arm linear accelerator. A collimator index may correspond to a collimator angle out of a set of discrete possible collimator angles. A region mask may correspond a set of contiguous target regions the MLC leaves may expose.

Edges

Edges are connections between neighbor nodes that have vertex-vertex connectivity in the underlying delivery coordinate space, and MLC connectivity between the respective MLC leaf sequences. In some embodiments, there may be a connection between node $n_1=(m_1, v, c, b)$ and node $n_2=(m_2, v, c, b)$ for any $m_1$ and $m_2$ among the M energy modes under consideration. In some embodiments, there may be no edge between node $(m_1, v_1, c_1, b_1)$ and node $(m_2, v_2, c_2, b_2)$ if $v_1 \neq v_2$ or $c_1 \neq c_2$ or $b_1 \neq b_2$. In the case of beam-angle optimization, the MLC connectivity constraint may not be important, but it may nevertheless act to reduce the number of edges in the graph. Thus, it may be computationally useful to keep the MLC connectivity constraint.

In the TORUS framework described above, min-distances and max-distances are defined along edges in the TORUS graph. In the case of static fields, there is no gantry motion while the treatment beam is on. Therefore, only the vertices themselves matter, and there is no need for a min-distance function. The score (max-distance) may be the metric to optimize. The score S may be defined on subsets of nodes as, $$S(\mathcal{B})=\text{max-distance corresponding to the set of nodes (beams)} \mathcal{B} \subset \mathcal{N}. \quad (18)$$

The optimal set of k beams may be defined to be the subset $\mathcal{B} \subset \mathcal{N}$ with $|\mathcal{B}|=k$ that gives an optimal score $S(\mathcal{B})$, where $|\mathcal{B}|$ represents the number of beams in the subset $\mathcal{B} \subset \mathcal{N}$.

The score may be a complex non-local function of the entire subset $\mathcal{B}$. Therefore, it may be a non-trivial problem to solve exactly. However, there may exist an efficient way to find approximate solutions faster than trying all $_NC_k$ combinations.

In some embodiments, a mixed-energy-mode-IMRT-plan BAO optimization may include the following steps:

1. Evaluate the scores for individual beams ($|\mathcal{B}|=1$), and use the squares of these scores as sampling probabilities.
2. Randomly sample k beams using above probabilities.
3. Apply local gradient descent to this set $\mathcal{B}$ to find a local minimum.
4. Repeat steps 1-3 until there is no improvement in score found for a predetermined number of successive trials (e.g., 20 successive trials).

This procedure may be referred to as a gradient descent method. During each iteration of the gradient descent procedure, all possible "edges" may be considered looking for improvement, where an "edge" is motion of the subset $\mathcal{B}$ to a neighbor subset $\mathcal{B}'$. The subset of beams may be updated to move in the direction that most improves the score. This is repeated until no more local improvements in the score is found. A neighbor to subset $\mathcal{B}$ is defined to be another subset B' that differs in exactly one beam $B_i \to B_i'$, where these two beams either share an edge in the TORUS graph or have the same position in the delivery coordinate space (same vertex).

Figure 17:
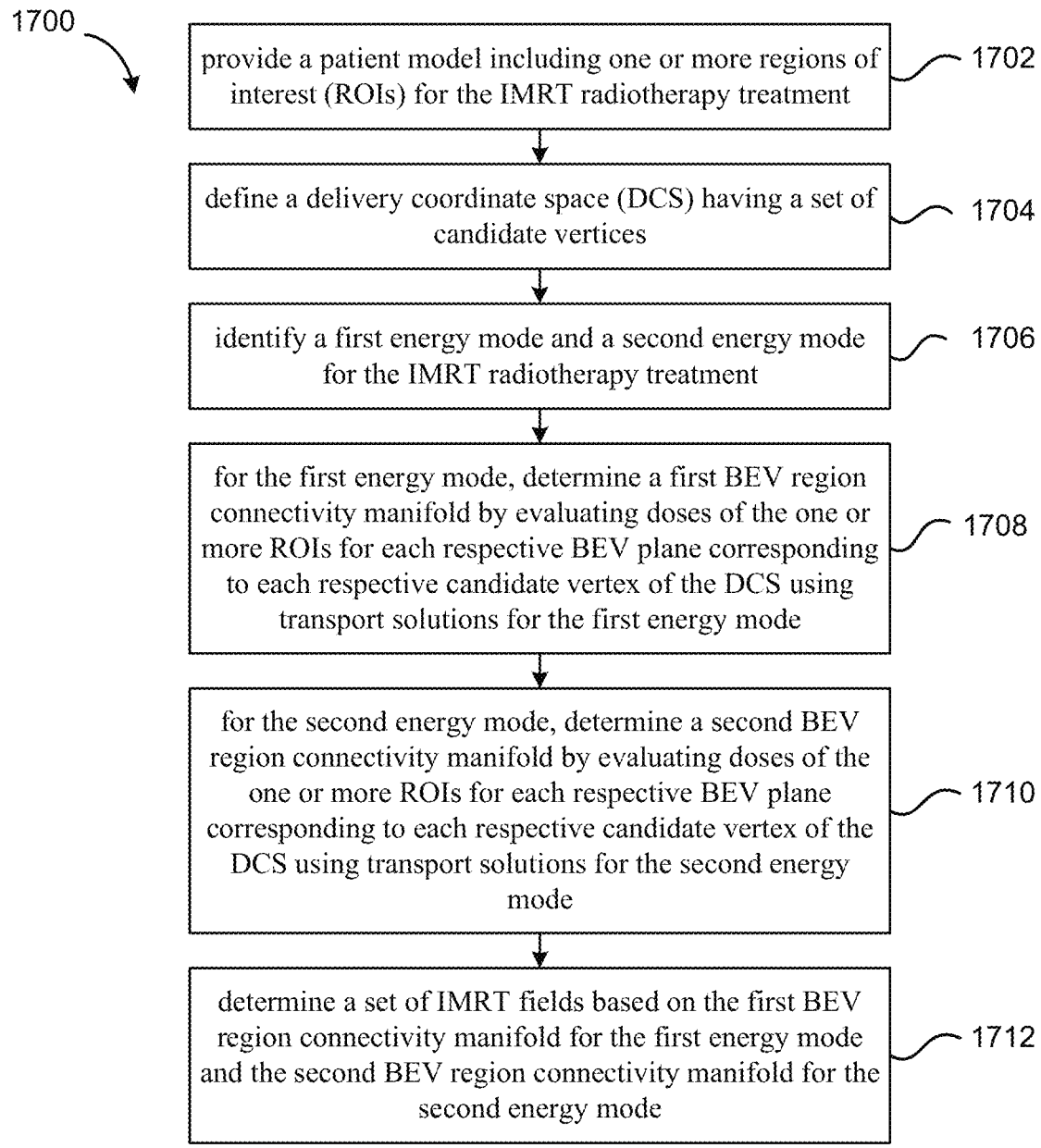
FIG. 17 is a flowchart illustrating a method of beam angle optimization considering multiple candidate energy modes according to some embodiments.

D. Second Method of Beam Angle Optimization Considering Multiple Candidate Energy Modes FIG. 17 is a flowchart illustrating a method 1700 of beam angle optimization for an IMRT radiotherapy treatment considering multiple candidate energy modes according to some other embodiments. The method 1700 may be referred to as mixed-energy-mode beam angle optimization over multiple candidate energy modes, as discussed above.

At 1702, a patient model is provided. The patient model includes one or more regions of interest (ROIs) for the IMRT radiotherapy treatment.

At 1704, a delivery coordinate space (DCS) is defined. The DCS has a set of candidate vertices. Each respective candidate vertex defines a respective beam's eye view (BEV) plane.

At 1706, a first energy mode and a second energy mode are identified for the IMRT radiotherapy treatment.

At 1708, for the first energy mode, a first BEV region connectivity manifold is determined by evaluating doses of the one or more ROIs for each respective BEV plane corresponding to each respective candidate vertex of the DCS using transport solutions for the first energy mode.

At 1710, for the second energy mode, a second BEV region connectivity manifold is determined by evaluating doses of the one or more ROIs for each respective BEV plane corresponding to each respective candidate vertex of the DCS using transport solutions for the second energy mode.

At 1720, a set of IMRT fields is determined based on the first BEV region connectivity manifold for the first energy mode and the second BEV region connectivity manifold for the second energy mode. Each respective IMRT field of the set of IMRT fields defines a beam angle corresponding to a respective vertex in the DCS.

It should be appreciated that the specific steps illustrated in FIG. 17 provide a particular method of beam angle optimization for an IMRT radiotherapy treatment according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

E. Beam Angle Optimization Including Consideration of Beam-Off Time

Consider a multi-energy mode IMRT treatment as an external-beam radiotherapy treatment, where the dose is delivered from k static beam locations $r_i=(m_i,v_i,c_i)$, $i=1, \ldots, k$, where the indices $m_i$, $v_i$, and $c_i$ correspond to the energy mode, vertex, and collimator angle, respectively. In a C-arm linear accelerator treatment system, a vertex may include an isocenter, a gantry angle, and a couch angle. In other types of external-beam radiation treatment systems, a vertex may include other treatment axes variables. The fluence delivered from each $r_i$ may be determined by way of a fluence-optimization scheme that distributes the fluence optimally between the $r_i$ such that clinical optimization objectives are fulfilled.

A dosimetrically optimal IMRT treatment plan with multi-energy modes may be found within a given delivery coordinate space by running fluence optimization and leaf sequencing for each permissible combination of $\{r_i\}r_{i=1}^k$, and by picking the dosimetrically optimal one. However, this process may be impractical due to the large number of possible combinations. Moreover, it may be desirable that the patient and the patient's internal organs remain stationary during the administration of radiation for the delivered dose to match the planned dose. The longer the treatment takes, the more likely that the patient or the patient's internal organs may move during the treatment, and hence a higher probability of not delivering the intended dose to the target volumes.

The overall treatment time may be prolonged by the beam-off transition times from beam $r_i$ to $r_{i+1}$. The total beam-off transition time from beam $r_i$ to $r_{i+1}$ may be expressed as $\Delta t_{i,i+1}=\max_j \Delta t_{i,i+1}^{change_j}$, where the changes may include, but are limited to the following:

a time of $\Delta t_{i,i+1}^{switch}$ to switch between energy modes $m_i$ and $m_{i+1}$;

a time of $\Delta t_{i,i+1}^{move}$ to move machine axes from positions at vertex $v_i$ to those at $v_{i+1}$;

a time of $\Delta t_{i,i+1}^{collimator}$ to rotate the collimator from $c_i$ to $c_{i+1}$;

a time of $\Delta t_{i,i+1}^{imaging}$ of acquiring an image or multiple images for guidance of treatment between beams i and i+1.

The first item on the list arises from the introduction of multiple energy modes.

A minimization of the aggregate beam-off time $\Delta t = \Sigma_{i=1}^{k-1} \Delta t_{i,i+1}$ may be an important part of the beam-selection problem. In some embodiments, a multi-energy BAO algorithm may include constraints on picking beams that can be delivered in a time-efficient radiation order. In some other embodiments, the radiation order of the beams may be determined as a post-processing step.

IX. Hybrid Trajectory and Beam Angle Optimization

The TORUS approach described above may find continuous trajectories amenable to VMAT-like delivery in a given delivery coordinate space. The requirement of spatial continuity in TORUS may come at the potential expense of reduction in dosimetric plan quality. To overcome this potential drawback, the VMAT trajectories may be augmented by placing one or more IMRT fields, either in the same delivery coordinate space as the VMAT trajectories or in a different delivery coordinate space. The IMRT fields may be obtained using the methods described above in Section VI. The resulting treatment geometry may be referred to as a hybrid VMAT-IMRT treatment geometry.

Hybrid VMAT-IMRT treatment geometries may be generated in a multitude of ways. In the following, cases that are either inherently time-efficient or may provide a significant improvement in dosimetric plan quality at the expense of longer treatment times according to some embodiments are discussed.

A. VMAT Treatment Geometry Augmented with IMRT Fields in the Same Delivery Coordinate Space Assume that a VMAT treatment geometry of N trajectories has been generated in a given delivery coordinate space, which may be abbreviated as $DCS_1$, using any of the procedures described above in Section V for a given energy mode. A given delivery coordinate space includes a set of vertices that represent permissible directions of incidence that would not result in collisions (e.g., machine-to-machine collisions and machine-to-patient collisions). In some embodiments, the VMAT treatment geometry may be augmented by placing k IMRT fields along one or more trajectories of the N trajectories. The k IMRT fields may be obtained using any of the methods described above in Section VI. In some other embodiments, the angles of the k IMRT fields along the VMAT-like trajectories may be selected by means different from those described above in Section VI, in conjunction with concurrent optimization of MU time series and leaf positioning.

As an example, consider a C-arm linear accelerator radiotherapy treatment system illustrated in FIG. 18A. The radiotherapy treatment system includes a couch 1802 for supporting a patient 1806 (a patient dummy is shown), and a gantry 1804 that rotates around the couch 1802. Consider a first delivery coordinate space $DCS_1$, which has a fixed isocenter, a couch angle of 0 deg, and a gantry angle interval of [0 deg, 360 deg), as illustrated in FIG. 18A. $DCS_1$ may be referred to as a "coplanar" delivery coordinate space. FIG. 18B shows a view of a patient model 1810 from the top of the patient's head and a VMAT-like arc 1820. In this case, the VMAT-like arc 1820 happens to a complete circle around the patient's head (e.g., for treating intracranial metastasis). The VMAT-like arc 1820 may be obtained by a TORUS trajectory optimization described above in Section V.

In some embodiments, one or more IMRT fields may be inserted at certain directions along the VMAT-like arc 1820 to augment the VMAT-like arc 1820. The directions of the IMRT fields may be determined using a beam angle optimization described above in Section VI. Alternatively, a radiologist may determine that delivering more radiation doses at those directions may improve the dosimetry quality of the radiotherapy treatment. Such a hybrid VMAT-IMRT treatment geometry may be efficient in terms of total delivery time. For example, the radiotherapy treatment system may start delivery of the VMAT-like arc 1820 by rotating the gantry 18004 along the VMAT-like arc 1820, then stop at the IMRT angle to deliver the IMRT field, and then resume rotating the gangry 1804 from that angle to complete the VMAT-like arc 1820. In this manner, the radiotherapy treatment may not incurre any beam-off transition time between delivery of the VMAT-like arc 1820 and the delivery of the IMRT field.

In some embodiments, a TORUS trajectory optimization may generate additional VMAT-like arcs in the same delivery coordinate space $DCS_1$. For example, as shown in FIG. 18B, a second VMAT-like arc 1830 may be generated. In this case, the second VMAT-like arc 1830 is not a complete circle, but is missing a section in the fourth quadrant on the upper left. (The second VMAT-like arc 1830 may have an MLC leaf sequence whose apertures may overlap fully, partially or not at all with those of the first VMAT-like arc 1820 at vertices common to both VMAT-like arcs 1820 and 1830.)

It is possible that a beam angle optimization may identify one or more optimal directions of IMRT fields (e.g., the direction indicated by the dashed line 1840 in FIG. 18B) that fall in the missing quadrant (note those angles are still in the same delivery coordinate space $DCS_1$).

In some embodiments, if a VMAT treatment geometry includes a first arc 1820 and a second arc 1830, and the direction 1840 of the IMRT field falls on only the first arc 1820, the IMRT field may be delivered in conjunction with the delivery of the first arc 1820, instead of in conjunction with the delivery of the second arc 1830. This ordering of the hybrid VMAT-IMRT treatment geometry may be more time-efficient than the case if the IMRT field is delivered in conjunction with the delivery of the second arc 1830. This is because, in the latter case, the radiotherapy treatment system may need to turn off the radiation beam (either in the middle of the second arc 1830 or after completing the second arc 1830), rotate the gantry 1804 to the direction 1840 of the IMRT field, then deliver the IMRT field. Therefore, the radiotherapy treatment may incurre some beam-off transition time.

In some embodiments, it may happen that an optimal direction of a IMRT field does not fall on any of the N trajectories of the VMAT treatment geometry. For instance, in the example illustrated in FIG. 18C, assume that the VMAT treatment geometry includes two VMAT-like arcs 1850 and 1860. The combination of the two arcs 1850 and 1860 does not cover a complete circle. It may be possible that an optimal direction 1870 of the IMRT field may fall on neither of the two arcs 1850 and 1860. In some embodiments, such a hybrid VMAT-IMRT treatment geometry may still be preferred, if the IMRT field provides a significant improvement in dosimetric plan quality, or it may improve the patient's quality of life (e.g., if the patient's eyesight may be saved), albeit at the expense of longer treatment time.

In some embodiments, multiple treatment axes may rotate and/or translate concurrently in a VMAT-like trajectory. The treatment axes may include, for example, the couch position (in three degrees of freedom), the couch angle (pitch, yaw, and roll), the collimator angle, and the like, in addition to the gantry angle. For instance, the couch can be rotated simultaneously with the rotation of the gantry. The collimator may be also be rotated at the same time. In some embodiments, a TORUS trajectory optimization algorithm may generate such multi-axes trajectories.

Figure 19:
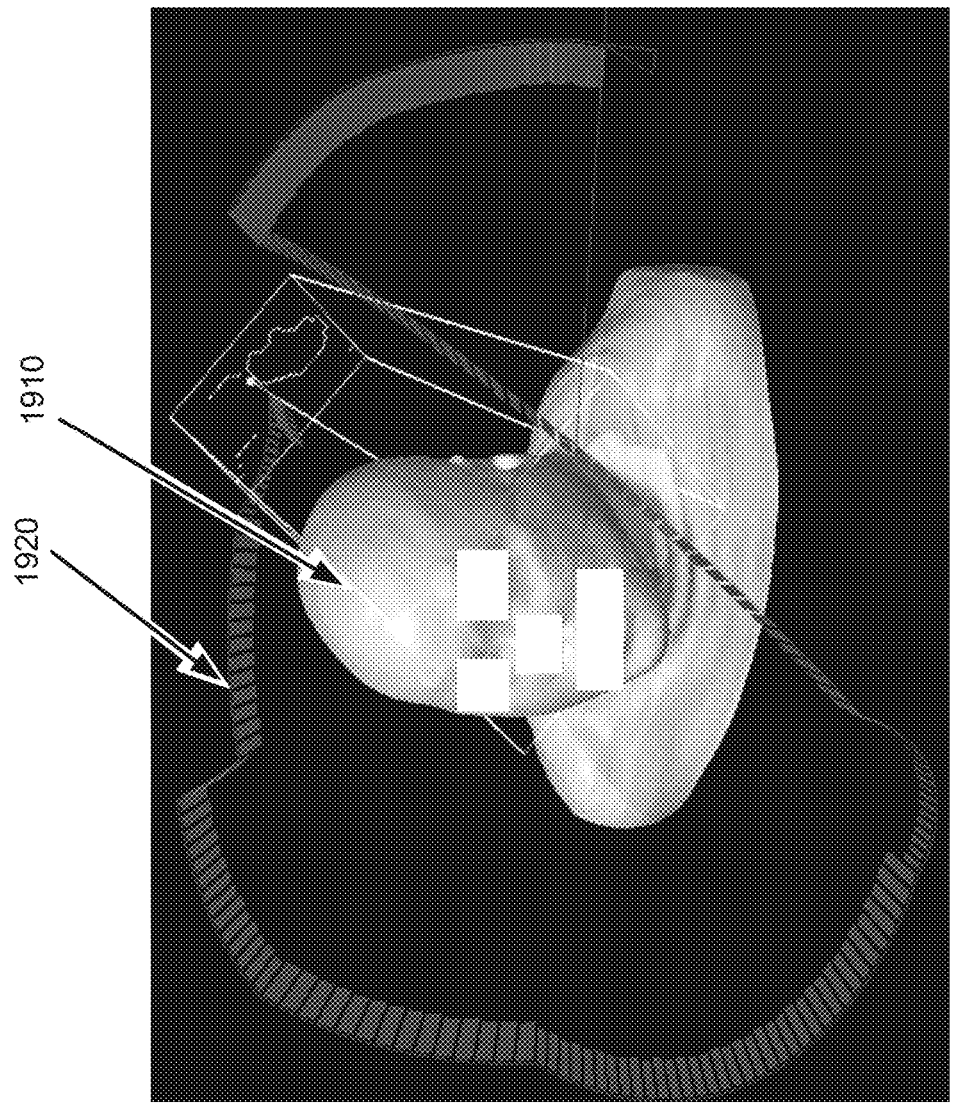
FIG. 19 shows an example of a more general treatment trajectory superimposed on a patient model according to some embodiments.

FIG. 19 shows an example of a more general VMAT-like trajectory 1920 superimposed on a patient model 1910. Similar to the examples discussed above in conjunction with FIG. 18B, one or more IMRT fields may be inserted along certain directions along the VMAT-like trajectory 1920, to result in a time-efficient hybrid VMAT-IMRT treatment geometry. Alternatively, a hybrid VMAT-IMRT treatment geometry may include IMRT fields that do not fall on the VMAT-like trajectory 1920, if those IMRT fields may improve the dosimetric plan quality or improve the patient's quality of life.

It should be understood that the methods discussed above are not limited to the couch model illustrated in FIG. 18A, but can be applied to other couch models. The methods are also not limited to C-arm linear accelerator radiotherapy treatment systems, but can be applied to other types of radiotherapy treatment systems.

B. First Method of Hybrid VMAT-IMRT Treatment Geometry Optimization

Figure 20:
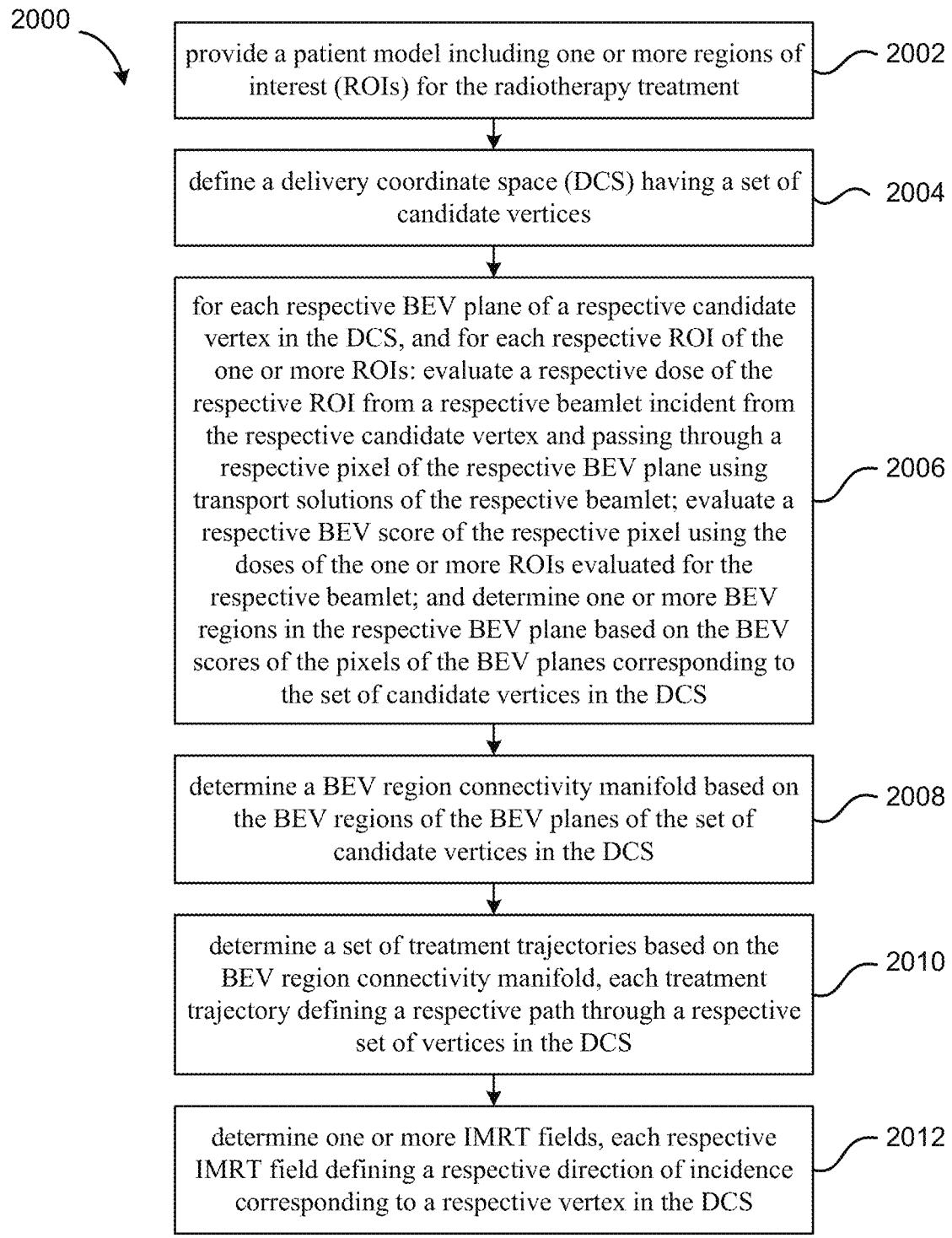
FIG. 20 is a flowchart illustrating a method of hybrid VMAT-IMRT treatment geometry optimization according to some embodiments.

FIG. 20 is a flowchart illustrating a method 2000 of hybrid VMAT-IMRT treatment geometry optimization according to some embodiments.

At 2002, a patient model is provided. The patient model includes one or more regions of interest (ROIs) for the radiotherapy treatment.

At 2004, a delivery coordinate space (DCS) is defined. The DCS has a set of candidate vertices. Each respective candidate vertex defines a respective beam's eye view (BEV) plane.

At 2006, for each respective BEV plane of a respective candidate vertex in the DCS, and for each respective ROI of the one or more ROIs: a respective dose of the respective ROI from a respective beamlet incident from the respective candidate vertex and passing through a respective pixel of the respective BEV plane is evaluated using transport solutions of the respective beamlet; a respective BEV score of the respective pixel is evaluated using the doses of the one or more ROIs evaluated for the respective beamlet; and one or more BEV regions in the respective BEV plane are determining based on the BEV scores of the pixels of the BEV planes corresponding to the set of candidate vertices in the DCS.

At 2008, a BEV region connectivity manifold is determined based on the BEV regions of the BEV planes of the set of candidate vertices in the DCS. The BEV region connectivity manifold represents connections between contiguous BEV regions between adjacent vertices.

At 2010, a set of treatment trajectories is determined based on the BEV region connectivity manifold. Each treatment trajectory defines a respective path through a respective set of vertices in the DCS.

At 2012, one or more IMRT fields are determined. Each respective IMRT field defines a respective direction of incidence corresponding to a respective vertex in the DCS.

It should be appreciated that the specific steps illustrated in FIG. 20 provide a particular method of hybrid VMAT-IMRT treatment geometry optimization according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

C. VMAT Treatment Geometry Augmented with IMRT Fields on a Different Delivery Coordinate Space In some embodiments, VMAT-like trajectories may be augmented by placing k IMRT fields generated using the methods described in Section VI in the union of $DCS_1$ and another delivery coordinate space, $DCS_2$. As an example, consider a C-arm linear accelerator. A first delivery coordinate space $DCS_1$ may have a fixed isocenter, a couch angle of 0 deg, and a gantry angle interval of [0 deg, 360 deg), as illustrated in FIG. 21A. A second delivery coordinate space $DCS_2$ may have the same isocenter as $DCS_1$, a couch angle of 90 deg with an associated gantry angle interval of (180 deg, 360 deg], or a couch angle of 270 deg with an associated gantry angle interval of [0 deg, 180 deg), as illustrated in FIG. 21C. $DCS_1$ and $DCS_2$ are two coplanar delivery coordinate spaces but on different planes, and the only vertex they share has a gantry angle of 0 deg since rotating the couch does not change the direction of incidence when the gantry angle is equal to 0 deg. FIG. 21B shows a VMAT-like trajectory 2120 in $DCS_1$ (which happens to be a complete circle) superimposed on a patient model 2110. $DCS_2$ may provide a non-coplanar extension for shaping the entry and exit doses about the treatment target. Thus, in some embodiments, one or more IMRT fields may be added in $DCS_2$ to augment the VMAT treatment geometry in $DCS_1$, forming a hybrid VMAT-IMRT treatment geometry in two different delivery coordinate spaces.

Figure 22:
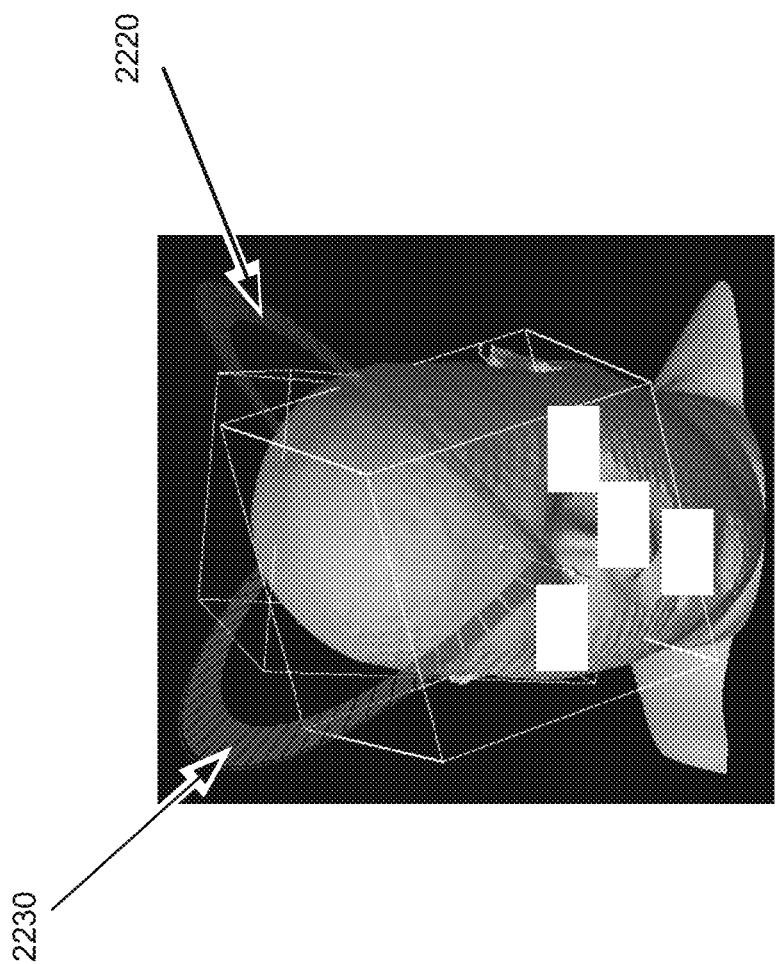
FIG. 22 shows two treatment trajectories in a third delivery coordinate space and a fourth delivery coordinate space, respectively.

In some embodiments, a VMAT-IMRT treatment geometry may include additional VMAT-like trajectories in additional delivery coordinate spaces. For example, FIG. 21D shows a VMAT-like trajectory 2130 in $DCS_2$. FIG. 22 shows two VMAT-like trajectores 2220 and 2230 in a third delivery coordinate space $DCS_3$ and a fourth delivery coordinate space $DCS_4$, respectively. Thus, in some exemplary embodiments, a VMAT treatment geometry may include four (or more) VMAT-like trajectories in four (or more) different delivery coordinate spaces. While it may be more complicated to deliver a radiotherapy treatment in multiple delivery coordinate spaces, such multi-DCS treatment geometry may be selected if it may improve the dosimetric plan quality.

D. Second Method of Hybrid VMAT-IMRT Treatment Geometry Optimization

Figure 23:
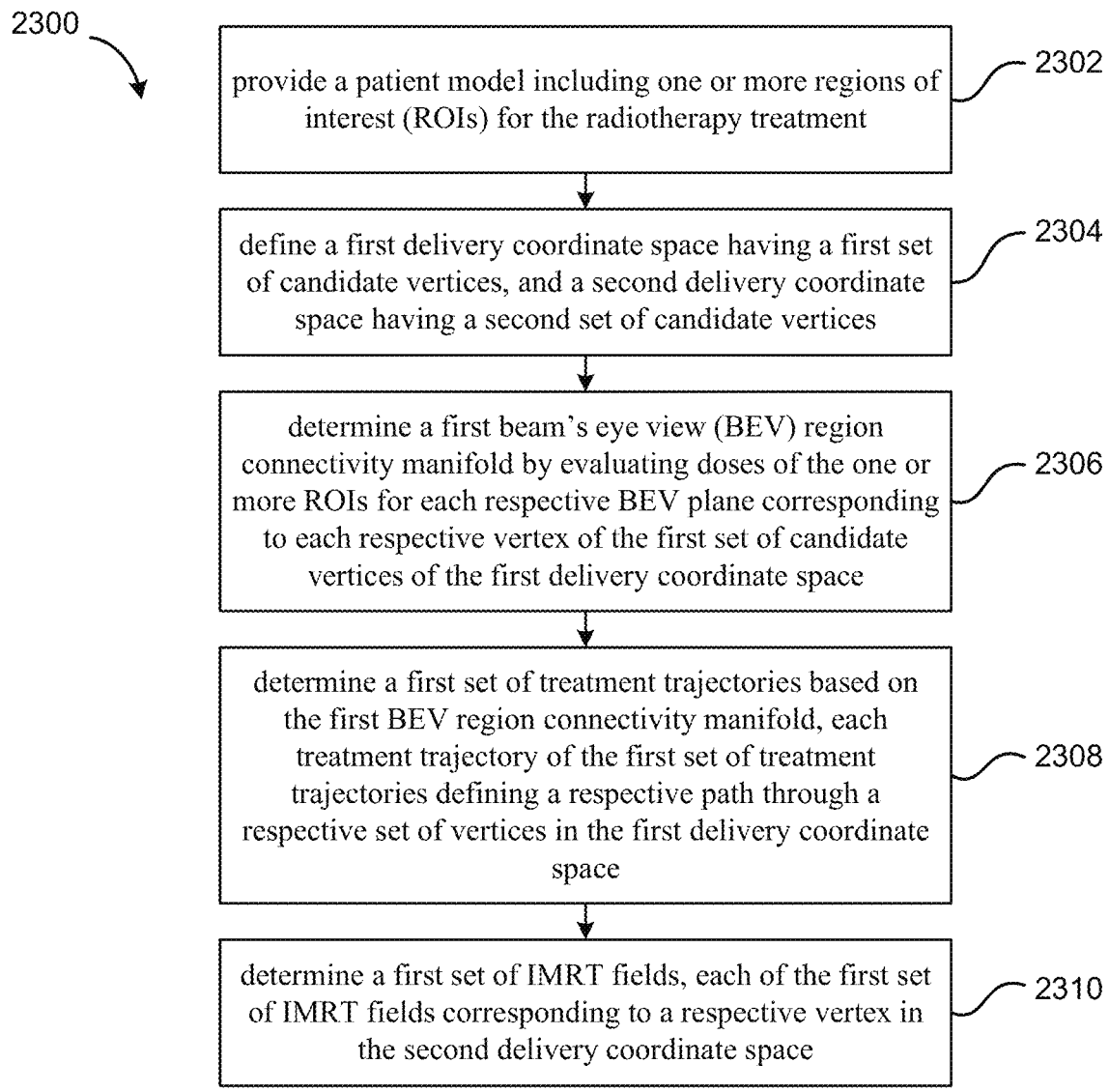
FIG. 23 is a flowchart illustrating a method of hybrid VMAT-IMRT treatment geometry optimization according to some embodiments.

FIG. 23 is a flowchart illustrating a method 2300 of hybrid VMAT-IMRT treatment geometry optimization according to some embodiments.

At 2302, a patient model is provided. The patient model includes one or more regions of interest (ROIs) for the radiotherapy treatment.

At 2304, a first delivery coordinate space and a second delivery coordinate space is defined. The first delivery coordinate space has a first set of candidate vertices. The second delivery coordinate space has a second set of candidate vertices. Each vertex of the first set of candidate vertices or the second set of candidate vertices defines a respective beam's eye view (BEV) plane.

At 2306, a first beam's eye view (BEV) region connectivity manifold is determined by evaluating doses of the one or more ROIs for each respective BEV plane corresponding to each respective vertex of the first set of candidate vertices of the first delivery coordinate space.

At 2308, a first set of treatment trajectories is determined based on the first BEV region connectivity manifold. Each treatment trajectory of the first set of treatment trajectories defines a respective path through a respective set of vertices in the first delivery coordinate space.

At 2310, a first set of IMRT fields is determined. Each of the first set of IMRT fields corresponds to a respective vertex in the second delivery coordinate space.

It should be appreciated that the specific steps illustrated in FIG. 23 provide a particular method of hybrid VMAT-IMRT treatment geometry optimization according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

E. VMAT Treatment Geometry Augmented with IMRT Fields on the Same Delivery Coordinate Space with Mixed Energy Modes Assume that a VMAT-treatment geometry of N trajectories include trajectories of different energy modes. For example, as discussed above in Section VII.C., a trajectory optimization algorithm may generate some trajectories of a first energy mode and some other trajectories in a second energy mode different from the first energy mode. In some embodiments, the VMAT-treatment geometry may be augmented by placing k IMRT fields along the trajectories, such that the energy mode of each IMRT field corresponds to the energy mode of the VMAT-like trajectory on which the IMRT field sits. The k IMRT fields may be obtained using any of the methods described above in Sections VI and VIII. This method may not incur additional treatment delivery time due to energy switching between VMAT and IMRT fields. Note also that the positions of the IMRT fields may be set prior to concurrent optimization of MU time series and leaf positioning.

In some other embodiments, the positions of the k IMRT fields along the VMAT-like trajectories may be selected by means different from those described above in Section VI, in conjunction with concurrent optimization of MU time series and leaf positioning.

In some embodiments, within $DCS_1$, but outside of trajectories, the set of viable energy modes for the IMRT fields may be determined based on other constraints such as total delivery time of treatment.

F. Third Method of Hybrid VMAT-IMRT Treatment Geometry Optimization

Figure 24:
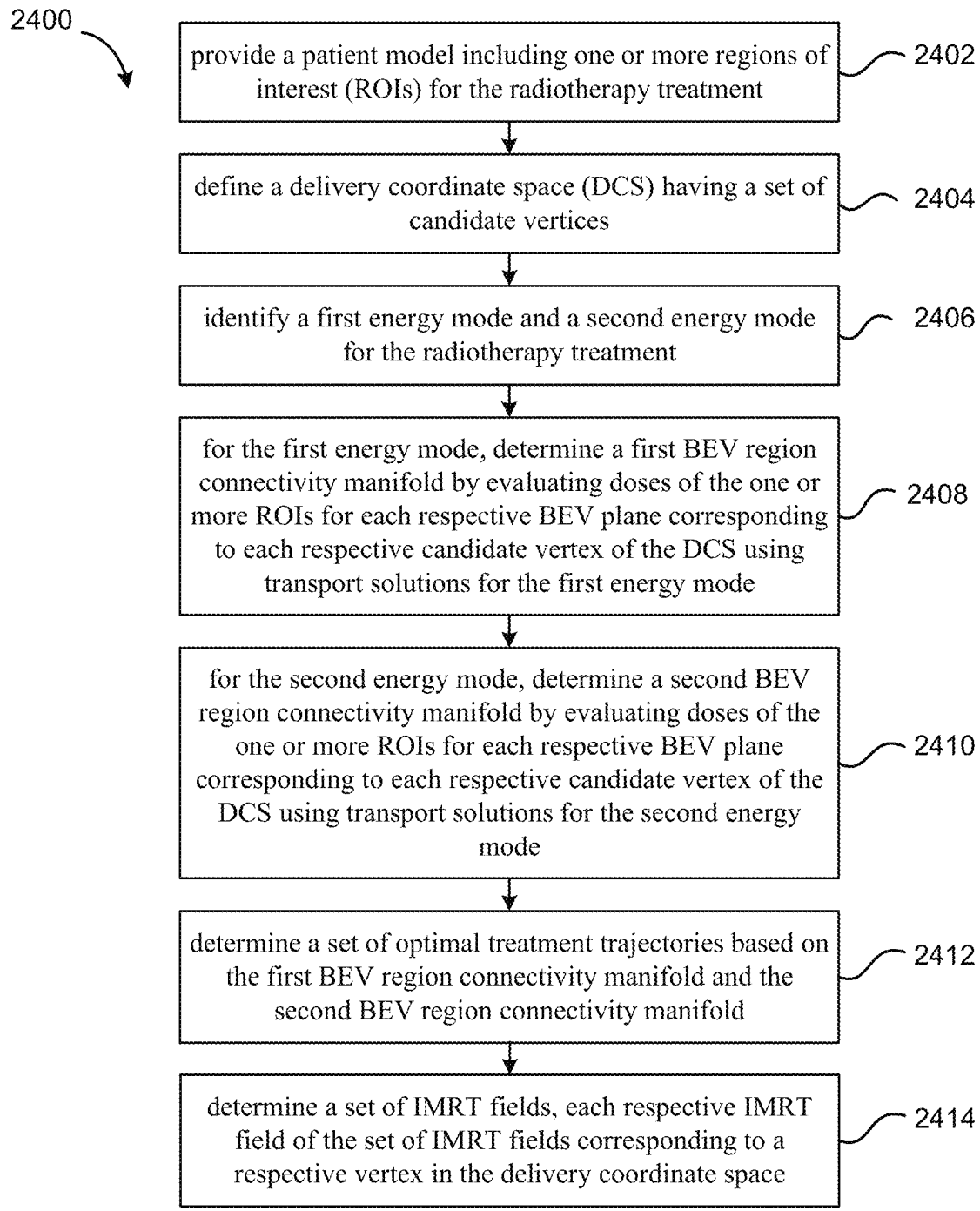
FIG. 24 is a flowchart illustrating a method of hybrid VMAT-IMRT treatment geometry optimization according to some embodiments.

FIG. 24 is a flowchart illustrating a method 2400 of hybrid VMAT-IMRT treatment geometry optimization according to some embodiments.

At 2402, a patient model is provided. The patient model includes one or more regions of interest (ROIs) for the radiotherapy treatment.

At 2404, a delivery coordinate space (DCS) is defined. The DCS has a set of candidate vertices. Each respective candidate vertex defines a respective beam's eye view (BEV) plane.

At 2406, a first energy mode and a second energy mode are identified for the radiotherapy treatment.

At 2408, for the first energy mode, determine a first BEV region connectivity manifold by evaluating doses of the one or more ROIs for each respective BEV plane corresponding to each respective candidate vertex of the DCS using transport solutions for the first energy mode.

At 2410, for the second energy mode, determine a second BEV region connectivity manifold by evaluating doses of the one or more ROIs for each respective BEV plane corresponding to each respective candidate vertex of the DCS using transport solutions for the second energy mode.

At 2412, a set of optimal treatment trajectories is determined based on the first BEV region connectivity manifold and the second BEV region connectivity manifold.

At 2414, a set of IMRT fields is determined. Each respective IMRT field of the set of IMRT fields corresponds to a respective vertex in the delivery coordinate space.

It should be appreciated that the specific steps illustrated in FIG. 24 provide a particular method of hybrid VMAT-IMRT treatment geometry optimization according to some embodiments. Other sequences of steps may also be performed according to alternative embodiments. For example, alternative embodiments may perform the steps in a different order. Moreover, the individual steps may include multiple sub-steps that may be performed in various sequences as appropriate to the individual step. Furthermore, additional steps may be added and some steps may be removed depending on the particular applications. One of ordinary skill in the art would recognize many variations, modifications, and alternatives.

X. Computer System

Figure 25:
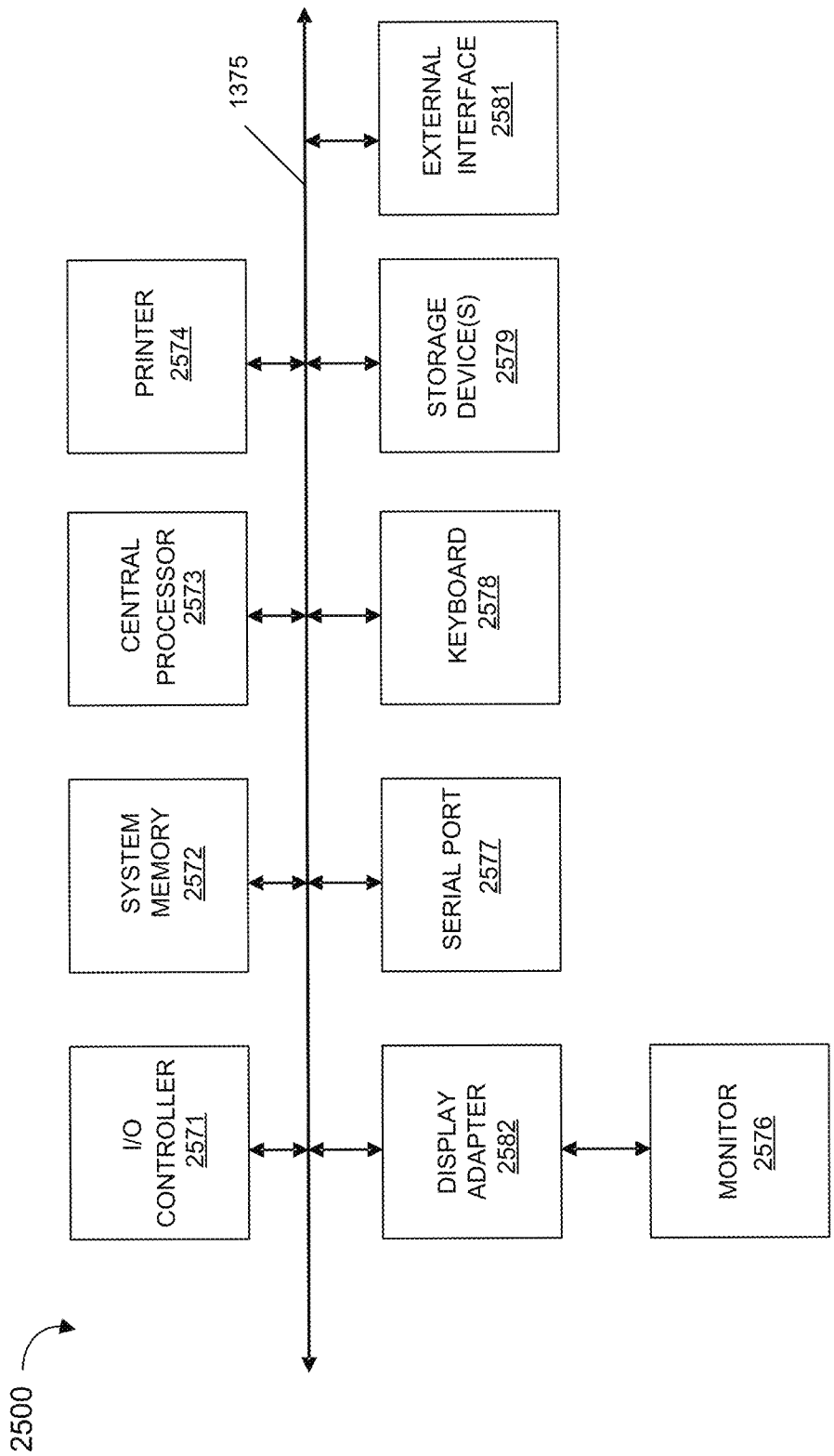
FIG. 25 shows a block diagram of an example computer system usable with system and methods according to embodiments.

Any of the computer systems mentioned herein may utilize any suitable number of subsystems. Examples of such subsystems are shown in FIG. 25 in computer system 2000. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 25 are interconnected via a system bus 2575. Additional subsystems such as a printer 2574, keyboard 2578, storage device(s) 2579, monitor 2576, which is coupled to display adapter 2582, and others are shown. Peripherals and input/output (I/O) devices, which couple to I/O controller 2571, can be connected to the computer system by any number of means known in the art, such as serial port 2577. For example, serial port 2577 or external interface 2581 (e.g. Ethernet, Wi-Fi, etc.) can be used to connect computer system 2500 to a wide area network such as the Internet, a mouse input device, or a scanner. The interconnection via system bus 2575 allows the central processor 2573 to communicate with each subsystem and to control the execution of instructions from system memory 2572 or the storage device(s) 2579 (e.g., a fixed disk, such as a hard drive or optical disk), as well as the exchange of information between subsystems. The system memory 2572 and/or the storage device(s) 2579 may embody a computer readable medium. Any of the data mentioned herein can be output from one component to another component and can be output to the user.

A computer system can include a plurality of the same components or subsystems, e.g., connected together by external interface 2581 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

External interface 2581 can be used to transmit one or more treatment plans to one or more radiation treatment devices, as described herein. For example, a treatment planning application can reside on a server computer, and a client computer can use the treatment planning application. The server computer can be part of a cloud computing platform that provides software as a service (SaaS). Once a treatment plan is determined, a client computer can specify which radiation device or a treatment plan database accessible by the radiation device for transmitting one or more files encapsulating the treatment plan. For instance, an IP address can be specified.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned herein are incorporated by reference in their entirety for all purposes. None is admitted to be prior art.

What is claimed is:

1. A method of beam angle optimization for an IMRT radiotherapy treatment, the method comprising:
    providing a patient model including one or more regions of interest (ROIs) for the IMRT radiotherapy treatment;
    defining a delivery coordinate space (DCS) having a set of candidate vertices, each respective candidate vertex defining a respective beam's eye view (BEV) plane;
    for each respective ROI of the one or more ROIs:
        solving an adjoint transport to obtain an adjoint solution field from the respective ROI; and
        for each respective candidate vertex in the DCS:
            for each respective pixel of the respective BEV plane defined by the respective candidate vertex:
                evaluating an adjoint photon fluence originating from a respective beamlet incident from the respective candidate vertex and passing through the respective pixel by performing ray tracing of the adjoint solution field; and
                evaluating a respective dose of the respective ROI from the respective beamlet using the adjoint photon fluence;
    for each respective candidate vertex in the DCS:
        for each respective pixel of the respective BEV plane defined by the respective candidate vertex:
            evaluating a respective BEV score of the respective pixel using the doses of the one or more ROIs evaluated for the respective beamlet incident from the respective candidate vertex and passing through the respective pixel; and
            determining one or more BEV regions in the respective BEV plane based on the BEV scores of the pixels of the BEV planes corresponding to the set of candidate vertices in the DCS;
    determining a BEV region connectivity manifold based on the BEV regions of the BEV planes of the set of candidate vertices in the DCS, the BEV region connectivity manifold representing connections between contiguous BEV regions between adjacent vertices; and
    determining a set of IMRT fields based on the BEV region connectivity manifold, each respective IMRT field of the set of IMRT fields defining a beam angle corresponding to a respective vertex in the DCS,
    wherein the IMRT fields are represented as a set of nodes, and the beam angle optimization includes finding the set of nodes that have optimal max-distance,
    wherein the method further comprises selecting order of beam delivery in the set of IMRT fields, the selecting including determining a total time the beam is off during transitioning from one IMRT field in the set to another IMRT field in the set, and determining the order in which the beam is delivered based on minimum total beam-off time,
    wherein the total beam-off time includes a time for acquiring one or more images for guidance of treatment between beam delivery, and
    wherein the method further comprises limiting beam delivery in the set of IMRT fields to beams that can be delivered in a time-efficient order.

2. The method of claim 1, wherein each candidate vertex in the DCS comprises an isocenter position, a gantry angle, a couch angle, and a collimator angle.

3. The method of claim 1, wherein determining the one or more BEV regions in the respective BEV plane defined by the respective candidate vertex comprises:
  determining a threshold BEV score based on the BEV scores of the pixels of the BEV planes corresponding to the set of candidate vertices in the DCS; and
  determining the one or more BEV regions in the respective BEV plane by comparing each respective BEV score of a respective pixel of the respective BEV plane to the threshold BEV score, wherein pixels within the one or more BEV regions have BEV scores greater than or equal to the threshold BEV score.

4. The method of claim 1, wherein the one or more ROIs include a plurality of ROIs, and wherein evaluating the BEV score for each respective pixel of the BEV plane comprises evaluating a linear combination of the doses of the plurality of ROIs.

5. The method of claim 4, wherein each respective dose of a respective ROI of the plurality of ROIs is given a respective weight in the linear combination.

6. The method of claim 5, wherein the plurality of ROIs includes one or more planning target volumes (PTVs) and one or more organs at risk (OARs).

7. The method of claim 6, wherein the respective dose of a respective ROI that is one of the one or more PTVs has a positive weight, and the respective dose of a respective ROI that is one of the one or more OARs has a negative weight.

8. The method of claim 1, wherein determining the set of IMRT fields comprises performing optimization using a max-distance function.

9. The method of claim 8, wherein the optimization is performed using a local gradient descent algorithm based on information contained in the BEV region connectivity manifold.

* * * * *